(12) United States Patent
Kurtz et al.

(10) Patent No.: US 9,456,925 B2
(45) Date of Patent: Oct. 4, 2016

(54) PHOTODISRUPTIVE LASER TREATMENT OF THE CRYSTALLINE LENS

(75) Inventors: Ronald M. Kurtz, Irvine, CA (US);
Ferenc Raksi, Mission Viejo, CA (US);
Peter Goldstein, Santa Ana, CA (US)

(73) Assignee: ALCON LENSX, INC., Aliso Viejo, CA (US)

( * ) Notice: Subject to any disclaimer, the term of this patent is extended or adjusted under 35 U.S.C. 154(b) by 1198 days.

(21) Appl. No.: 12/343,418

(22) Filed: Dec. 23, 2008

(65) Prior Publication Data

US 2009/0171327 A1   Jul. 2, 2009

Related U.S. Application Data

(63) Continuation-in-part of application No. 12/205,842, filed on Sep. 5, 2008, now abandoned.

(60) Provisional application No. 60/970,454, filed on Sep. 6, 2007.

(51) Int. Cl.
*A61F 9/008* (2006.01)
*A61F 9/009* (2006.01)

(52) U.S. Cl.
CPC .......... *A61F 9/008* (2013.01); *A61F 9/00838* (2013.01); *A61F 9/009* (2013.01); *A61F 2009/0087* (2013.01);
(Continued)

(58) Field of Classification Search
CPC .......... A61B 18/18; A61B 8/00; G01B 9/02
USPC .......... 606/6, 5, 8, 10, 4; 600/439; 356/450
See application file for complete search history.

(56) References Cited

U.S. PATENT DOCUMENTS

| 4,481,948 A | 11/1984 | Sole |
| 4,538,608 A | 9/1985 | L'Esperace, Jr. |

(Continued)

FOREIGN PATENT DOCUMENTS

| EP | 0724929 | 8/1996 |
| EP | 1252872 | 10/2002 |

(Continued)

OTHER PUBLICATIONS

Kim Sang Woo, PCT/US2009/069510 International Search Report, dated Sep. 13, 2010, issued by the Korean Intellectual Property Office and to be published by USPTO (13 pages).

(Continued)

*Primary Examiner* — William Thomson
*Assistant Examiner* — Victor Shapiro
(74) *Attorney, Agent, or Firm* — S. Brannon Latimer

(57) ABSTRACT

Apparatus and methods of treating a hard lens region of an eye with a laser where one method includes identifying a boundary of the hard lens region, selecting a laser-parameter to enable a photodisruptive procedure in the hard lens region and to control a spreading of bubbles in the hard lens region, modifying a mechanical property of a posterior portion of the hard lens region in a proximity of the identified boundary by the photodisruptive procedure, and modifying a mechanical property of a portion anterior to the modified posterior portion of the hard lens region by the photodisruptive procedure. The laser bubbles can be applied to form incisions which are non transverse to an axis of the eye and intersect the lens fibers.

27 Claims, 31 Drawing Sheets

(52) U.S. Cl.
CPC ............... *A61F 2009/00851* (2013.01); *A61F 2009/00895* (2013.01); *A61F 2009/00897* (2013.01)

(56) References Cited

U.S. PATENT DOCUMENTS

| | | |
|---|---|---|
| 4,554,917 A | 11/1985 | Tagnon |
| 4,633,866 A | 1/1987 | Peyman et al. |
| 4,638,801 A | 1/1987 | Daly et al. |
| 4,686,366 A | 8/1987 | Stuke |
| 4,694,828 A | 9/1987 | Eichenbaum |
| 4,766,896 A | 8/1988 | Pao |
| 4,888,015 A | 12/1989 | Domino |
| 4,907,586 A | 3/1990 | Bille et al. |
| 5,013,319 A | 5/1991 | Davis |
| 5,036,592 A | 8/1991 | Marshall |
| 5,089,022 A | 2/1992 | Koester et al. |
| 5,139,022 A | 8/1992 | Lempert |
| 5,225,862 A | 7/1993 | Nagano et al. |
| 5,246,435 A | 9/1993 | Bille et al. |
| 5,261,923 A | 11/1993 | Soares |
| 5,269,787 A | 12/1993 | Cozean, Jr. et al. |
| 5,333,018 A | 7/1994 | Heine et al. |
| 5,336,215 A | 8/1994 | Hsueh et al. |
| 5,423,841 A | 6/1995 | Kornefeld |
| 5,439,462 A | 8/1995 | Bille et al. |
| 5,442,412 A | 8/1995 | Frey et al. |
| 5,520,679 A | 5/1996 | Lin |
| 5,549,596 A | 8/1996 | Latina |
| 5,549,632 A | 8/1996 | Lai |
| 5,656,186 A | 8/1997 | Mourou et al. |
| 5,669,923 A | 9/1997 | Gordon |
| 5,738,677 A | 4/1998 | Colvard et al. |
| 5,957,921 A | 9/1999 | Mirhashemi et al. |
| 5,968,095 A | 10/1999 | Norrby |
| 5,984,916 A | 11/1999 | Lai |
| 5,987,151 A | 11/1999 | Akashi |
| 5,993,438 A | 11/1999 | Juhasz et al. |
| 6,004,314 A | 12/1999 | Wei et al. |
| 6,010,497 A | 1/2000 | Tang et al. |
| 6,066,138 A | 5/2000 | Sheffer et al. |
| 6,099,522 A | 8/2000 | Knopp et al. |
| 6,146,375 A | 11/2000 | Juhasz et al. |
| 6,165,190 A | 12/2000 | Nguyen |
| 6,197,018 B1 | 3/2001 | O'Donnell, Jr. |
| 6,217,570 B1 | 4/2001 | Nevyas |
| 6,254,595 B1 | 7/2001 | Juhasz et al. |
| 6,322,556 B1 | 11/2001 | Gwon et al. |
| 6,328,732 B1 | 12/2001 | Donitzky et al. |
| 6,344,040 B1 | 2/2002 | Juhasz et al. |
| RE37,585 E | 3/2002 | Mourou et al. |
| 6,379,005 B1 | 4/2002 | Williams et al. |
| 6,391,020 B1 | 5/2002 | Kurtz et al. |
| 6,409,718 B1 | 6/2002 | Tang |
| 6,451,006 B1 | 9/2002 | Bille |
| 6,454,761 B1 | 9/2002 | Freedman |
| 6,508,812 B1 | 1/2003 | Williams et al. |
| 6,579,282 B2 | 6/2003 | Bille et al. |
| 6,610,051 B2 | 8/2003 | Bille |
| 6,620,160 B2 | 9/2003 | Lewis et al. |
| 6,623,476 B2 | 9/2003 | Juhasz et al. |
| 6,676,653 B2 | 1/2004 | Juhasz et al. |
| 6,712,809 B2 | 3/2004 | Li et al. |
| 6,726,679 B1 | 4/2004 | Dick et al. |
| 6,730,074 B2 | 5/2004 | Bille et al. |
| 6,751,033 B2 | 6/2004 | Goldstein et al. |
| 6,863,667 B2 | 3/2005 | Webb et al. |
| 6,899,707 B2 | 5/2005 | Scholler et al. |
| 6,902,561 B2 | 6/2005 | Kurtz et al. |
| 6,913,603 B2 | 7/2005 | Knopp et al. |
| 6,986,763 B2 | 1/2006 | Holmén |
| 6,991,629 B1 | 1/2006 | Juhasz et al. |
| 7,018,376 B2 | 3/2006 | Webb et al. |
| 7,027,233 B2 | 4/2006 | Goldstein et al. |
| 7,044,602 B2 | 5/2006 | Chernyak |
| 7,101,364 B2 | 9/2006 | Bille |
| 7,131,968 B2 | 11/2006 | Bendett et al. |
| 7,163,543 B2 | 1/2007 | Smedley et al. |
| 7,284,858 B2 | 10/2007 | Bergner et al. |
| 7,351,241 B2 * | 4/2008 | Bendett et al. ............... 606/3 |
| 7,371,230 B2 | 5/2008 | Webb et al. |
| 7,390,089 B2 | 6/2008 | Loesel et al. |
| 7,391,520 B2 | 6/2008 | Zhou et al. |
| 7,402,159 B2 | 7/2008 | Loesel et al. |
| 7,655,002 B2 * | 2/2010 | Myers ............... 606/5 |
| 7,742,173 B2 | 6/2010 | Yun et al. |
| 2002/0013574 A1 | 1/2002 | Elbrecht et al. |
| 2002/0097374 A1 | 7/2002 | Payne et al. |
| 2002/0133145 A1 | 9/2002 | Gerlach et al. |
| 2002/0193704 A1 | 12/2002 | Goldstein et al. |
| 2002/0198516 A1 | 12/2002 | Knopp et al. |
| 2003/0073983 A1 | 4/2003 | Bille |
| 2004/0039378 A1 | 2/2004 | Lin |
| 2004/0043310 A1 | 3/2004 | Takeishi et al. |
| 2004/0044355 A1 | 3/2004 | Nevyas |
| 2004/0102765 A1 | 5/2004 | Koenig |
| 2004/0106929 A1 | 6/2004 | Masket |
| 2004/0151466 A1 | 8/2004 | Crossman-Bosworth et al. |
| 2004/0199149 A1 | 10/2004 | Myers et al. |
| 2004/0215175 A1 | 10/2004 | Feklistov et al. |
| 2004/0243111 A1 | 12/2004 | Bendett et al. |
| 2004/0243112 A1 | 12/2004 | Bendett et al. |
| 2004/0243113 A1 | 12/2004 | Sugiura et al. |
| 2004/0243233 A1 | 12/2004 | Phillips |
| 2004/0254568 A1 | 12/2004 | Rathjen |
| 2005/0015120 A1 | 1/2005 | Seibel et al. |
| 2005/0024586 A1 | 2/2005 | Teiwes et al. |
| 2005/0081393 A1 | 4/2005 | Su et al. |
| 2005/0090813 A1 | 4/2005 | Schweitzer et al. |
| 2005/0107773 A1 | 5/2005 | Bergt et al. |
| 2005/0165386 A1 | 7/2005 | Kurtz et al. |
| 2005/0165387 A1 | 7/2005 | Lubatschowski et al. |
| 2005/0173817 A1 | 8/2005 | Fauver et al. |
| 2005/0192562 A1 | 9/2005 | Loesel et al. |
| 2005/0245915 A1 | 11/2005 | Loesel et al. |
| 2005/0284774 A1 | 12/2005 | Mordaunt |
| 2005/0286019 A1 | 12/2005 | Wiltberger et al. |
| 2005/0288745 A1 | 12/2005 | Andersen et al. |
| 2006/0020172 A1 | 1/2006 | Luerssen et al. |
| 2006/0100613 A1 | 5/2006 | McArdle et al. |
| 2006/0179992 A1 | 8/2006 | Kermani |
| 2006/0187462 A1 | 8/2006 | Srinivasan et al. |
| 2006/0192921 A1 | 8/2006 | Loesel et al. |
| 2006/0195076 A1 | 8/2006 | Blumenkranz et al. |
| 2006/0217688 A1 | 9/2006 | Lai |
| 2006/0235428 A1 | 10/2006 | Silvestrini |
| 2006/0264990 A1 | 11/2006 | Michelson et al. |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0147730 A1 | 6/2007 | Wiltberger et al. |
| 2007/0173759 A1 | 7/2007 | Augustine et al. |
| 2007/0173794 A1 | 7/2007 | Frey et al. |
| 2007/0173795 A1 | 7/2007 | Frey |
| 2007/0185475 A1 | 8/2007 | Frey et al. |
| 2007/0189664 A1 | 8/2007 | Andersen et al. |
| 2007/0230520 A1 | 10/2007 | Mordaunt et al. |
| 2007/0293851 A1 | 12/2007 | Muhlhoff et al. |
| 2008/0033406 A1 | 2/2008 | Andersen et al. |
| 2008/0049188 A1 | 2/2008 | Wiltberger et al. |
| 2008/0071254 A1 | 3/2008 | Lummis et al. |
| 2008/0088795 A1 | 4/2008 | Goldstein et al. |
| 2008/0281303 A1 | 11/2008 | Culbertson et al. |
| 2008/0281413 A1 | 11/2008 | Culbertson et al. |
| 2008/0319427 A1 | 12/2008 | Palanker |
| 2009/0012507 A1 | 1/2009 | Culbertson et al. |
| 2009/0048586 A1 | 2/2009 | Krueger et al. |
| 2009/0088734 A1 | 4/2009 | Mordaunt |
| 2009/0137988 A1 | 5/2009 | Kurtz |
| 2009/0137991 A1 | 5/2009 | Kurtz |
| 2009/0137993 A1 | 5/2009 | Kurtz |
| 2009/0143772 A1 | 6/2009 | Kurtz |
| 2009/0149840 A1 | 6/2009 | Kurtz |

(56) References Cited

U.S. PATENT DOCUMENTS

| | | |
|---|---|---|
| 2009/0149841 A1 | 6/2009 | Kurtz |
| 2009/0177189 A1 | 7/2009 | Raksi |
| 2010/0004641 A1 | 1/2010 | Frey et al. |
| 2010/0004643 A1 | 1/2010 | Frey et al. |
| 2010/0022994 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0110377 A1 | 5/2010 | Maloca et al. |
| 2010/0324542 A1 | 12/2010 | Kurtz et al. |
| 2010/0324543 A1 | 12/2010 | Kurtz et al. |

FOREIGN PATENT DOCUMENTS

| | | |
|---|---|---|
| EP | 1302186 | 4/2003 |
| JP | 8-206869 | 8/1996 |
| JP | 2002-330989 | 11/2002 |
| JP | 2003-180728 | 7/2003 |
| JP | 2004-106048 | 4/2004 |
| JP | 2006-528502 | 12/2006 |
| KR | 2002-0093935 | 12/2002 |
| WO | 98/27863 | 7/1998 |
| WO | 03/005920 | 1/2003 |
| WO | 03/022168 | 3/2003 |
| WO | 2006/074469 | 7/2006 |
| WO | 2006/090217 | 8/2006 |
| WO | WO 2007012924 | 2/2007 |
| WO | 2007/084627 | 7/2007 |
| WO | 2007/084694 | 7/2007 |
| WO | 2007/103349 | 9/2007 |
| WO | 2009/039315 | 3/2009 |

OTHER PUBLICATIONS

Chinn, S.R., et al., "Optical coherence tomography using a frequency-tunable optical source," *Optics Letters*, 22(5):340-342, Mar. 1997.

Freel, C., et al., "Analysis of nuclear fiber cell compaction in transparent and cataractous diabetic human lenses by scanning electron microscopy," *BMC Ophthalmology*, 3(1):1-9, Jan. 2003.

Heys, K.R., et al., "Massive increase in the stiffness of the human lens nucleus with age: the basis for presbyopia?" *Molecular Vision*, 10:956-963, Dec. 2004.

Huber, R., et al., "Three-dimensional and C-mode OCT imaging with a compact, frequency swept laser source at 1300 nm," *Optics Express*, 13(26):10523-10538, Dec. 2005.

Sweeney, M.H.J., et al., "An Impediment to Glutathione Diffusion in Older Normal Human Lenses: a Possible Precondition for Nuclear Cataract," Experimental Eye Research, 67(5):587-595, Nov. 1998.

Yun, S.H., et al., "Wavelength-Swept Fiber Laser with Frequency Shifted Feedback and Resonantly Swept Intra-Cavity Acoustooptic Tunable Filter," IEEE Journal of Selected Topics in Quantum Electronics, 3(4):1087-1096, Aug. 1997.

Hammer, D., et al., "Shielding properties of laser-induced breakdown in water for pulse durations from 5 ns to 125 fs," *Applied Optics*, 36(22):5630-5640, Aug. 1997.

Vogel, A., et al., "Intraocular Photodisruption with Picosecond and Nanosecond Laser Pulses: Tissue Effects in Cornea, Lens, and Retina," *Ophthalmology & Visual Science*, 35(7):3032-3044, Jun. 1994.

International Search Report and Written Opinion dated Jul. 31, 2009 for International Application No. PCT/US2009/030676, filed Jan. 9, 2009 (9 pages).

International Search Report and Written Opinion dated Jun. 30, 2009 for International Application No. PCT/US2008/082156, filed Oct. 31, 2008 (9 pages).

International Search Report and Written Opinion dated Mar. 12, 2009 for International Application No. PCT/US2008/075506, filed Sep. 5, 2008 (10 pages).

International Search Report and Written Opinion dated Mar. 17, 2009 for International Application No. PCT/US2008/075509, filed Sep. 5, 2008 (10 pages).

International Search Report and Written Opinion dated Mar. 18, 2009 for International Application No. PCT/US2008/076890, filed Sep. 18, 2008 (8 pages).

International Search Report and Written Opinion dated Mar. 27, 2009 for International Application No. PCT/US2008/075911, filed Sep. 10, 2008 (9 pages).

International Search Report and Written Opinion dated Mar. 30, 2009 for International Application No. PCT/US2008/076910, filed Sep. 18, 2008 (9 pages).

European Supplementary Search Report for European Application No. 08843434, mailed Dec. 16, 2010.

European Supplementary Search Report for European Application No. 09700876.7, mailed Aug. 10, 2011, 3 pages.

International Search Report and Written Opinion dated Feb. 17, 2012 for International Application No. PCT/US2011/041677.

International Search Report and Written Opinion dated Feb. 17, 2012 for International Application No. PCT/US2011/041700.

Toyran S. et al., 2005, "Femtosecond laser photodisruption of human trabecular meshwork: an in vitro study", Experimental Eye Research, vol. 81, 298-305.

Erpelding T N et al., "Bubble-based acoustic radiation force for monitoring intraocular lens elasticity", 2004 IEEE Ultrasonics Symposium, vol. 1, pp. 732-735, Aug. 2004.

European Examination Report dated Jan. 31, 2013 for European Application No. 09835875.7, 4 pages.

Khurana, AK, Theory and Practice of Optics and Refraction, Jan. 1, 2008, p. 32.

* cited by examiner

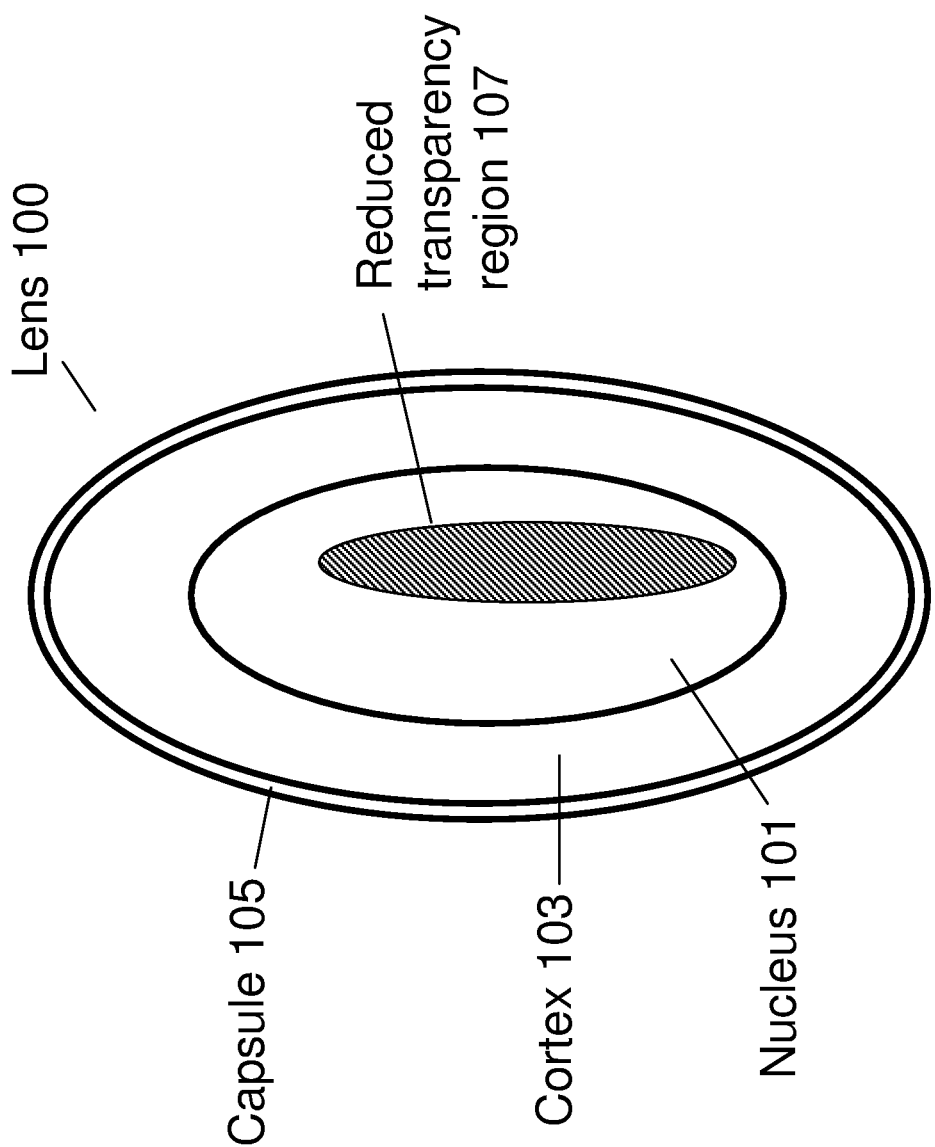

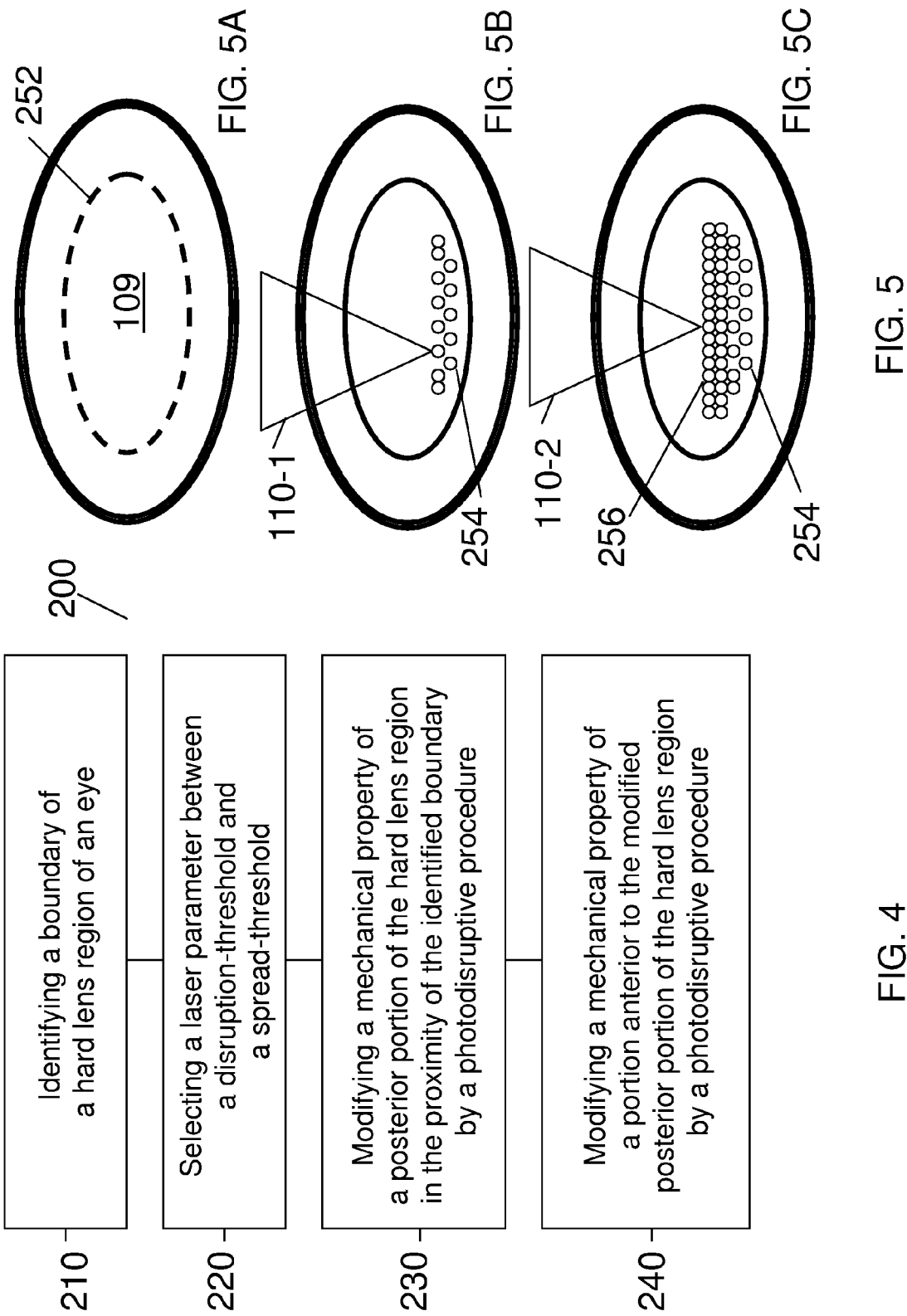

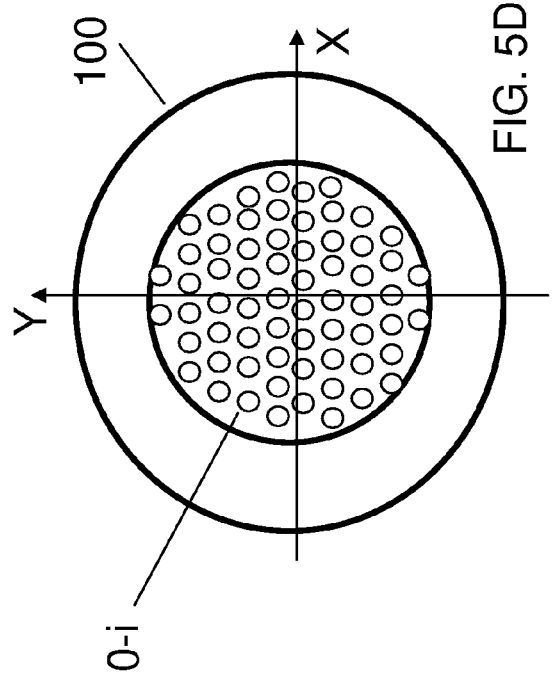
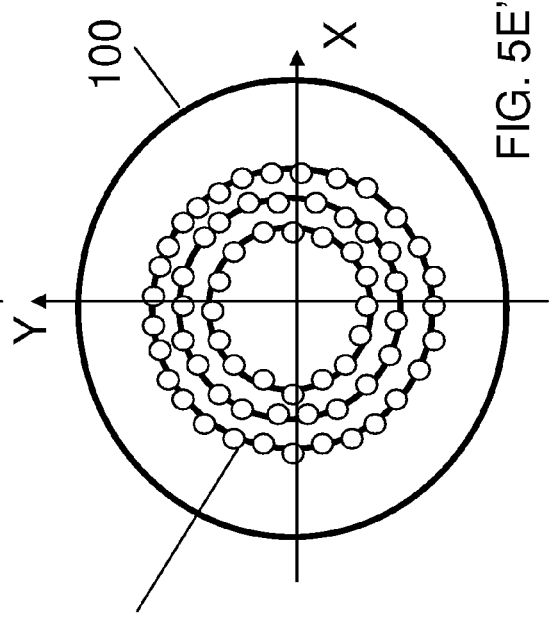
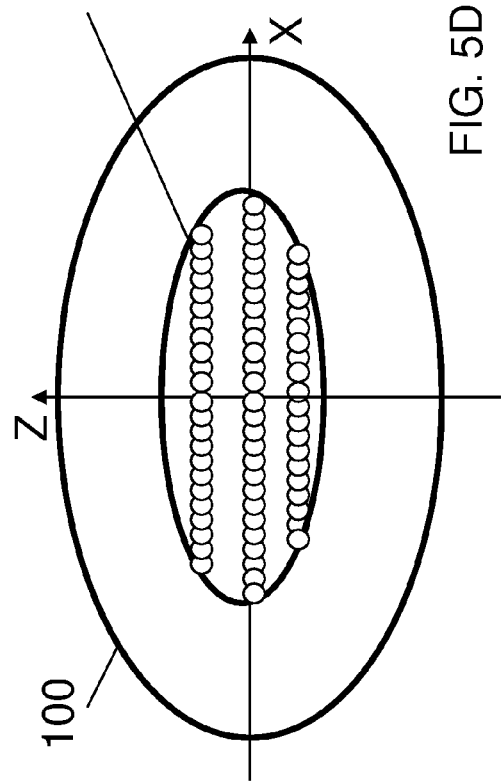
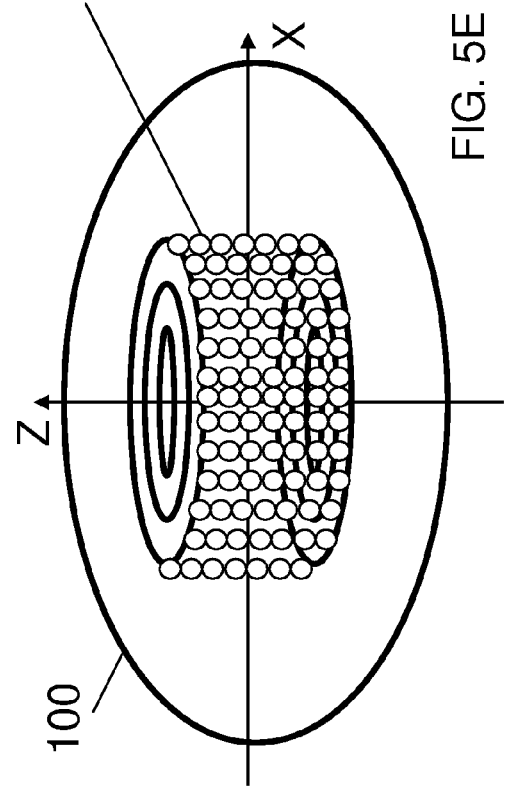

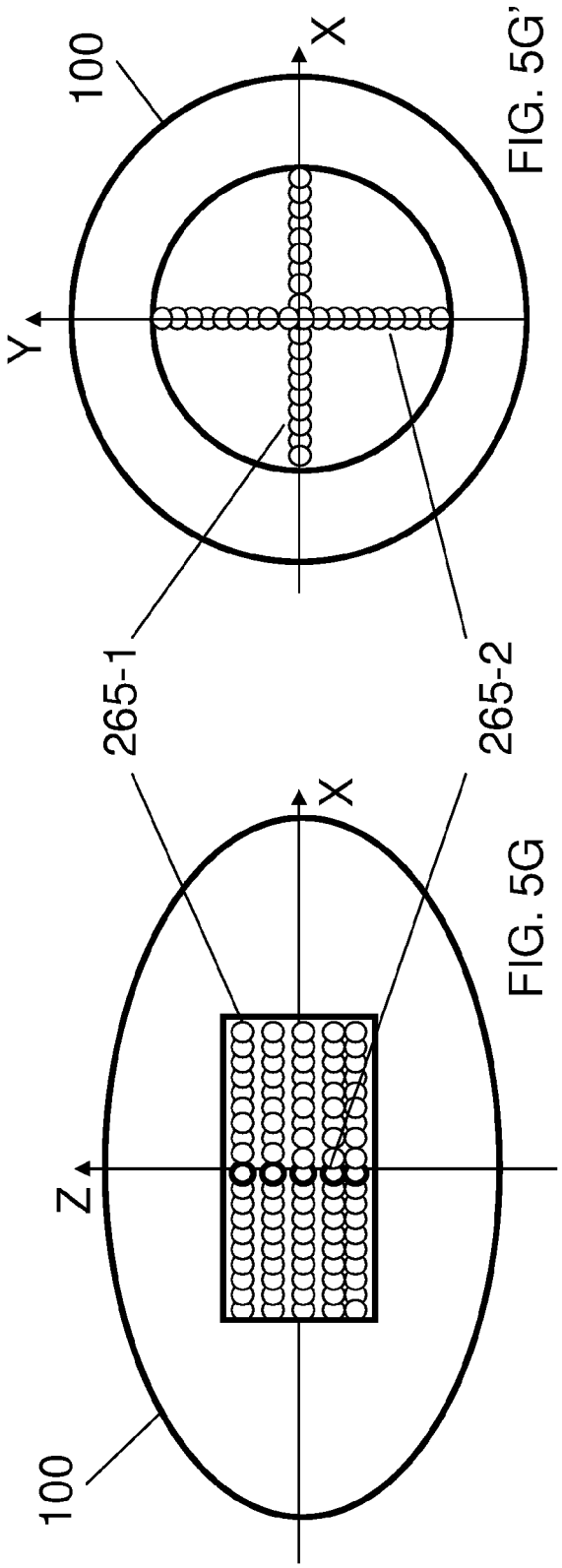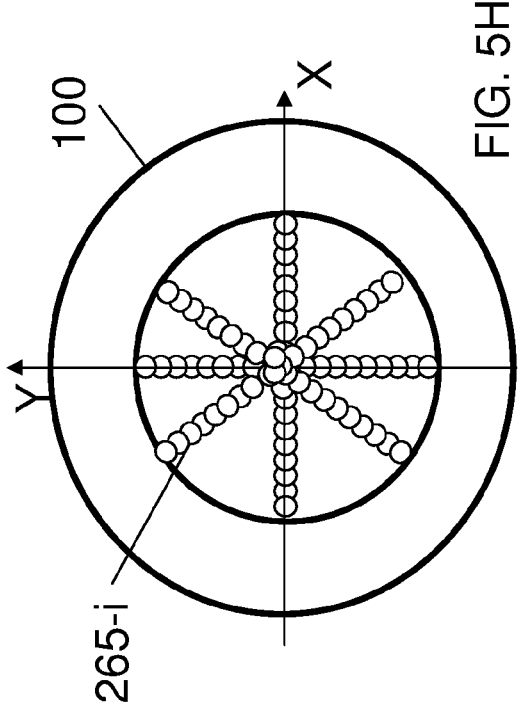

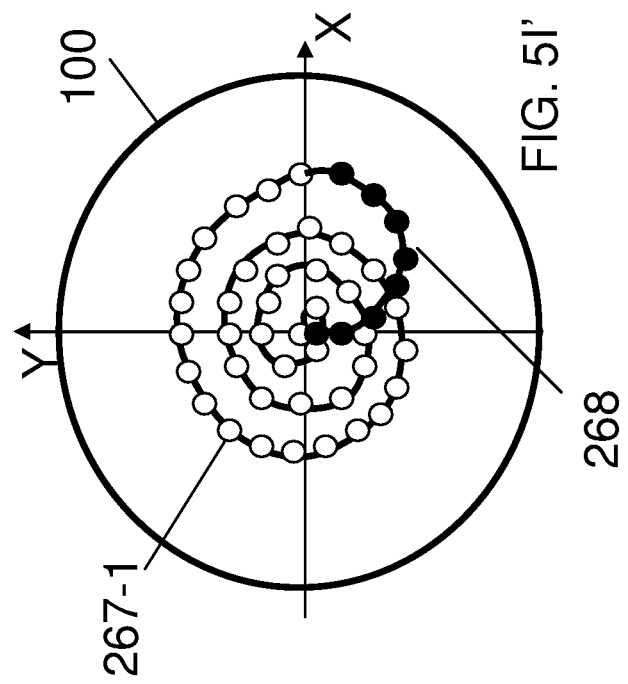
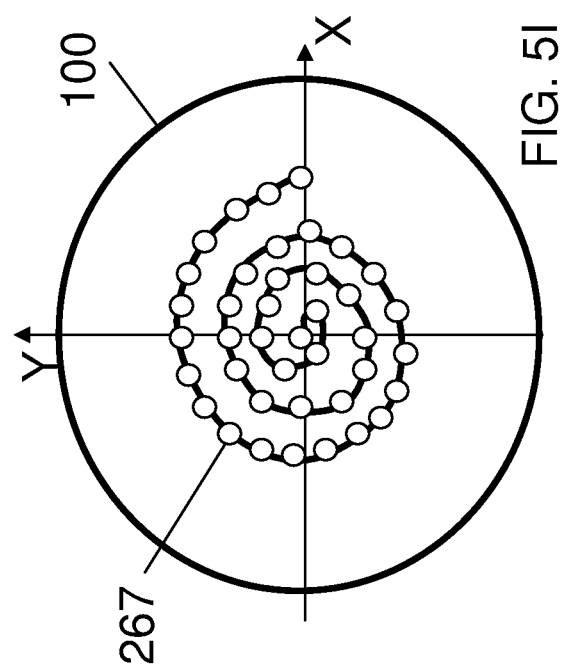

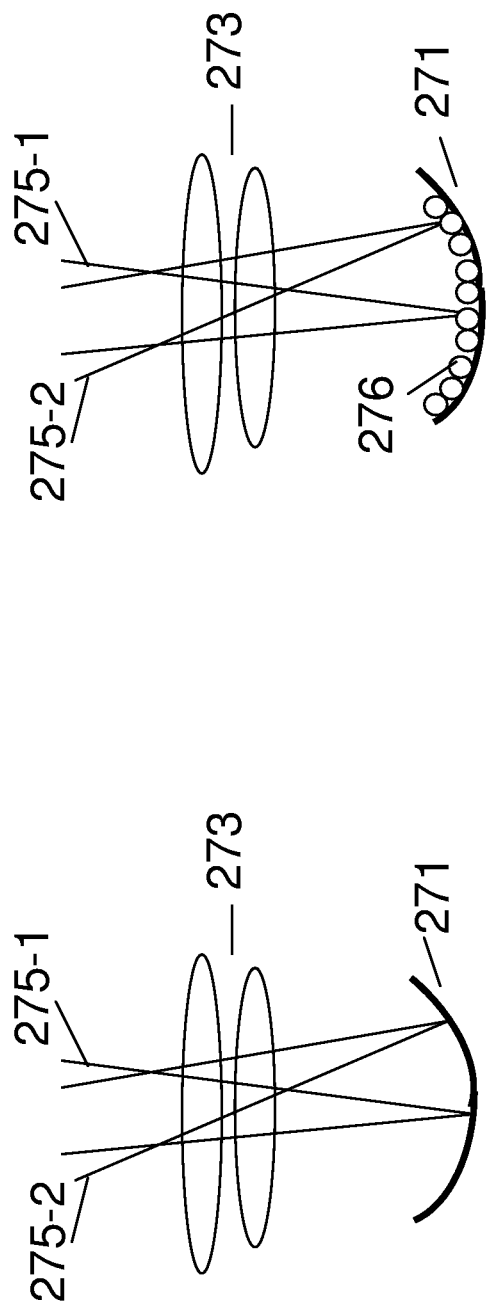

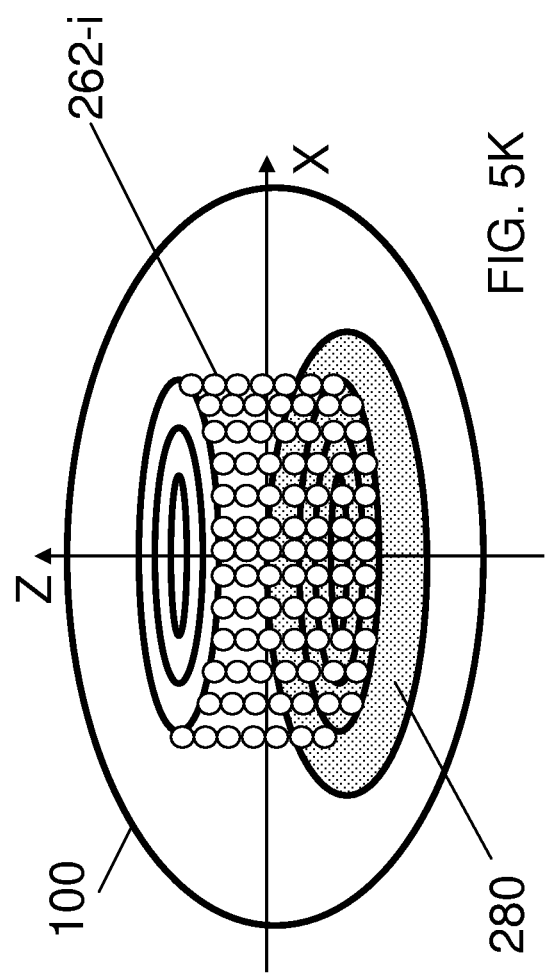

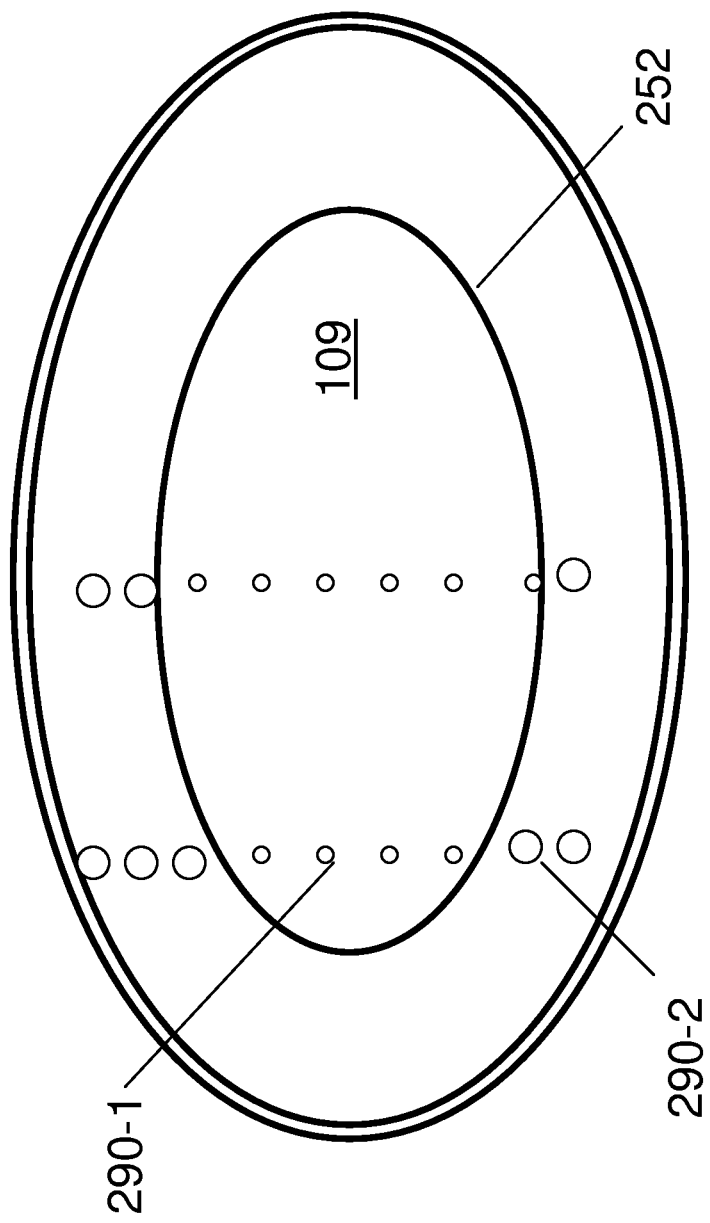

Diagnostic Mode

Surgical Mode

PHOTODISRUPTIVE LASER TREATMENT OF THE CRYSTALLINE LENS

CROSS-REFERENCE TO RELATED APPLICATION

This application is a continuation-in-part of U.S. patent application Ser. No. 12/205,842, filed Sep. 5, 2008, now abandoned entitled "Photodisruptive Laser Treatment of the Crystalline Lens" and filed by Ronald M. Kurtz, which claims priority to and benefit of U.S. provisional application Ser. No. 60/970,454, filed Sep. 6, 2007, entitled "Photodisruptive Laser Treatment of the Crystalline Lens" and filed by Ronald M. Kurtz. The entire disclosures of the above two applications are incorporated by reference as part of the disclosure of this application.

BACKGROUND

This application relates to laser eye surgery of the crystalline lens using photodisruption caused by laser pulses.

Surgical procedures for removal of the crystalline lens utilize various techniques to break up the lens into small fragments that can be removed from the eye through incisions. Some of these procedures use manual instruments, ultrasound, heated fluids or lasers. One of the significant drawbacks of these methods is the need to actually enter the eye with probes in order to accomplish the fragmentation. This typically requires making large incisions on the lens and limits the precision associated with such lens fragmentation techniques.

Photodisruptive laser technology can deliver laser pulses into the lens to optically fragment the lens without insertion of a probe and thus is potentially a less intrusive procedure, offering higher precision and control.

Laser-induced photodisruption has been already used in the past in laser ophthalmic surgery. In the target region the laser ionizes a portion of the molecules, eventually releasing gases, which, in an expansion phase, disrupt and break up the lens material in the target region. In some cases Nd:YAG lasers have been employed as the laser sources.

Lens fragmentation via laser-induced photodisruption has also been proposed. For example, L'Esperance in U.S. Pat. No. 4,538,608 disclosed an apparatus for lens tissue destruction which included a viewing system, a laser and a means for optical delivery and scanning of the focal spot of laser pulses. The laser pulses were focused on the anterior plane of the lens and were moved progressively deeper into the lens to achieve cataract material destruction. In U.S. Pat. No. 5,246,435, Bille proposed an alternative approach that focused the laser pulses first in a posterior region of the lens and then move the focus in a posterior to anterior direction. In this method the laser reached the target regions with less distortion from the already treated regions, thus affording greater control. However, various technical problems remain unresolved.

SUMMARY

Apparatus and methods of treating a hard lens region of an eye with a laser are provided. Implementations of a method of treating a crystalline lens of an eye with a laser include selecting a surgical region of the lens, applying laser pulses to form at least one incision within the selected surgical region, wherein an orientation of the incision is one of an orientation intersecting fibers of the lens and an orientation non-transverse to an axis of the eye, and the incision modifies a property of the lens.

In some implementations the non-transverse orientation of the incision is an orientation substantially parallel to the axis of the eye or an orientation making a less than 90 degree angle with the axis of the eye.

In some implementations a spatial extent of the incision along the axis of the eye is longer than the spatial extent transverse to the axis of the eye.

In some implementations the spatial extent along the axis of the eye is in the range of 0.5 mm-12 mm and the spatial extent transverse to the axis of the eye is in the range of 1-500 microns. In some implementations the axis of the eye is one of a visual axis, an optic axis, a line of sight and a pupillary axis.

In some implementations the incision cuts the fibers into parts approximately at the intersection of the incision and the fibers and the modified property of the lens is a weakening of a biomechanical property of the lens.

In some implementations the incision cuts the fibers at or near sutures of the fibers.

In some implementations the incision avoids cutting sutures in the lens.

In some implementations the applying laser pulses includes applying the laser pulses to generate gas bubbles which form the incision, wherein an orientation of the incision is aligned with a preferential direction of expansion of the generated gas bubbles.

In some implementations the applying the laser pulses includes moving the focal point of the applied laser beam along a posterior to anterior direction within the lens.

In some implementations the incision has one of an extent at least equal to an extent of a nucleus of the lens, an X-Y diameter in excess of 2 mm and a Z extent in excess of 0.5 mm, and an X-Y diameter in excess of 4 mm and a Z extent in excess of 1 mm, wherein the X-Y diameter is a measure of the spatial extent of the entire incision in the direction transverse to the axis.

In some implementations the method includes forming no more than one incision and the laser pulses are applied in a continuous manner to form the incision without repositioning the laser or interrupting the application of the laser.

In some implementations the incision has a form aligned with the axis of the eye, the form being of at least one of a cylinder, a set of concentric cylinders, a set of cylinders connected by one or more connecting line, a curved surface, a cone, a spiral, a layered spiral with smooth lines connecting layers of the spiral and a tilted cylinder.

In some implementations the incision has a form aligned with the axis of the eye, the form being at least one of a plane, two or more crossing planes, a combination of planes and connecting arcs, and a combination of planes and cylinders.

In some implementations the applying the laser pulses includes forming incisions in a layer-by layer manner.

In some implementations the forming the incisions in a layer-by-layer manner includes applying laser pulses to target locations within a posterior layer of the lens, the target locations belonging to two incisions or two segments of the same incision and applying laser pulses to target locations within a layer anterior to the posterior layer, the target locations belonging to the same two incisions or to the same two segments of the same incision.

In some implementations the applying the laser pulses includes applying the laser pulses to form a first ring with a first radius in a posterior layer of the lens, applying the laser pulses to form a connector line between the first and a second ring in the posterior layer, applying the laser pulses to form the second ring with a second radius in the posterior layer, and repeating multiple times the formation of the first ring, the second ring and the connector line in layers sequentially anterior to the posterior layer, wherein the first rings in the sequential layers form a first cylinder, the second rings form a second cylinder, the cylinders being connected by the connector lines.

In some implementations the connector lines in sequential layers are one of aligned to form connector planes and not-aligned from layer to layer.

Some implementations include forming a posterior spiral in a posterior layer, forming a smooth connector line starting near an end of the spiral in the posterior layer, the connector line smoothly bending and rising to a central region of a layer anterior to the posterior layer and forming an anterior spiral starting at the end of the smooth connector line in the central region of the anterior layer.

In some implementations the posterior spiral and the anterior spiral are essentially aligned to form a spiral with an extent in the Z direction.

In some implementations the applying the laser pulses includes selecting laser-parameters sufficient to create bubbles in the lens, but insufficient to cause harm to a retina of the eye.

In some implementations the applying the laser pulses includes applying the laser pulses with laser-parameters insufficient to fragment the lens to a degree suitable for removal, if the incision were transverse to the axis of the eye.

In some implementations the laser-parameters include a laser pulse energy in the range of 0.5 microJ to 50 microJ, a duration of a laser pulse in the range of 0.005 picoseconds to 25 picoseconds, a repetition rate of applying laser pulses in the range of 1 kHz to 10 MHz, and a separation distance of target regions of laser pulses in the range of 1 micron to 100 microns.

In some implementations the applying the laser pulses includes applying the laser pulses with varying energy as the incision is formed.

In some implementations the energy is varied during at least one of a Z directional scanning and an X-Y directional scanning.

In some implementations the energy is varied in relation to a measurement of an optical property of an eye tissue.

Some implementations include forming the incision on a layer-by-layer basis, wherein one or more layers are at least partially formed along a curved focal plane of a laser delivery system.

In some implementations a Z directional scanner is adjusted at a slower rate than an X-Y directional scanner when forming a layer of one or more incisions.

Some implementations further include forming a protection layer in a posterior portion of the lens, positioned to block a large portion of the laser pulses applied to form the incision.

In some implementations the incision fragments at least a portion of the lens, the method further including removing the fragmented portion of the lens.

In some implementations the applying the laser pulses includes applying laser pulses with laser parameters which do not cause lasting damage to a retina of the eye, wherein the laser pulses fragment the lens to a degree suitable for removal and the time of the fragmentation is less than a minute.

Some implementations include applying laser pulses to form an incision in a lens of an eye, wherein the laser pulses are applied by a laser system which is configured to scan the laser pulses in the entire nucleus of the lens without interrupting the application of the laser pulses.

In some implementations the incision intersects fibers of the lens.

In some implementations at least segments of the incision are essentially non-transverse to an axis of the eye.

In some implementations the incision is one of a cylinder, a set of concentric cylinders, a set of concentric cylinders connected by connecting lines, a cone, crossing planes, crossing planes connected by arcs, a spiral, and a layered spiral with a smooth line connecting layers of the spiral.

Some implementations include a laser system for fragmenting a crystalline lens of an eye, including a pulsed laser configured to generate a laser beam of laser pulses and an optical delivery system, wherein the optical delivery system is configured to apply the laser beam to create an incision in the lens of the eye with a spatial extent along an axis of the eye longer than 2 mm and a spatial diameter transverse to the axis of the eye larger than 4 mm without interrupting the application of the laser.

In some implementations the optical delivery system is configured to move a focal point of the laser in a posterior to anterior direction of the lens.

In some implementations the optical delivery system is configured to control the laser to generate a laser beam with laser-parameters sufficient to create photodisruption in a selected lens region and insufficient to cause damage to a retina of the eye.

In some implementations the optical delivery system is configured to control the pulsed laser to generate laser pulses with laser-parameters an energy in the range of approximately 0.5 microJ to 50 microJ, a separation of adjacent target areas in the range of approximately 1 micron to 100 microns, a duration in the range of approximately 0.005 picoseconds to 25 picoseconds and a repetition rate in the range of 1 kHz to 10 MHz.

BRIEF DESCRIPTION OF FIGURES

FIG. 2 illustrates a structure of a lens of an eye, including a reduced transparency region.

FIG. 4 illustrates the steps of a photodisruptive treatment of a lens.

FIGS. 5A-C illustrate the steps of a photodisruptive procedure.

FIGS. 5D-K illustrate various configurations of incisions.

FIG. 6 illustrates a step of determining a boundary of the hard lens region.

DETAILED DESCRIPTION

Figure 1:
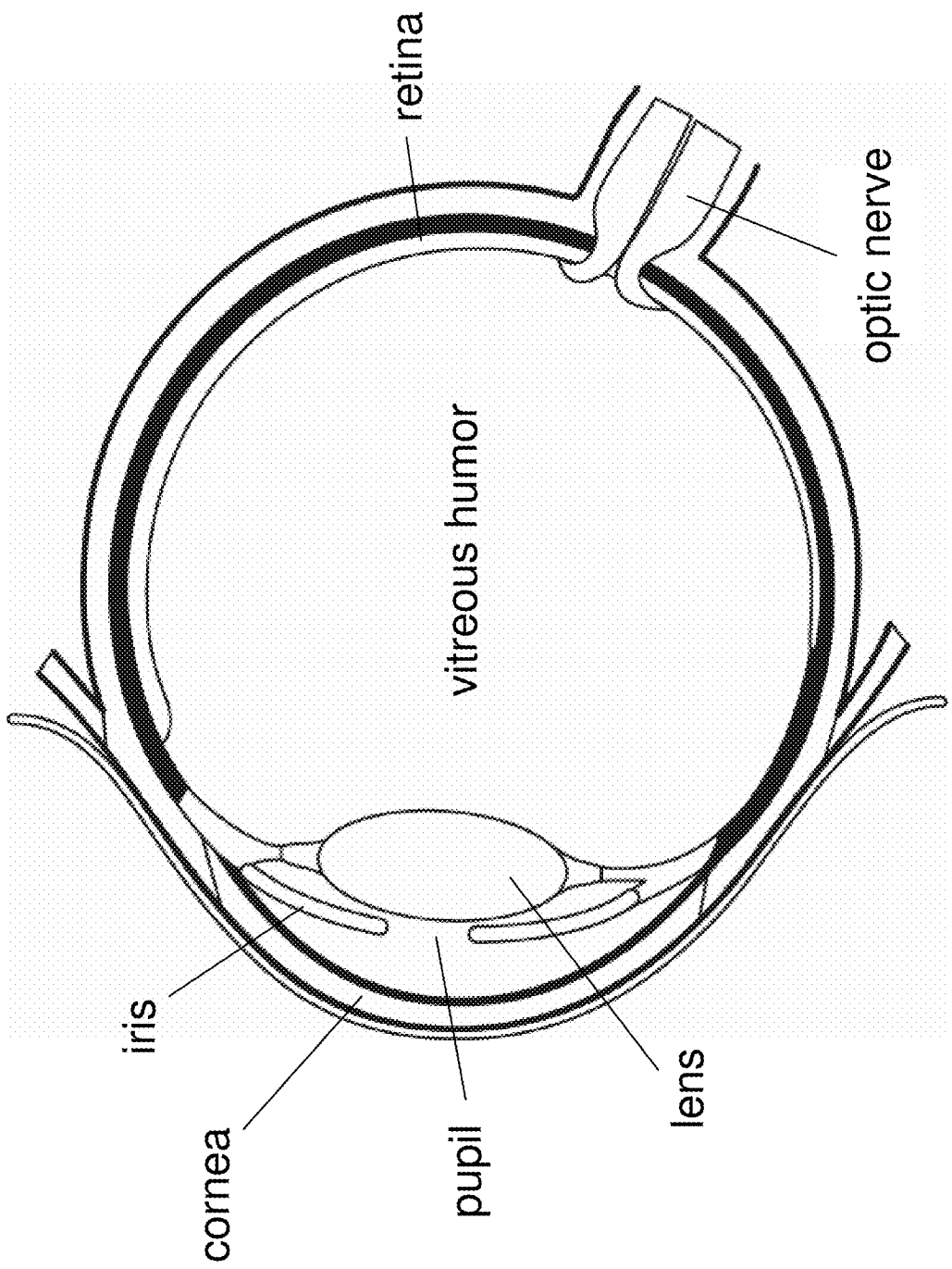
FIG. 1 illustrates an overview of an eye.

FIG. 1 illustrates the overall structure of the eye. The incident light propagates through the optical path which includes the cornea, the anterior chamber, the pupil, the posterior chamber, the lens and the vitreous humor. These optical elements guide the light on the retina.

FIG. 2 illustrates a lens 100 in more detail. The lens 100 is sometimes referred to as crystalline lens because of the $\alpha$, $\beta$, and $\gamma$ crystalline proteins which make up about 90% of the lens. The crystalline lens has multiple optical functions in the eye, including its dynamic focusing capability. The lens is a unique tissue of the human body in that it continues to grow in size during gestation, after birth and throughout life. The lens grows by developing new lens fiber cells starting from the germinal center located on the equatorial periphery of the lens. The lens fibers are long, thin, transparent cells, with diameters typically between 4-7 microns and lengths of up to 12 mm. The oldest lens fibers are located centrally within the lens, forming the nucleus. The nucleus 101 can be further subdivided into embryonic, fetal and adult nuclear zones. The new growth around the nucleus 101, referred to as cortex 103, develops in concentric ellipsoid layers, regions, or zones. Because the nucleus 101 and the cortex 103 are formed at different stages of the human development, their optical properties are distinct. While the lens increases in diameter over time, it may also undergo compaction so that the properties of the nucleus 101 and the surrounding cortex 103 may become even more different (Freel et al, BMC Opthalmology 2003, vol. 3, p. 1).

As a result of this complex growth process, a typical lens 100 includes a harder nucleus 101 with an axial extent of about 2 mm, surrounded by a softer cortex 103 of axial width of 1-2 mm, contained by a much thinner capsule membrane 105, of typical width of about 20 microns. These values may change from person to person to a considerable degree.

Lens fiber cells undergo progressive loss of cytoplasmic elements with the passage of time. Since no blood veins or lymphatics reach the lens to supply its inner zone, with advancing age the optical clarity, flexibility and other functional properties of the lens sometimes deteriorate.

FIG. 2 illustrates, that in some circumstances, including long-term ultraviolet exposure, exposure to radiation in general, denaturation of lens proteins, secondary effects of diseases such as diabetes, hypertension and advanced age, a region of the nucleus 101 can become a reduced transparency region 107. The reduced transparency region 107 is usually a centrally located region of the lens (Sweeney et al Exp. Eye res, 1998, vol. 67, p. 587-95). This progressive loss of transparency often correlates with the development of the most common type of cataract in the same region, as well as with an increase of lens stiffness. This process may occur with advancing age in a gradual fashion from the peripheral to the central portion of the lens (Heys et al Molecular Vision 2004, vol. 10, p. 956-63). One result of such changes is the development of presbyopia and cataract that increase in severity and incidence with age.

The reduced transparency region 107 can be removed via cataract surgery. A common procedure is to make an incision into the capsule of the cloudy lens (capsulotomy) and surgically remove the interior, i.e. the cortex and the nucleus, while leaving the lens capsule intact. This is the so-called extra capsular surgery. While the cortex exhibits viscous fluid dynamics and thus can be removed by aspiration or even simple suction, the nucleus is too hard for this approach and is typically removed as a whole. Finally, a plastic "intraocular" lens is often inserted as a replacement into the capsule. This procedure requires making a quite large incision, sometimes up to 12 mm. Creating incisions of this size can lead to a variety of problems, as described below.

In some methods, the use of ultrasound waves was introduced into cataract surgery. In this "phacoemulsification" procedure one or more smaller incisions are made on the capsule 105 and an ultrasound agitator, or "phaco-probe" is introduced into the lens. Operating the agitator or phaco-probe emulsifies the nucleus, which allows the removal of the emulsified nucleus via aspiration through an incision smaller than the previous technique.

However, even the phacoemulsification technique requires making an incision on the capsule 105, sometimes up to 7 mm. The procedure can leave extensive unintended modifications in its wake: the treated eye can exhibit extensive stigmatism and a residual or secondary refractive or other error. This latter often necessitates a follow-up refractive or other surgery or device.

In recent developments, considerable effort was focused on developing a large variety of the intraocular lenses for insertion into the capsule 105. The examples include even bifocal lenses. However, there wasn't much progress in the area of improving the removal process involving the lens 100 or the nucleus 101.

Implementations of the present application include photodisruptive methods instead of phacoemulsification to break up a hard lens region 109. Since no phaco probe is inserted into the lens 100, a much smaller incision is necessitated only for the subsequent aspiration of the broken-up nucleus. This reduces the unintended secondary effects, and can reduce the percentage of patients who need secondary refractive or other surgery.

The hard lens region 109 often coincides with the nucleus 101. However, numerous variations may occur. E.g. the outermost soft layers of the nucleus may be removable by aspiration or even suction and thus may not require photodisruptive methods. In other cases, only the cataract-impacted portion of the eye may be disrupted for subsequent removal. In yet other cases it may be desired that only a portion of the nucleus 101 is disrupted, when the nucleus is only sculpted and not removed. To express the broader scope of the contemplated variations, all these regions will be jointly referred to as the hard lens region 109. The nucleus 101 is only one embodiment of the hard lens region 109.

In some cases this hard lens region 109 may occupy an ellipsoid-like region of approximately 6-8 mm in equatorial diameter and approximately 2-3.5 mm in axial diameter, or extent. The size of this hard lens region 109 may be different for different patients, for different diseases and for different procedures.

In a laser-induced lens fragmentation process, laser pulses ionize a portion of the molecules in the target region. This may lead to an avalanche of secondary ionization processes above a "plasma threshold". In many surgical procedures a large amount of energy is transferred to the target region in short bursts. These concentrated energy pulses may gasify the ionized region, leading to the formation of cavitation bubbles. These bubbles may form with a diameter of a few microns and expand with supersonic speeds to 50-100 microns. As the expansion of the bubbles decelerates to subsonic speeds, they may induce shockwaves in the surrounding tissue, causing secondary disruption.

Both the bubbles themselves and the induced shockwaves carry out a goal of the procedure: the disruption, fragmentation or emulsification of the targeted hard lens region 109 without having made an incision on the capsule 105. The disrupted hard lens region 109 can then be removed through a much smaller incision, possibly without inserting a surgical device into the lens itself.

However, the photodisruption decreases the transparency of the affected region. Remarkably, the lens of the eye has the highest density of proteins of all tissues, yet it is transparent. For this same reason, however, the transparency of the lens is particularly sensitive to structural changes, including the presence of bubbles and damage by shockwaves.

If the application of the laser pulses starts with focusing them in the frontal or anterior region of the lens and then the focus is moved deeper towards the posterior region, the cavitation bubbles and the accompanying reduced transparency tissue can be in the optical path of the subsequent laser pulses, blocking, attenuating or scattering them. This may diminish the precision and control of the application of the subsequent laser pulses, as well as reduce the energy pulse actually delivered to the deeper posterior regions of the lens. Therefore, the efficiency of laser-based eye surgical procedures can be enhanced by methods in which the bubbles generated by the early laser pulses do not block the optical path of the subsequent laser pulses.

Various approaches, including the technique of U.S. Pat. No. 5,246,435, do not provide an effective way of addressing the above adverse interference by bubbles produced by preceding laser pulses. Thus, prior methods often require the use of additional lens fragmentation techniques in addition to the photodisruption by laser.

In recognition of the above technical problem and based on the investigation of the distinct properties of the various lens regions and the laser pulse parameters on the generation and spreading of cavitation bubbles, the techniques, apparatus and systems described in this application can be used to effectively fragment the crystalline lens by laser pulses with reduced interference from the bubbles induced by preceding laser pulses. Subsequently, the removal of a portion of or the entirety of the crystalline lens can be achieved via aspiration with reduced or no need of other lens fragmentation or modification techniques.

FIG. 3 illustrates that the hard lens region 109 with different transport, optical and biomechanical properties has significant implications for the photodisruptive fragmentation techniques. One significant limitation of the various laser-based lens fragmentation techniques is the hard-to-control spread of gas bubbles that may occur during the photodisruption that can reduce the effectiveness of the subsequent laser pulses to carry out their intended function.

Figure 3B:
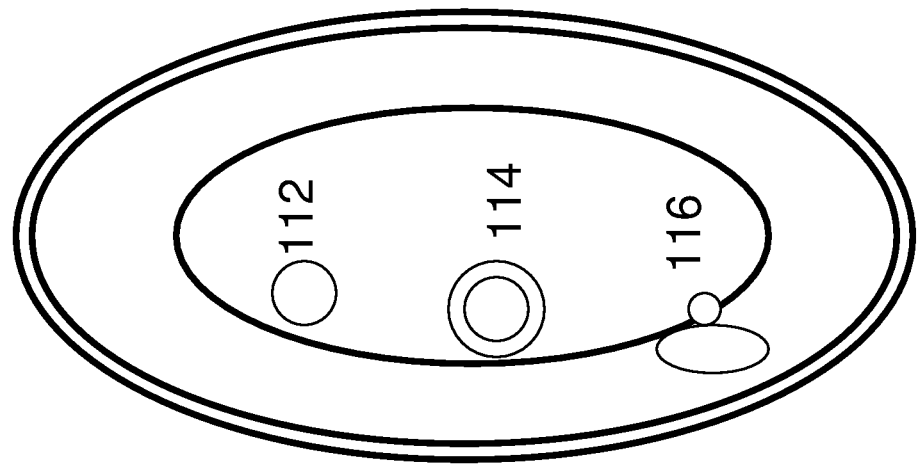
FIGS. 3A-B illustrate the generation and spreading of bubbles in a photodisruptive treatment of a lens.
Figure 3A:
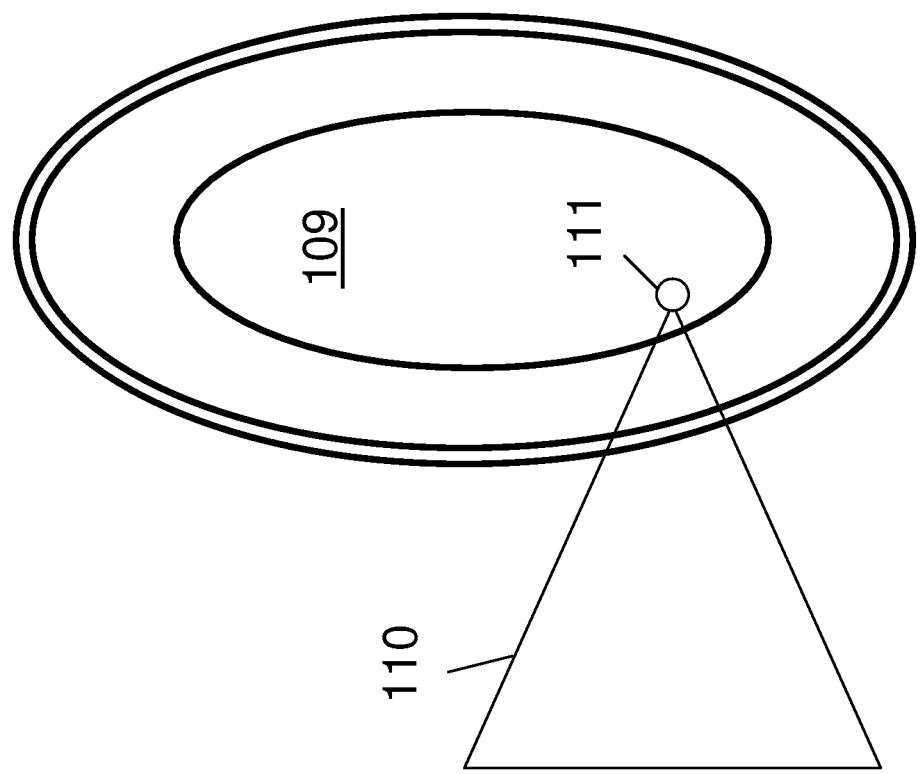

FIG. 3A illustrates that a laser beam 110, which is focused to a small focal or target area can generate a small gas bubble 111.

FIG. 3B illustrates that the resistance against the spread of this cavitation bubble 111 can vary from layer to layer of the lens 100. Inside the nucleus 101, the small bubble 111 may simply expand into a bigger bubble 112. It may also generate shockwaves around the bubble, as shown at 114. Moreover, if the expanding bubble reaches the nucleus-cortex boundary, as bubble 116 does, then the gas can expand extensively in the softer cortex region 103. Any of these extended gaseous bubbles can disturb, absorb, scatter or even block the subsequent laser pulses, directed to fragment the hard lens region.

In addition, there may be pre-existing channels in the hard lens region that may allow the generated gas to move into the softer lens regions and interfere with further pulse delivery. Such channels may be located along suture lines, where lens fibers meet. Avoidance of these and adjacent areas may also be employed to reduce gas spread. In addition, pulse properties may be modified in these areas to further reduce gas spread. Such areas can be identified preoperatively or alternatively, intra-operative identification of such channels can allow the procedure to be altered.

Methods, which first attempt to remove the softer peripheral layers, including the cortex 103 and attempt to remove the harder nucleus 101 afterwards, face considerable drawbacks, because the initial removal of the peripheral layers may leave behind a disrupted, unclear optical path, making the subsequent fragmentation of the harder nucleus 101 by lasers difficult.

It is noteworthy that laser-disruption techniques developed for other areas of the eye, such as the cornea, cannot be practiced on the lens without substantial modification. One reason for this is that the cornea is a highly layered structure, inhibiting the spread and movement of bubbles very efficiently. Thus, the spread of bubbles poses qualitatively lesser challenges in the cornea than in the softer layers of the lens including the nucleus itself.

The resistance of the various lens regions against the spreading of the gas bubbles 111 depends on numerous individual characteristics of each patient including the age of the patient. The spread of gas can also be influenced by the particular laser parameters applied to the target.

FIG. 4 illustrates an implementation of a photo-disruptive eye-surgical process 200 developed from the above considerations.

FIGS. 5A-K illustrate various embodiments of the method of FIG. 4.

In step 210 a boundary 252 of the hard lens region 109 may be determined from measuring a mechanical or optical characteristic of the lens 100. Implementations may include this step 210 because if the laser pulses are applied outside the hard lens region 109, the generated bubbles may expand considerably and in a hard-to-control manner. Therefore, some implementations may include first a determination of the boundary of the hard lens region 109 so that the laser pulses can be focused inside the hard lens region 109.

FIG. 6 shows an implementation of step 210 based on mechanical characteristics of the bubbles. A string of probe-bubbles 290 may be generated in the lens 100, for example, substantially parallel with a main axis of the eye, separated by a suitable distance, such as 10 to 100 microns. Other bubble strings can be generated in other areas of the lens. As shown, since the harder nucleus 101 shows more resistance against the expansion of the probe-bubbles, the probe-bubbles 290-1 inside the hard nucleus 101 may expand slower. By the same token, the cortex 103 may exert less resistance against the expansion of the bubbles and thus the probe-bubbles 290-2 outside the nucleus 101, in the cortex 103 may expand faster. A portion of the boundary 252 between the nucleus 101 and the cortex 103 can then be identified as the line or region separating slow-expanding probe-bubbles 290-1 from fast-expanding probe-bubbles 290-2.

The expansion of the probe-bubbles 290 and the line separating the slow-expanding probe-bubbles 290-1 from the fast-expanding probe-bubbles 290-2 may be observed and tracked by an optical observation method. Many such methods are known, including all kinds of imaging techniques. Mapping out or otherwise recording these separation points or lines can be used to establish the boundary 252 between the softer lens regions and the hard lens region 109. This implementation of step 210 can be pre-operative, i.e. performed prior to the surgical procedure, or intra-operative, i.e. performed as an early phase of the surgical procedure.

Several other methods can be applied for step 210 as well. For example, optical or structural measurements can be performed prior to the surgical procedure on the patient. Or, some database can be used, which correlates some other measureable characteristic of the eye to the size of the nucleus, e.g. using an age-dependent algorithm. In some cases an explicit calculation can be employed as well. In some cases even data from cadavers can be utilized. It is also possible to generate the above bubble string, and then apply an ultrasound agitation, and observe the induced oscillation of the bubbles, especially their frequency. From these observations, the hardness of the surrounding tissue can be inferred as well.

In some cases the method of Optical Coherence Tomography (OCT) can be utilized in step 210. Among other aspects, OCT can measure the opacity of the imaged tissue. From this measurement, the size of the bubbles and the hardness of the region can be inferred once again.

Finally, the hard lens region 109 can be selected based on some other consideration, e.g. when only the cataract region is to be removed, or the nucleus is to be sculpted only. All of these methods are within the scope of step 210 of FIG. 4, and are illustrated in FIG. 5A with the dotted line indicating the boundary 252 of the hard lens region 109.

FIG. 4 illustrates that step 220 may include selecting a laser parameter between a disruption-threshold and a spread-threshold. The laser parameters of the laser pulses 110 can be selected to be above the disruption-threshold for generating the photodisruption in the hard lens region 109. The laser parameters can be selected to be below the spread-threshold that creates uncontrolled spreading of the gas produced by the photodisruption.

These disruption- and spread-thresholds can be demonstrated e.g. in the case of the spatial separation between two adjacent target points of the laser pulses. If the generated bubbles are closer than a lower spread-threshold distance, then the bubbles may coalesce, forming a bigger bubble. These larger bubbles are likely to expand faster and in a harder-to-control manner. On the other hand, if the bubbles are farther than the upper disruption-threshold, then they may not achieve the intended photodisruption or fragmentation of the target tissue. In some cases the range of bubble separation between these thresholds can be between 1 micron and 50 microns.

The duration of the laser pulses may also have analogous disruption- and spread-thresholds. In some implementations the duration may vary in the range of 0.01 picoseconds to 50 picoseconds. In some patients particular results were achieved in the pulse duration range of 100 femtoseconds to 2 picoseconds. In some implementations, the laser energy per pulse can vary between the thresholds of 1 microJ and 25 microJ. The laser pulse repetition rate can vary between the thresholds of 10 kHz and 100 MHz.

The energy, target separation, duration and repeat frequency of the laser pulses can also be selected based on a preoperative measurement of lens optical or structural properties. Alternatively, the selection of the laser energy and the target separation can be based on a preoperative measurement of the overall lens dimensions and the use of an age-dependant algorithm, calculations, cadaver measurements, or databases.

FIG. 4 illustrates that in step 230 a mechanical property of a posterior portion of the hard lens region can be modified in the proximity of the identified boundary 252 by a photodisruptive procedure.

FIG. 5B illustrates an embodiment of step 230, where a set of bubbles is generated by initial laser pulses 110-1 in a posterior portion 254 of the hard lens region 109, in the proximity of the boundary 252. The modifying the mechanical property may include that the generated bubbles photodisrupt, fragment, or even emulsify the tissue of the posterior portion 254 of the nucleus 101, thus modifying some of its mechanical properties.

FIG. 4 illustrates that in step 240 a mechanical property of a portion anterior to the already modified posterior portion can be modified by a photodisruptive procedure.

FIG. 5C illustrates an embodiment of step 240, where a second set of bubbles are generated by subsequent laser pulses 110-2 in a region 256 which is anterior to the already modified region 254.

In implementations of the method these photodisruptive steps 240 can be repeatedly applied by moving the focal or target region of the laser beam 110 along a direction from the posterior of the hard lens region 109 to the anterior of the hard lens region 109. This sequence of the photodisruptive steps 240 controls and limits the buildup and spread of bubbles in the optical path of the subsequent laser pulses 110-2. These implementations allow the subsequent laser pulses 110-2 to deliver essentially their entire energy to the target area, allow for better control of the subsequent pulses, as well as clearer imaging of the surgical area for the benefit of the person conducting the procedure.

Steps 210-240 may be followed by the removal of the fragmented, disrupted, emulsified or otherwise modified hard lens regions 109, if required or desired. One method of removing the fragmented, disrupted, or otherwise modified regions is to create one or more small openings, or incisions in the lens capsule 105, and then insert an aspiration probe to remove the fragmented material. In other implementations, simple suction can extract the fragmented material, as well as the non-fragmented viscous material, such as the cortex 103, without inserting a probe into the capsule.

When laser pulses are applied to the hard lens region 109 from the posterior to anterior direction, between the disruption- and the spread-thresholds, they can optically modify, photodisrupt, or fragment the structure of the treated hard lens region 109 to facilitate lens material removal while also reducing the spread of gas and bubbles during placement of these initial and subsequent laser pulses. The characteristics of the hard lens region 109 can vary from patient to patient though, thus the disruption-threshold and spread-threshold laser parameters may need to be determined from patient to patient.

In some implementations, the energy of the laser beam can be adjusted as the focal point is moved in the posteriorto-anterior direction. To reach the anterior layers, the laser beam passes through less material and thus a laser beam with less energy can achieve the same disruption in the target tissue. Accordingly, applying a laser beam with a constant energy may generate an increasing amount of gas as the laser is moved in the anterior direction. To avoid the generation and subsequent spread of such an excess amount of gas, in some implementations the laser energy can be reduced as the laser is moved in the posterior-to-anterior direction. In other implementations, the applied laser energy can also be adjusted as the laser is scanning in the X-Y transverse direction, as the amount of material the laser passes through also varies as the scanning proceeds in the X-Y transverse direction.

In some implementations, the rate of reduction of the applied energy can be calculated from an imaging procedure, which is sensitive e.g. to an optical density or a scattering of the imaged target tissue.

Additional laser pulses can be applied subsequent to the initial laser application, at target positions in the lens outside the initially treated zone in the central region of the lens. The gas and bubbles created by these subsequent laser pulses can either permeate in the treated central region of the lens without uncontrollably spreading in the lens, or can spread into the lens tissue outside the initially treated zone. As such, the gas produced by photodisruption in the peripheral areas of the lens does not block effective treatment of the hard lens region 109. The laser treated hard lens region and the peripheral lens material which may or may not be treated with the laser depending on need can be removed from the eye via aspiration, with or without additional lens tissue breakup using mechanical, suction, ultrasonic, laser, heated fluid or other means. In another implementation, only the treated region is removed via aspiration, with or without additional lens tissue breakup using mechanical, suction, ultrasonic, laser, heated fluid or other means.

FIGS. 5D-K illustrate other implementations of the eye surgical method 200. To set the stage for the description of these methods, a note on terminology. In the following the terminology "an axis of the eye" will be used extensively. There are several ways to define an axis of the eye. The axes of the eye can be categorized e.g. according to the Grand Y. L. Physiological Optics (Springer-Verlag, New York, 1980) as follows:

Optical axis: Line passing through the optical center of the cornea and the lens;

Visual axis: Line passing from the point of fixation to the image on the center of the retina called fovea;

Line of Sight: Line passing from the object point through the center of the entrance of the pupil; and Pupillary axis: Line passing perpendicularly through the center of the cornea and the center of the entrance of the pupil.

In practice these axes are often quite close to each other. Further, compromise axes can be defined as well, e.g. an axis which lies between any two or three of the above axes. In the rest of this disclosure the scope of the term "the axis of the eye" will include any one of these definitions. The axis of the eye will be also referred to as the Z axis. In typical implementations the laser beam can also be oriented along the Z axis. However, other implementations where the laser beam makes an angle with the Z axis are also within the scope of the described method. The two directions transverse to the Z axis will be sometimes termed X and Y axes, following customary terminology.

General aspects of these implementations include the following.

First, these implementations benefit from the recognition that a primary source of the biomechanical strength of the lens is based on its fibers. As described above, the fibers are an elongated, hardened, essentially transparent tissue within the lens, which grow around the center of the eye in a somewhat irregular manner, typically starting from the equatorial plane. The length of fibers can vary widely. In some cases the length falls within the range of 1-10 mm. However, fiber lengths outside this range can also occur. The fibers can be joined at sutures. In various contexts the fiber structure of the lens has been described as layered, as an onion structure and as a ball of yarn. Close to the axis of the eye, the fiber layers are typically oriented in a manner near perpendicular, or transverse, to the axis.

The fiber-rich central region forms the nucleus. Accordingly, to a considerable degree the biomechanical strength of the nucleus is provided by the fibers and their layers, which are near perpendicular/transverse to the axis of the eye.

Second, as described below in more detail, there is an improved understanding of the dynamics and expansion of the laser generated cavitation bubbles which make up the incision, indicating that they expand quite differently parallel and transverse to the fiber layers in the lens. Implementations of the surgical methods exploit these differences to improve the efficiency and control of the surgical process.

Third, these implementations also benefit from the availability of new and improved eye-surgical laser systems, which are capable of scanning a large fraction of the surgical area, in some cases the entire area, without repositioning. As described below, this feature may offer substantial positive aspects.

In the light of the above described three developments, some implementations of the eye surgical method differ from existing methods at least in the following aspects:

(i) The Incisions are Non-Transverse:

Close to the center of the eye incisions maybe positioned and oriented in directions which are non-transverse to the axis of the eye. Accordingly, the extent of the incisions can be long along the Z axis and smaller in the X-Y plane.

In some embodiments, the incisions can be essentially parallel to the axis of the eye. Examples include cylinders, whose axis is essentially parallel to the axis of the eye. In some cases the length of the cylinder can be between 0.5 mm to 12 mm in the Z direction and the extent in the X-Y plane, essentially the thickness of the incision, can be in the range of 0.1-500 microns.

A shared characteristic of some of these embodiments is that the individual incisions or features have a longer spatial extent in the Z direction, or axis-parallel direction, than in the X-Y direction, or transverse direction. In the case of e.g. cylindrical incisions (see below), the length of the cylinder along the Z axis is longer than the thickness of its wall in the X-Y direction. The term "extent in the X-Y direction" will be used to refer to that of the single incision itself, such as its thickness, and not an overall dimension of the geometric form of the incision, e.g. the diameter of a cylinder. In some embodiments, the spatial extent of the incisions in the Z direction can be in the range of 0.5-10 mm, the extent in the X-Y direction, i.e. the X-Y thickness can be in the range of 1-500 microns, and the X-Y diameter of the incision can be in the range of 2-10 mm. The spatial extent of the individual incisions can be chosen depending on the number of parallel incisions and their separation.

Other embodiments can be practiced as well, where the incisions make some angle with the axis of the eye, e.g. in the form of a cone, or a tilted cylinder, or any other form, non-transverse to the axis of the eye. Non-transverse incisions with piece-wise transverse sections are also within the scope of these implementations.

(ii) The Incisions Cut Fibers:

Close to the axis of the eye, because of the non-transverse orientation of the incisions, the incisions cut through some of the fibers of the lens, as the fibers and their layers are typically close to transverse to the axis of the eye. In peripheral areas of the lens the fibers and their layers tilt/bend away from the transverse direction. Accordingly, in these peripheral regions the incisions themselves can be oriented in a direction which still cuts the non-transverse fibers. Since the fibers are a primary source of the biomechanical strength of the lens, cutting through the fibers reduces the biomechanical strength of the lens effectively.

(iii) The Orientation of the Incision Offers Superior Gas Management:

The impact of the laser beam creates miniscule bubbles in the target tissue. Experiments reveal that these bubbles undergo a two stage expansion. During an initial fast expansion, the bubbles may expand at supersonic speeds, and thus can be very efficient at fragmenting/disrupting the surrounding tissue. This fast expansion is typically anisotropic and occurs mostly in the direction of the laser beam, i.e. approximately the Z direction. The second stage of the expansion is slower, and typically occurs towards the softer tissue, i.e. between the fiber layers, in the transverse direction. During this slow transverse expansion, bubbles often coalesce into bigger bubbles, which can obscure the optical path of subsequent laser pulses, considerably undermining the control and efficiency of the procedure.

In existing methods, which create transverse incisions, the fast, Z-directional bubble expansion does not help creating the transverse incision, and therefore the surgeon has to create the bubbles much more closely to each other.

In contrast, in implementations of the present method, creating incisions approximately in the Z direction, the anisotropy of the fast bubble expansion is put to good use, as it allows the surgeon to create fewer bubbles spaced farther apart in the Z direction, since the bubbles will fast expand in the Z direction and fragment the tissue between neighboring bubbles efficiently.

Such a reduction of the necessary number of bubbles or the equivalent reduction of laser energy in the present method is a critical difference, as most of the laser beam, after having left the lens, reaches the retina. The retina, being a photosensitive tissue, may suffer substantial damage because of the impact of this laser beam. To achieve a fast and substantial fragmentation of the lens tissue, the energy of the laser is often chosen to be close to values which can damage the retina. Therefore, the reduction of the necessary number of bubbles or the energy per pulse of the laser in the present method can mean the difference between damaging the retina and leaving it intact.

Furthermore, the present method also offers advantages regarding the second, slower bubble expansion. During this stage the bubbles expand in the transverse direction. As described above, these bubbles, especially when coalescing together, can substantially and disadvantageously obscure the target area, reducing the efficiency and control of the surgical procedure.

In the present method, the surgeon can create the Z-directed incisions layer-by-layer (see FIG. 5F-F'-F"), creating only lines of bubbles in each layer. Therefore, the surgeon can move the focus of the laser faster than the transverse expansion of the previously created bubbles.

In contrast, existing methods create transverse incisions, i.e. the surgeon has to create bubbles covering entire areas, returning repeatedly to regions which have been passed earlier. In these methods it is hard or near impossible for the surgeon to move the laser faster than the expanding bubbles, or to avoid returning to previously impacted areas. In fact the surgeon is regularly forced to operate in the area obscured by the expanding bubbles, leading to a considerable reduction of precision and control over the surgical procedure.

(iv) The Incisions Avoid Sutures in Some Implementations:

As mentioned before, fibers typically come together, or end, in sutures. These sutures often form planar structures, parallel to the Z axis. It has been observed that in some cases bubbles expand particularly fast along sutures. Such a too-fast expansion may result in obscuring or clouding the optical path even if Z directional incisions are formed, thus possibly reducing control and precision. Therefore, some implementations of the method create incisions away from sutures.

At the same time, other implementations may be based on the observation that the sutures provide a structural framework for the fibers, and thus cutting through the sutures may be particularly effective in reducing the biomechanical stability of the lens. This benefit has to be weighed against the above mentioned drawback of fast-expanding bubbles along the sutures. Depending on the comparative cost-benefit analysis and the other requirements of the method, some implementations may avoid making incisions at or near the sutures, while others may cut through some of the sutures.

(v) Making Fewer Incisions Applies Less Energy to the Eye:

Since the fiber-cutting incisions are quite efficient in reducing the biomechanical strength of the lens, a reduced number of incisions are capable of achieving the extent of tissue fragmentation necessary for the objectives of the eye surgery. Reduced number of incisions can be applied in shorter time, thereby applying less energy to the eye. Therefore, these surgical methods deposit a reduced amount of energy in the eye, thus e.g. reducing the potential risk to light sensitive tissue, such as the retina by this method.

In some implementations, an eye surgical method making transverse incisions may require 150-160 seconds to achieve the fragmenting of the lens to the degree which is reached in only 45-50 seconds with methods which make essentially axis-parallel incisions.

This factor of 3-4 reduction of surgery time can be quite beneficial, since often surgical patients develop hard-to-control eye movements after about 120 seconds, necessitating the abandonment of the surgical procedure. The just-described reduction of surgery time can mean the difference between the successful completion of the surgery and its abandonment.

Equivalently, this time reduction can be converted into reducing the energy deposited by the laser by a factor of 3-4 in fiber-cutting methods during comparable surgery times, thereby substantially reducing the potential for damage in the retina.

(vi) Incisions are Few and Extended:

The eye surgical method can be performed with surgical instruments which are configured to create incisions with unprecedented spatial extent. In some implementations of the surgical instrument this extent can be 0.5-10 mm in the Z direction, in some cases 2-4 mm, and 2-8 mm in the X-Y plane. This large spatial extent of the incisions imparts several positive features to the surgical method, as described below.

(vii) Extended Incisions have Fewer Acceleration/Deceleration Regions:

When making an individual incision, at the beginning of the incision the movement of the laser-focal-point typically accelerates from zero to the regular scanning speed. While the laser is accelerating, it may deposit energy at a higher rate or higher density to the eye, possibly leading to damage in the light sensitive tissues, such as the retina. The same applies at the end of incisions, when the laser-focal-point is decelerating, again possibly damaging the retina. Therefore, methods which utilize longer incisions reduce the number of acceleration/deceleration regions, thus reducing the potential for damage to the light sensitive tissues in these regions in contrast to methods which use a large number of minute incisions.

Existing surgical systems are unable to avoid this problem, as their scanning range in the Z and X-Y directions is considerably less than the entire surgical region. In some existing systems the X-Y scanning range can be 1-2 mm and the Z scanning range can be 0.5 mm, which is substantially less than the entire surgical region of the lens, such as the size of the nucleus. Typically, the nucleus has a Z extent of 2-4 mm and an X-Y diameter of 6-10 mm. This limitation of the existing systems requires that the surgeon make a large number of smaller incisions, with lots of acceleration/deceleration regions. Once the laser scanner reaches its maximum range when making an incision, the surgeon has to stop the scanning via a deceleration, then reposition the laser scanner pointing to a new scan-start point and start a new incision with an acceleration region. Thus methods using existing laser surgical systems involve creating a number of acceleration/deceleration regions, with the concomitant problems.

In contrast, implementations of the present method may benefit from the availability of improved laser systems, which can have a considerably extended X-Y scanning range of 2-10 mm and Z range of 0.5-10 mm. Therefore, implementations of the present method may involve making only a few incisions, thus generating only few of the problematic acceleration/deceleration regions.

In particular, some surgical laser systems may be capable of scanning the entire surgical region. With such systems, the lens-surgery may involve creating only one, uninterrupted extended incision, thus having the lowest possible number of acceleration/deceleration regions.

Here it is mentioned that surgical laser systems with larger X-Y scanning ranges have been described before. However, these systems were used for surgery on the cornea. There are crucial differences between lens surgery and cornea surgery, as during lens surgery both the imaging light off the target and the applied laser propagate through optically active regions: the cornea, the antechamber and part of the lens itself. Propagation through these regions deflects the light substantially both because their differing index of refraction as well as their varying curvature. Therefore, considerable corrections and calculations are required by the surgical equipment and its operator to point the laser to its indented target region.

Further, the laser beam needs to be not only pointed but also focused on the target. A convergent beam is, by definition, extended off its focus point, or target. Therefore, prior to reaching the target, different sections of the converging laser beam propagate through regions of the eye with different optical properties and different curvatures, posing a second level of challenges.

In contrast, the cornea is the outermost optically active layer of the eye. Therefore, neither the pointing nor the focusing of the laser beam poses a hard challenge. Further, the problems arising from the curvature of the cornea can be minimized e.g. by applanating it, i.e. making the cornea essentially flat by applying various contact lenses and devices. In contrast, applanating the lens is quite challenging and presently no proposal is available how to achieve this.

Because of all the described hard challenges, corneal surgical laser systems are qualitatively simpler than lens surgical lasers. This is well supported by the fact that even though corneal surgical systems were suggested about 40 years ago, none have been adapted successfully for lens surgery to date.

(viii) Extended Incisions Pose Less Stringent Requirements for Synchronization:

Surgical lasers typically have a beam controller, configured to switch the laser beam on and off, or control the laser via a shutter mechanism. This beam controller is synchronized with the beam scanner as the laser is switched off when the beam scanner reaches its maximum range, or the end of the incision intended by the surgeon. These surgeries require synchronization between the beam scanner, the beam controller and the surgeon's actions. In surgical methods which employ a large number of small incisions, this need for synchronization poses stringent requirements on the beam controller and beam scanner. In contrast, surgical methods which employ few and extended incisions impose considerably less stringent synchronization requirements.

(ix) Extended Incisions have Fewer Transient Laser Fronts:

When the laser is switched on to start a new incision, the initial front of the laser may have transients which are less-well-controlled. These laser fronts may carry a less-well-controlled amount of energy and may be less well focused on the intended target region. Surgical methods using longer incisions and thus employing fewer switch on/off events reduce the number of such less-well-controlled laser fronts and transients, increasing the control over the tissue fragmentation.

(x) Extended Incisions Minimize Z-Scanner Movement:

Minimizing speed and the acceleration of the scanner mechanism along the Z axis is particularly important because the limits of speed and acceleration along the Z axis are more stringent than along the X and Y axes. While scanning in the transverse X-Y direction is achieved in some embodiments by rotating small and light scanning mirrors, Z axis scanning customarily involves translating a lens or a lens group of the delivery system linearly along the optical axis. This lens or lens group is usually heavier than the scanning mirrors and thus has a higher inertia. Therefore, moving this lens or lens group fast can be more difficult than moving the X-Y scanning mirrors. Extended incisions place less demanding requirements on the movement of the Z-scanner.

Aspects (vi) to (x) highlight that eye surgical systems which are capable of scanning the laser beam in a more extended range and thus are capable of making longer incisions without repositioning, offer substantial positive aspects over systems which are capable of shorter incisions only.

In particular, laser scanners which can scan the laser beam across the entire surgical region without interruption or repositioning can avoid most of the deficiencies of prior systems, which require such repositioning, as described in points (vi)-(x).

In some implementations the laser pulses can be applied with laser-parameters which are sufficient to create bubbles in the lens, but insufficient to cause harm to a retina of the eye.

Because of the enhanced efficiency of the incisions in the above described surgical method to weaken the biomechanical properties of the lens, in some implementations the laser pulses can be applied with laser-parameters which would have been insufficient to fragment the lens to a degree suitable for removal, had the pulses been used to form an incision transverse to the axis of the eye.

Laser parameters in various implementations may fall into this "insufficient-to-fragment" range if a laser pulse energy is in the range of 0.5 microJ to 50 microJ, a duration of a laser pulse is in the range of 0.005 picoseconds to 25 picoseconds, a repetition rate of applying laser pulses is in the range of 1 kHz to 10 MHz, and a separation distance of target regions of laser pulses is in the range of 1 micron to 100 microns.

For all the above reasons, laser-formed incisions which are dominantly non-transverse to the visual axis and thus cut through layers of lens fibers, weaken the biomechanical strength of the lens qualitatively more efficiently than incisions which are transverse to the axis and thus cut only few fibers or none at all. Therefore, implementations of this method require considerably less power, shorter application time or lower repetition rate for the surgical laser pulses. Due to this efficiency of these implementations, the treatment times to fragment the lens can be reduced by a factor of 3-4 or more. Further, implementations benefit in a multiplicity of ways from new and improved surgical systems which allow the scanning of the entire surgical region without interruption or repositioning.

FIGS. 5D-K illustrate various implementations of the surgical method. The surgical method may start with the surgeon selecting a surgical region of the eye to be treated. Next, the surgeon may design the procedure by selecting the location of the non-transverse incisions to be made. Then, the surgeon can form non-transverse incisions in the surgical region by the fast and repeated application of laser pulses. During the application of the laser pulses, the focus of the laser pulses can be moved in a posterior to anterior direction so that the previously formed bubbles do not obscure the target region the subsequent laser pulses are to be applied.

FIGS. 5D-K illustrate various incisions in the lens 100, created by various implementation of the surgical method.

FIGS. 5D-D' illustrate dominantly transverse incisions, formed by a large number of bubbles generated in transverse layers. These incisions will also be referred to as transverse incisions. FIG. 5D illustrates the layers of bubbles which make up the transverse layers 260-*i* from the side, highlighting the X-Z plane of the lens. FIG. 5D' illustrates the same from the top, highlighting the X-Y plane.

FIGS. 5E-E' illustrate a dominantly axis-parallel or Z-directional cylindrical incision. FIG. 5E illustrates the bubbles which make up concentric axis-parallel cylinders 262-*i* from the side, highlighting the X-Z plane of the lens. The bubbles are shown only on the outermost cylinder for clarity. FIG. 5E' illustrates the same from the top, highlighting the X-Y plane. While in typical implementations the bubbles are densely packed, the figures show the bubbles only sparsely and on selected cylinders to avoid clutter. As described above, analogous implementations can utilize any related geometrical form which is non-transverse to the optical axis, including incisions of the form of a cone, tilted cylinder, bulging or bending shape. These incisions typically cut through the fibers of the lens.

Figure 5F:
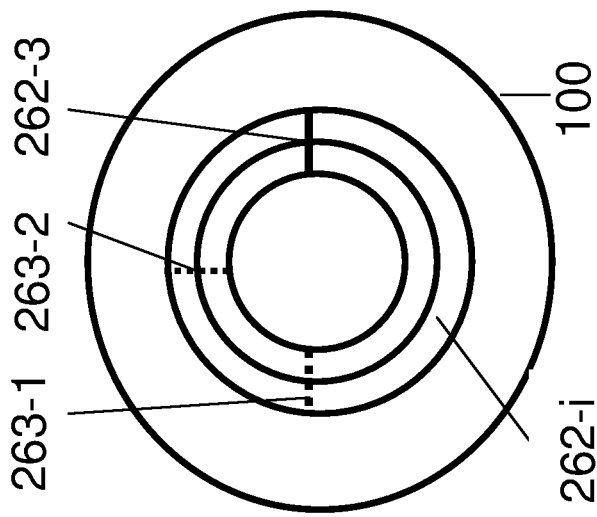
Figure 5F:
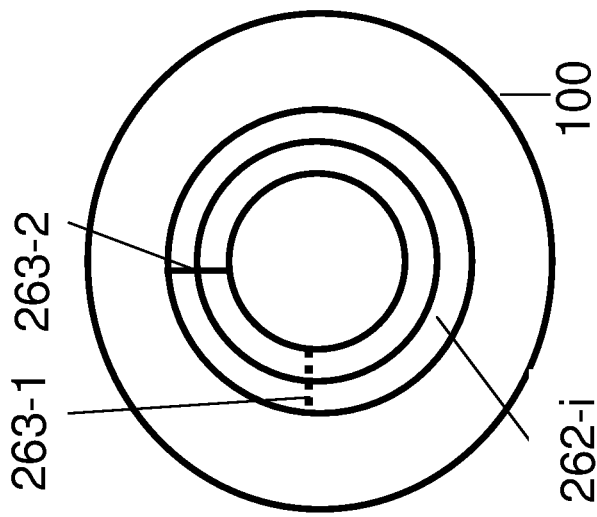
Figure 5F:
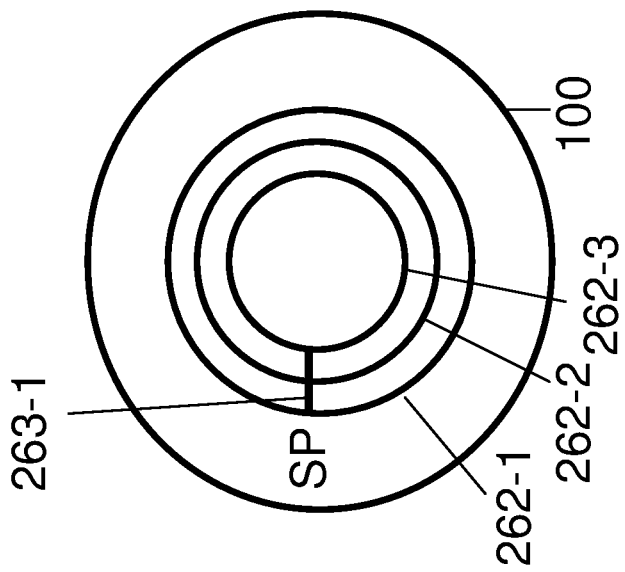

FIGS. 5F-F'-F'' illustrate steps of generating several cylindrical incisions. This particular implementation involves three cylinders, but others may involve any number of cylinders which are capable of achieving the surgical goal, e.g. the photodisruption of the lens.

In some implementations the cylinders are formed layer-by layer simultaneously, i.e. in parallel. These implementations face less of a problem regarding the subsequent laser targeting being hindered by the expansion of the earlier formed bubbles.

To start with, the surgeon may decide the posterior-most depth of the incisions. A guiding principle may be to make sure that the incision is safely within the lens, and therefore the capsule is not accidentally pierced by the method, leading to undesirable consequences.

Then the surgeon may apply laser pulses to form a ring of bubbles with a diameter of e.g. the outermost cylinder 262-1, to form the posterior-most ring of cylinder 262-1. When the laser focal point is moved along the entire ring and arrives back to the starting point SP, the surgeon may move the focus of the laser along connector-line 263-1 towards the center until it reaches the next cylinder 262-2. The focus of the laser is then moved again to form the posterior-most ring of cylinder 262-2. Finally, again using the connector-line 263-1, the posterior-most ring of the innermost cylinder 262-3 is formed the same way.

An aspect of this method is that all these steps were carried out by continuously applying the laser, in effect creating one incision. Therefore, at no time is the surgeon forced to switch off the laser beam, thus avoiding the problems described in points (vi)-(x) above. In other implementations more than one incision is made, but still only a few of them, and not a large number of minute incisions.

Next, the surgeon can move the focus of the laser in a posterior-to-anterior direction, and start forming the second layer of rings of the three cylinders 262-1, . . . 262-3. Thus, layer-by-layer, the three cylinders 262-1, . . . 262-3 can be formed essentially simultaneously.

In the implementation of FIG. 5F, the connector-lines 263 are aligned in different ring-layers.

FIGS. 5F'-5F'' illustrate a different implementation, where the connector lines are not aligned in different layers. Visibly, the connector lines 263-1, . . . , 263-3 in ring layers 1, 2, 3 can be rotated relative to each other. For clarity the connector lines in the lower layers are shown with dotted lines.

These implementations simplify the scanning pattern of the pulses and avoid the need for special measures to block or turn off the laser while moving from one incision to another. In such cases, the effectiveness of the fragmentation by the incisions may be further enhanced by the alternation of the position and/or orientation of the connecting segments.

FIGS. 5G-G' illustrate a Cross Plane embodiment. FIG. 5G illustrates one of the two cross planes 265-1 from the side, highlighting the X-Z plane of the lens. The central column of bubbles shown with bold lines indicates the other of the two cross planes 265-2, pointing out from the X-Z plane.

FIG. 5G' illustrates the same two cross planes 265-1 and 265-2 from the top, highlighting the X-Y plane.

In practice, these two cross planes again can be formed by a layer-by-layer approach, i.e. forming the posterior-most row of bubbles of cross plane 265-1, then move the focal point of the laser along an arc to the starting point of the posterior-most row of the other cross plane 265-2 and form that row. As the cross-planes are being formed layer-by-layer, the arcs can form a cylinder around the cross planes. In this sense, this implementation creates an integrated cross-plane/cylinder structure.

A large number of variations and combinations of the above implementations are possible.

FIG. 5H illustrates that e.g. instead of two cross planes 3, 4, 6, etc cross planes 265-i can be created, forming "slices" or "wedges" of the cylindrical surgical region.

FIG. 5I illustrates a spiral shaped incision 267, where no large angle redirection is involved in the formation of the incision.

FIG. 5I' illustrates a multi-layer spiral incision. In this implementation when a spiral incision 267-1 is completed in a first, posterior layer, the surgeon can move the focal point of the surgical laser to the central starting point of the spiral in a second, anterior layer following a smooth and gently rising connecting line 268, and then start creating the spiral 267-2 in this second anterior layer. This smooth connecting line 268, indicated by the solid dots, can be an approximate semi-circle, or any one of a large number of similarly smooth curves. Such smooth connecting lines reduce the acceleration of the focal point, providing for a more even application of laser energy into the target tissue.

FIGS. 5J-J' illustrate that the focal plane 271 is typically curved in optical systems unless (any suitable portion of) the optics 273 of the laser delivery system is corrected for field curvature. In most uncorrected optical systems the curvature is positive, i.e. the focal length is longer for axial beams 275-1 and shorter for off-axis beams 275-2, as shown in FIG. 5J.

When the intended incision is a straight transverse line or extended transverse planar cut, the servo motor driving the Z-scanner (the "Z servo") can be continuously adjusted in order to compensate the distorting effect of field curvature. However, since the transverse X-Y scanning speed may be much higher than the Z scanning speed because of the higher inertia associated with the Z scanning, the Z servo may not be able to adjust the focus of the laser beam in the Z direction at the high speed of the X-Y scanner.

FIG. 5J' illustrates an implementation which does not require adjusting the Z-scanner at the X-Y transverse scanning rate. In this implementation an incision 276 is formed which follows the curvature of the focal plane 271 of the laser delivery optics 273. The incision 276 can be any of the previously described non-transverse lines, non-transverse planar cuts, layers of spirals, nested cylinders or crossed planes. When any of these implementations are formed on a layer-by-layer basis, the incisions in several or all of the layers may follow the curvature of the focal plane 271, thus reducing or eliminating the need to move the Z servo at the rate of the X-Y scanner. Therefore, these implementations can be operated at the fast X-Y transverse scanning speed instead of the slower Z-scanning speed.

In yet other various embodiments the incisions can take a wide variety of shapes including straight planes, curved planes, cones, tilted cylinders, any type of shapes which are not transverse to the z axis, incisions which have portions which are transverse to the z axis, various crossing patterns and any combination of these patterns. Such shapes can be connected by interconnecting planes that further fragment the lens tissue, while also potentially easing the delivery of laser pulses by reducing the need to shutter the laser or make large movements with the scanning system.

After cutting the fibers by the laser-formed incisions, the cut fibers can be removed with a variety of techniques, including hydro-dissection, manual fragmentation, the application of ultrasound, aspiration, or a combination of these or other methods.

FIG. 5K illustrates yet another composite implementation. In this implementation, a shield layer 280 can be implemented in the posterior-most region of the lens, to a substantial degree transverse to the axis of the eye. One of the functions of this protection layer 280 is to protect the retina from the negative effects of the laser irradiation used for forming the incisions 262-i.

FIGS. 7-26 illustrate embodiments of a laser surgery system in relation to the above photodisruptive laser treatment.

One important aspect of laser surgical procedures is precise control and aiming of a laser beam, e.g., the beam position and beam focusing. Laser surgery systems can be designed to include laser control and aiming tools to precisely target laser pulses to a particular target inside the tissue. In various nanosecond photodisruptive laser surgical systems, such as the Nd:YAG laser systems, the required level of targeting precision is relatively low. This is in part because the laser energy used is relatively high and thus the affected tissue area is also relatively large, often covering an impacted area with a dimension in the hundreds of microns. The time between laser pulses in such systems tend to be long and manual controlled targeting is feasible and is commonly used. One example of such manual targeting mechanisms is a biomicroscope to visualize the target tissue in combination with a secondary laser source used as an aiming beam. The surgeon manually moves the focus of a laser focusing lens, usually with a joystick control, which is parfocal (with or without an offset) with their image through the microscope, so that the surgical beam or aiming beam is in best focus on the intended target.

Such techniques designed for use with low repetition rate laser surgical systems may be difficult to use with high repetition rate lasers operating at thousands of shots per second and relatively low energy per pulse. In surgical operations with high repetition rate lasers, much higher precision may be required due to the small effects of each single laser pulse and much higher positioning speed may be required due to the need to deliver thousands of pulses to new treatment areas very quickly.

Examples of high repetition rate pulsed lasers for laser surgical systems include pulsed lasers at a pulse repetition rate of thousands of shots per second or higher with relatively low energy per pulse. Such lasers use relatively low energy per pulse to localize the tissue effect caused by laser-induced photodisruption, e.g., the impacted tissue area by photodisruption on the order of microns or tens of microns. This localized tissue effect can improve the precision of the laser surgery and can be desirable in certain surgical procedures such as laser eye surgery. In one example of such surgery, placement of many hundred, thousands or millions of contiguous, nearly contiguous or pulses separated by known distances, can be used to achieve certain desired surgical effects, such as tissue incisions, separations or fragmentation.

Various surgical procedures using high repetition rate photodisruptive laser surgical systems with shorter laser pulse durations may require high precision in positioning each pulse in the target tissue under surgery both in an absolute position with respect to a target location on the target tissue and a relative position with respect to preceding pulses. For example, in some cases, laser pulses may be required to be delivered next to each other with an accuracy of a few microns within the time between pulses, which can be on the order of microseconds. Because the time between two sequential pulses is short and the precision requirement for the pulse alignment is high, manual targeting as used in low repetition rate pulsed laser systems may be no longer adequate or feasible.

One technique to facilitate and control precise, high speed positioning requirement for delivery of laser pulses into the tissue is attaching a applanation plate made of a transparent material such as a glass with a predefined contact surface to the tissue so that the contact surface of the applanation plate forms a well-defined optical interface with the tissue. This well-defined interface can facilitate transmission and focusing of laser light into the tissue to control or reduce optical aberrations or variations (such as due to specific eye optical properties or changes that occur with surface drying) that are most critical at the air-tissue interface, which in the eye is at the anterior surface of the cornea. Contact lenses can be designed for various applications and targets inside the eye and other tissues, including ones that are disposable or reusable. The contact glass or applanation plate on the surface of the target tissue can be used as a reference plate relative to which laser pulses are focused through the adjustment of focusing elements within the laser delivery system. This use of a contact glass or applanation plate provides better control of the optical qualities of the tissue surface and thus allow laser pulses to be accurately placed at a high speed at a desired location (interaction point) in the target tissue relative to the applanation reference plate with little optical distortion of the laser pulses.

One way for implementing an applanation plate on an eye is to use the applanation plate to provide a positional reference for delivering the laser pulses into a target tissue in the eye. This use of the applanation plate as a positional reference can be based on the known desired location of laser pulse focus in the target with sufficient accuracy prior to firing the laser pulses and that the relative positions of the reference plate and the individual internal tissue target must remain constant during laser firing. In addition, this method can require the focusing of the laser pulse to the desired location to be predictable and repeatable between eyes or in different regions within the same eye. In practical systems, it can be difficult to use the applanation plate as a positional reference to precisely localize laser pulses intraocularly because the above conditions may not be met in practical systems.

For example, if the crystalline lens is the surgical target, the precise distance from the reference plate on the surface of the eye to the target tends to vary due to the presence of collapsible structures, such as the cornea itself, the anterior chamber, and the iris. Not only is their considerable variability in the distance between the applanated cornea and the lens between individual eyes, but there can also be variation within the same eye depending on the specific surgical and applanation technique used by the surgeon. In addition, there can be movement of the targeted lens tissue relative to the applanated surface during the firing of the thousands of laser pulses required for achieving the surgical effect, further complicating the accurate delivery of pulses. In addition, structure within the eye may move due to the build-up of photodisruptive byproducts, such as cavitation bubbles. For example, laser pulses delivered to the crystalline lens can cause the lens capsule to bulge forward, requiring adjustment to target this tissue for subsequent placement of laser pulses. Furthermore, it can be difficult to use computer models and simulations to predict, with sufficient accuracy, the actual location of target tissues after the applanation plate is removed and to adjust placement of laser pulses to achieve the desired localization without applanation in part because of the highly variable nature of applanation effects, which can depend on factors particular to the individual cornea or eye, and the specific surgical and applanation technique used by a surgeon.

In addition to the physical effects of applanation that disproportionably affect the localization of internal tissue structures, in some surgical processes, it may be desirable for a targeting system to anticipate or account for nonlinear characteristics of photodisruption which can occur when using short pulse duration lasers. Photodisruption is a nonlinear optical process in the tissue material and can cause complications in beam alignment and beam targeting. For example, one of the nonlinear optical effects in the tissue material when interacting with laser pulses during the photodisruption is that the refractive index of the tissue material experienced by the laser pulses is no longer a constant but varies with the intensity of the light. Because the intensity of the light in the laser pulses varies spatially within the pulsed laser beam, along and across the propagation direction of the pulsed laser beam, the refractive index of the tissue material also varies spatially. One consequence of this nonlinear refractive index is self-focusing or self-defocusing in the tissue material that changes the actual focus of and shifts the position of the focus of the pulsed laser beam inside the tissue. Therefore, a precise alignment of the pulsed laser beam to each target tissue position in the target tissue may also need to account for the nonlinear optical effects of the tissue material on the laser beam. In addition, it may be necessary to adjust the energy in each pulse to deliver the same physical effect in different regions of the target due to different physical characteristics, such as hardness, or due to optical considerations such as absorption or scattering of laser pulse light traveling to a particular region. In such cases, the differences in non-linear focusing effects between pulses of different energy values can also affect the laser alignment and laser targeting of the surgical pulses.

Thus, in surgical procedures in which non superficial structures are targeted, the use of a superficial applanation plate based on a positional reference provided by the applanation plate may be insufficient to achieve precise laser pulse localization in internal tissue targets. The use of the applanation plate as the reference for guiding laser delivery may require measurements of the thickness and plate position of the applanation plate with high accuracy because the deviation from nominal is directly translated into a depth precision error. High precision applanation lenses can be costly, especially for single use disposable applanation plates.

The techniques, apparatus and systems described in this document can be implemented in ways that provide a targeting mechanism to deliver short laser pulses through an applanation plate to a desired localization inside the eye with precision and at a high speed without requiring the known desired location of laser pulse focus in the target with sufficient accuracy prior to firing the laser pulses and without requiring that the relative positions of the reference plate and the individual internal tissue target remain constant during laser firing. As such, the present techniques, apparatus and systems can be used for various surgical procedures where physical conditions of the target tissue under surgery tend to vary and are difficult to control and the dimension of the applanation lens tends to vary from one lens to another. The present techniques, apparatus and systems may also be used for other surgical targets where distortion or movement of the surgical target relative to the surface of the structure is present or non-linear optical effects make precise targeting problematic. Examples for such surgical targets different from the eye include the heart, deeper tissue in the skin and others.

The present techniques, apparatus and systems can be implemented in ways that maintain the benefits provided by an applanation plate, including, for example, control of the surface shape and hydration, as well as reductions in optical distortion, while providing for the precise localization of photodisruption to internal structures of the applanated surface. This can be accomplished through the use of an integrated imaging device to localize the target tissue relative to the focusing optics of the delivery system. The exact type of imaging device and method can vary and may depend on the specific nature of the target and the required level of precision.

An applanation lens may be implemented with another mechanism to fix the eye to prevent translational and rotational movement of the eye. Examples of such fixation devices include the use of a suction ring. Such fixation mechanism can also lead to unwanted distortion or movement of the surgical target. The present techniques, apparatus and systems can be implemented to provide, for high repetition rate laser surgical systems that utilize an applanation plate and/or fixation means for non-superficial surgical targets, a targeting mechanism to provide intraoperative imaging to monitor such distortion and movement of the surgical target.

Specific examples of laser surgical techniques, apparatus and systems are described below to use an optical imaging module to capture images of a target tissue to obtain positioning information of the target tissue, e.g., before and during a surgical procedure. Such obtained positioning information can be used to control the positioning and focusing of the surgical laser beam in the target tissue to provide accurate control of the placement of the surgical laser pulses in high repetition rate laser systems. In one implementation, during a surgical procedure, the images obtained by the optical imaging module can be used to dynamically control the position and focus of the surgical laser beam. In addition, lower energy and shot laser pulses tend to be sensitive to optical distortions, such a laser surgical system can implement an applanation plate with a flat or curved interface attaching to the target tissue to provide a controlled and stable optical interface between the target tissue and the surgical laser system and to mitigate and control optical aberrations at the tissue surface.

Figure 7:
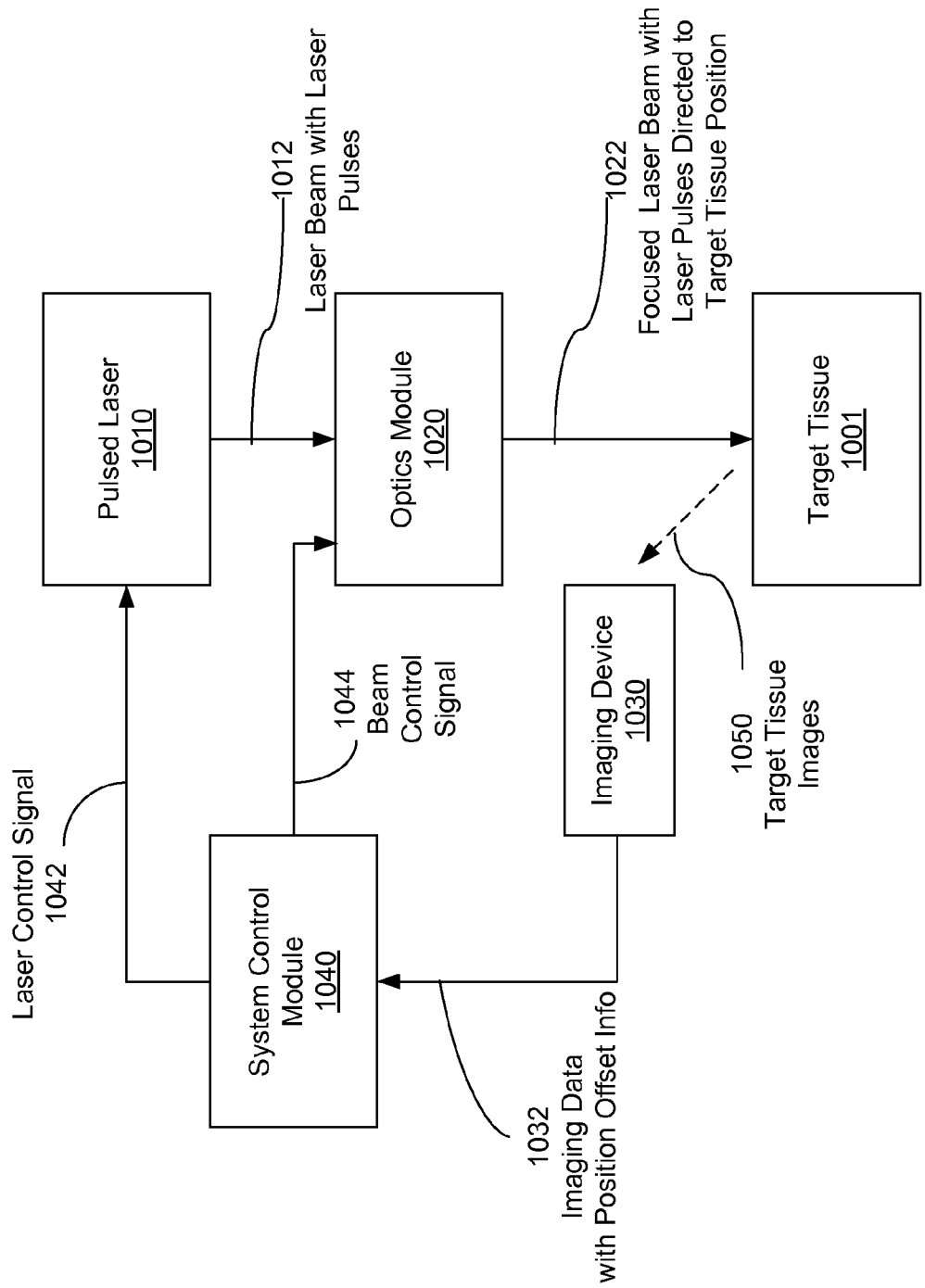
FIG. 7 shows an example of an imaging-guided laser surgical system in which an imaging module is provided to provide imaging of a target to the laser control.

As an example, FIG. 7 shows a laser surgical system based on optical imaging and applanation. This system includes a pulsed laser 1010 to produce a surgical laser beam 1012 of laser pulses, and an optics module 1020 to receive the surgical laser beam 1012 and to focus and direct the focused surgical laser beam 1022 onto a target tissue 1001, such as an eye, to cause photodisruption in the target tissue 1001. An applanation plate can be provided to be in contact with the target tissue 1001 to produce an interface for transmitting laser pulses to the target tissue 1001 and light coming from the target tissue 1001 through the interface. Notably, an optical imaging device 1030 is provided to capture light 1050 carrying target tissue images 1050 or imaging information from the target tissue 1001 to create an image of the target tissue 1001. The imaging signal 1032 from the imaging device 1030 is sent to a system control module 1040. The system control module 1040 operates to process the captured images from the image device 1030 and to control the optics module 1020 to adjust the position and focus of the surgical laser beam 1022 at the target tissue 101 based on information from the captured images. The optics module 120 can include one or more lenses and may further include one or more reflectors. A control actuator can be included in the optics module 1020 to adjust the focusing and the beam direction in response to a beam control signal 1044 from the system control module 1040. The control module 1040 can also control the pulsed laser 1010 via a laser control signal 1042.

The optical imaging device 1030 may be implemented to produce an optical imaging beam that is separate from the surgical laser beam 1022 to probe the target tissue 1001 and the returned light of the optical imaging beam is captured by the optical imaging device 1030 to obtain the images of the target tissue 1001. One example of such an optical imaging device 1030 is an optical coherence tomography (OCT) imaging module which uses two imaging beams, one probe beam directed to the target tissue 1001 thought the applanation plate and another reference beam in a reference optical path, to optically interfere with each other to obtain images of the target tissue 1001. In other implementations, the optical imaging device 1030 can use scattered or reflected light from the target tissue 1001 to capture images without sending a designated optical imaging beam to the target tissue 1001. For example, the imaging device 1030 can be a sensing array of sensing elements such as CCD or CMS sensors. For example, the images of photodisruption byproduct produced by the surgical laser beam 1022 may be captured by the optical imaging device 1030 for controlling the focusing and positioning of the surgical laser beam 1022. When the optical imaging device 1030 is designed to guide surgical laser beam alignment using the image of the photodisruption byproduct, the optical imaging device 1030 captures images of the photodisruption byproduct such as the laser-induced bubbles or cavities. The imaging device 1030 may also be an ultrasound imaging device to capture images based on acoustic images.

The system control module 1040 processes image data from the imaging device 1030 that includes the position offset information for the photodisruption byproduct from the target tissue position in the target tissue 1001. Based on the information obtained from the image, the beam control signal 1044 is generated to control the optics module 1020 which adjusts the laser beam 1022. A digital processing unit can be included in the system control module 1040 to perform various data processing for the laser alignment.

The above techniques and systems can be used deliver high repetition rate laser pulses to subsurface targets with a precision required for contiguous pulse placement, as needed for cutting or volume disruption applications. This can be accomplished with or without the use of a reference source on the surface of the target and can take into account movement of the target following applanation or during placement of laser pulses.

The applanation plate in the present systems is provided to facilitate and control precise, high speed positioning requirement for delivery of laser pulses into the tissue. Such an applanation plate can be made of a transparent material such as a glass with a predefined contact surface to the tissue so that the contact surface of the applanation plate forms a well-defined optical interface with the tissue. This well-defined interface can facilitate transmission and focusing of laser light into the tissue to control or reduce optical aberrations or variations (such as due to specific eye optical properties or changes that occur with surface drying) that are most critical at the air-tissue interface, which in the eye is at the anterior surface of the cornea. A number of contact lenses have been designed for various applications and targets inside the eye and other tissues, including ones that are disposable or reusable. The contact glass or applanation plate on the surface of the target tissue is used as a reference plate relative to which laser pulses are focused through the adjustment of focusing elements within the laser delivery system relative. Inherent in such an approach are the additional benefits afforded by the contact glass or applanation plate described previously, including control of the optical qualities of the tissue surface. Accordingly, laser pulses can be accurately placed at a high speed at a desired location (interaction point) in the target tissue relative to the applanation reference plate with little optical distortion of the laser pulses.

The optical imaging device 1030 in FIG. 7 captures images of the target tissue 1001 via the applanation plate. The control module 1040 processes the captured images to extract position information from the captured images and uses the extracted position information as a position reference or guide to control the position and focus of the surgical laser beam 1022. This imaging-guided laser surgery can be implemented without relying on the applanation plate as a position reference because the position of the applanation plate tends to change due to various factors as discussed above. Hence, although the applanation plate provides a desired optical interface for the surgical laser beam to enter the target tissue and to capture images of the target tissue, it may be difficult to use the applanation plate as a position reference to align and control the position and focus of the surgical laser beam for accurate delivery of laser pulses. The imaging-guided control of the position and focus of the surgical laser beam based on the imaging device 1030 and the control module 1040 allows the images of the target tissue 1001, e.g., images of inner structures of an eye, to be used as position references, without using the applanation plate to provide a position reference.

In addition to the physical effects of applanation that disproportionably affect the localization of internal tissue structures, in some surgical processes, it may be desirable for a targeting system to anticipate or account for nonlinear characteristics of photodisruption which can occur when using short pulse duration lasers. Photodisruption can cause complications in beam alignment and beam targeting. For example, one of the nonlinear optical effects in the tissue material when interacting with laser pulses during the photodisruption is that the refractive index of the tissue material experienced by the laser pulses is no longer a constant but varies with the intensity of the light. Because the intensity of the light in the laser pulses varies spatially within the pulsed laser beam, along and across the propagation direction of the pulsed laser beam, the refractive index of the tissue material also varies spatially. One consequence of this nonlinear refractive index is self-focusing or self-defocusing in the tissue material that changes the actual focus of and shifts the position of the focus of the pulsed laser beam inside the tissue. Therefore, a precise alignment of the pulsed laser beam to each target tissue position in the target tissue may also need to account for the nonlinear optical effects of the tissue material on the laser beam. The energy of the laser pulses may be adjusted to deliver the same physical effect in different regions of the target due to different physical characteristics, such as hardness, or due to optical considerations such as absorption or scattering of laser pulse light traveling to a particular region. In such cases, the differences in non-linear focusing effects between pulses of different energy values can also affect the laser alignment and laser targeting of the surgical pulses. In this regard, the direct images obtained from the target issue by the imaging device 1030 can be used to monitor the actual position of the surgical laser beam 1022 which reflects the combined effects of nonlinear optical effects in the target tissue and provide position references for control of the beam position and beam focus.

The techniques, apparatus and systems described here can be used in combination of an applanation plate to provide control of the surface shape and hydration, to reduce optical distortion, and provide for precise localization of photodisruption to internal structures through the applanated surface. The imaging-guided control of the beam position and focus described here can be applied to surgical systems and procedures that use means other than applanation plates to fix the eye, including the use of a suction ring which can lead to distortion or movement of the surgical target.

The following sections first describe examples of techniques, apparatus and systems for automated imaging-guided laser surgery based on varying degrees of integration of imaging functions into the laser control part of the systems. An optical or other modality imaging module, such as an OCT imaging module, can be used to direct a probe light or other type of beam to capture images of a target tissue, e.g., structures inside an eye. A surgical laser beam of laser pulses such as femtosecond or picosecond laser pulses can be guided by position information in the captured images to control the focusing and positioning of the surgical laser beam during the surgery. Both the surgical laser beam and the probe light beam can be sequentially or simultaneously directed to the target tissue during the surgery so that the surgical laser beam can be controlled based on the captured images to ensure precision and accuracy of the surgery.

Such imaging-guided laser surgery can be used to provide accurate and precise focusing and positioning of the surgical laser beam during the surgery because the beam control is based on images of the target tissue following applanation or fixation of the target tissue, either just before or nearly simultaneously with delivery of the surgical pulses. Notably, certain parameters of the target tissue such as the eye measured before the surgery may change during the surgery due to various factor such as preparation of the target tissue (e.g., fixating the eye to an applanation lens) and the alternation of the target tissue by the surgical operations. Therefore, measured parameters of the target tissue prior to such factors and/or the surgery may no longer reflect the physical conditions of the target tissue during the surgery. The present imaging-guided laser surgery can mitigate technical issues in connection with such changes for focusing and positioning the surgical laser beam before and during the surgery.

The present imaging-guided laser surgery may be effectively used for accurate surgical operations inside a target tissue. For example, when performing laser surgery inside the eye, laser light is focused inside the eye to achieve optical breakdown of the targeted tissue and such optical interactions can change the internal structure of the eye. For example, the crystalline lens can change its position, shape, thickness and diameter during accommodation, not only between prior measurement and surgery but also during surgery. Attaching the eye to the surgical instrument by mechanical means can change the shape of the eye in a not well defined way and further, the change can vary during surgery due to various factors, e.g., patient movement. Attaching means include fixating the eye with a suction ring and applanating the eye with a flat or curved lens. These changes amount to as much as a few millimeters. Mechanically referencing and fixating the surface of the eye such as the anterior surface of the cornea or limbus does not work well when performing precision laser microsurgery inside the eye.

The post preparation or near simultaneous imaging in the present imaging-guided laser surgery can be used to establish three-dimensional positional references between the inside features of the eye and the surgical instrument in an environment where changes occur prior to and during surgery. The positional reference information provided by the imaging prior to applanation and/or fixation of the eye, or during the actual surgery reflects the effects of changes in the eye and thus provides an accurate guidance to focusing and positioning of the surgical laser beam. A system based on the present imaging-guided laser surgery can be configured to be simple in structure and cost efficient. For example, a portion of the optical components associated with guiding the surgical laser beam can be shared with optical components for guiding the probe light beam for imaging the target tissue to simplify the device structure and the optical alignment and calibration of the imaging and surgical light beams.

The imaging-guided laser surgical systems described below use the OCT imaging as an example of an imaging instrument and other non-OCT imaging devices may also be used to capture images for controlling the surgical lasers during the surgery. As illustrated in the examples below, integration of the imaging and surgical subsystems can be implemented to various degrees. In the simplest form without integrating hardware, the imaging and laser surgical subsystems are separated and can communicate to one another through interfaces. Such designs can provide flexibility in the designs of the two subsystems. Integration between the two subsystems, by some hardware components such as a patient interface, further expands the functionality by offering better registration of surgical area to the hardware components, more accurate calibration and may improve workflow. As the degree of integration between the two subsystems increases, such a system may be made increasingly cost-efficient and compact and system calibration will be further simplified and more stable over time. Examples for imaging-guided laser systems in FIGS. 8-16 are integrated at various degrees of integration.

One implementation of a present imaging-guided laser surgical system, for example, includes a surgical laser that produces a surgical laser beam of surgical laser pulses that cause surgical changes in a target tissue under surgery; a patient interface mount that engages a patient interface in contact with the target tissue to hold the target tissue in position; and a laser beam delivery module located between the surgical laser and the patient interface and configured to direct the surgical laser beam to the target tissue through the patient interface. This laser beam delivery module is operable to scan the surgical laser beam in the target tissue along a predetermined surgical pattern. This system also includes a laser control module that controls operation of the surgical laser and controls the laser beam delivery module to produce the predetermined surgical pattern and an OCT module positioned relative to the patient interface to have a known spatial relation with respect to the patient interface and the target issue fixed to the patient interface. The OCT module is configured to direct an optical probe beam to the target tissue and receive returned probe light of the optical probe beam from the target tissue to capture OCT images of the target tissue while the surgical laser beam is being directed to the target tissue to perform an surgical operation so that the optical probe beam and the surgical laser beam are simultaneously present in the target tissue. The OCT module is in communication with the laser control module to send information of the captured OCT images to the laser control module.

In addition, the laser control module in this particular system responds to the information of the captured OCT images to operate the laser beam delivery module in focusing and scanning of the surgical laser beam and adjusts the focusing and scanning of the surgical laser beam in the target tissue based on positioning information in the captured OCT images.

In some implementations, acquiring a complete image of a target tissue may not be necessary for registering the target to the surgical instrument and it may be sufficient to acquire a portion of the target tissue, e.g., a few points from the surgical region such as natural or artificial landmarks. For example, a rigid body has six degrees of freedom in 3D space and six independent points would be sufficient to define the rigid body. When the exact size of the surgical region is not known, additional points are needed to provide the positional reference. In this regard, several points can be used to determine the position and the curvature of the anterior and posterior surfaces, which are normally different, and the thickness and diameter of the crystalline lens of the human eye. Based on these data a body made up from two halves of ellipsoid bodies with given parameters can approximate and visualize a crystalline lens for practical purposes. In another implementation, information from the captured image may be combined with information from other sources, such as pre-operative measurements of lens thickness that are used as an input for the controller.

Figure 8:
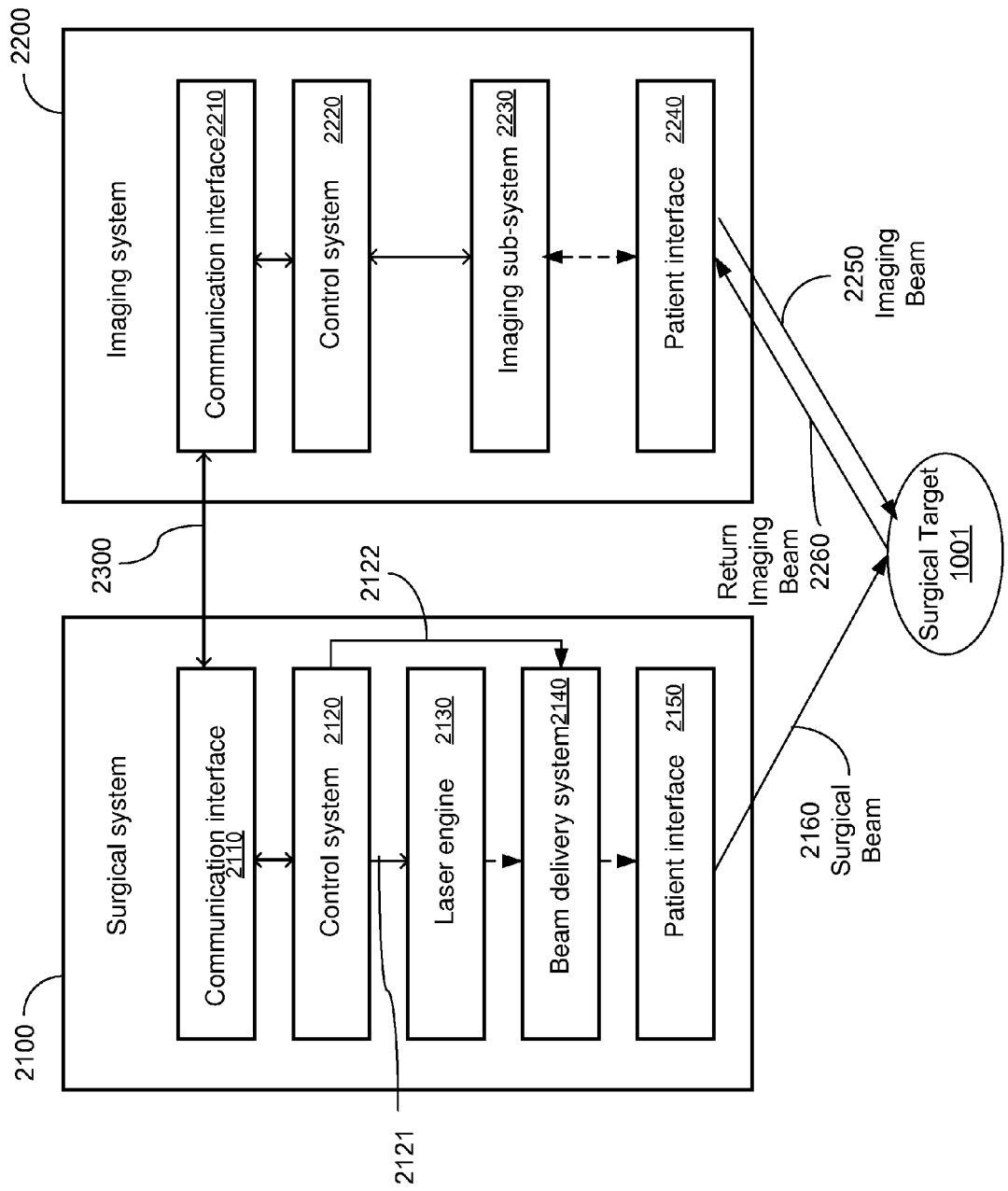
FIGS. 8-16 show examples of imaging-guided laser surgical systems with varying degrees of integration of a laser surgical system and an imaging system.

FIG. 8 shows one example of an imaging-guided laser surgical system with separated laser surgical system 2100 and imaging system 2200. The laser surgical system 2100 includes a laser engine 2130 with a surgical laser that produces a surgical laser beam 2160 of surgical laser pulses. A laser beam delivery module 2140 is provided to direct the surgical laser beam 2160 from the laser engine 2130 to the target tissue 1001 through a patient interface 2150 and is operable to scan the surgical laser beam 2160 in the target tissue 1001 along a predetermined surgical pattern. A laser control module 2120 is provided to control the operation of the surgical laser in the laser engine 2130 via a communication channel 2121 and controls the laser beam delivery module 2140 via a communication channel 2122 to produce the predetermined surgical pattern. A patient interface mount is provided to engage the patient interface 2150 in contact with the target tissue 1001 to hold the target tissue 1001 in position. The patient interface 2150 can be implemented to include a contact lens or applanation lens with a flat or curved surface to conformingly engage to the anterior surface of the eye and to hold the eye in position.

The imaging system 2200 in FIG. 8 can be an OCT module positioned relative to the patient interface 2150 of the surgical system 2100 to have a known spatial relation with respect to the patient interface 2150 and the target issue 1001 fixed to the patient interface 2150. This OCT module 2200 can be configured to have its own patient interface 2240 for interacting with the target tissue 1001. The imaging system 2200 includes an imaging control module 2220 and an imaging sub-system 2230. The sub-system 2230 includes a light source for generating imaging beam 2250 for imaging the target 1001 and an imaging beam delivery module to direct the optical probe beam or imaging beam 2250 to the target tissue 1001 and receive returned probe light 2260 of the optical imaging beam 2250 from the target tissue 1001 to capture OCT images of the target tissue 1001. Both the optical imaging beam 2250 and the surgical beam 2160 can be simultaneously directed to the target tissue 1001 to allow for sequential or simultaneous imaging and surgical operation.

As illustrated in FIG. 8, communication interfaces 2110 and 2210 are provided in both the laser surgical system 2100 and the imaging system 2200 to facilitate the communications between the laser control by the laser control module 2120 and imaging by the imaging system 2200 so that the OCT module 2200 can send information of the captured OCT images to the laser control module 2120. The laser control module 2120 in this system responds to the information of the captured OCT images to operate the laser beam delivery module 2140 in focusing and scanning of the surgical laser beam 2160 and dynamically adjusts the focusing and scanning of the surgical laser beam 2160 in the target tissue 1001 based on positioning information in the captured OCT images. The integration between the laser surgical system 2100 and the imaging system 2200 is mainly through communication between the communication interfaces 2110 and 2210 at the software level.

In this and other examples, various subsystems or devices may also be integrated. For example, certain diagnostic instruments such as wavefront aberrometers, corneal topography measuring devices may be provided in the system, or pre-operative information from these devices can be utilized to augment intra-operative imaging.

Figure 9:
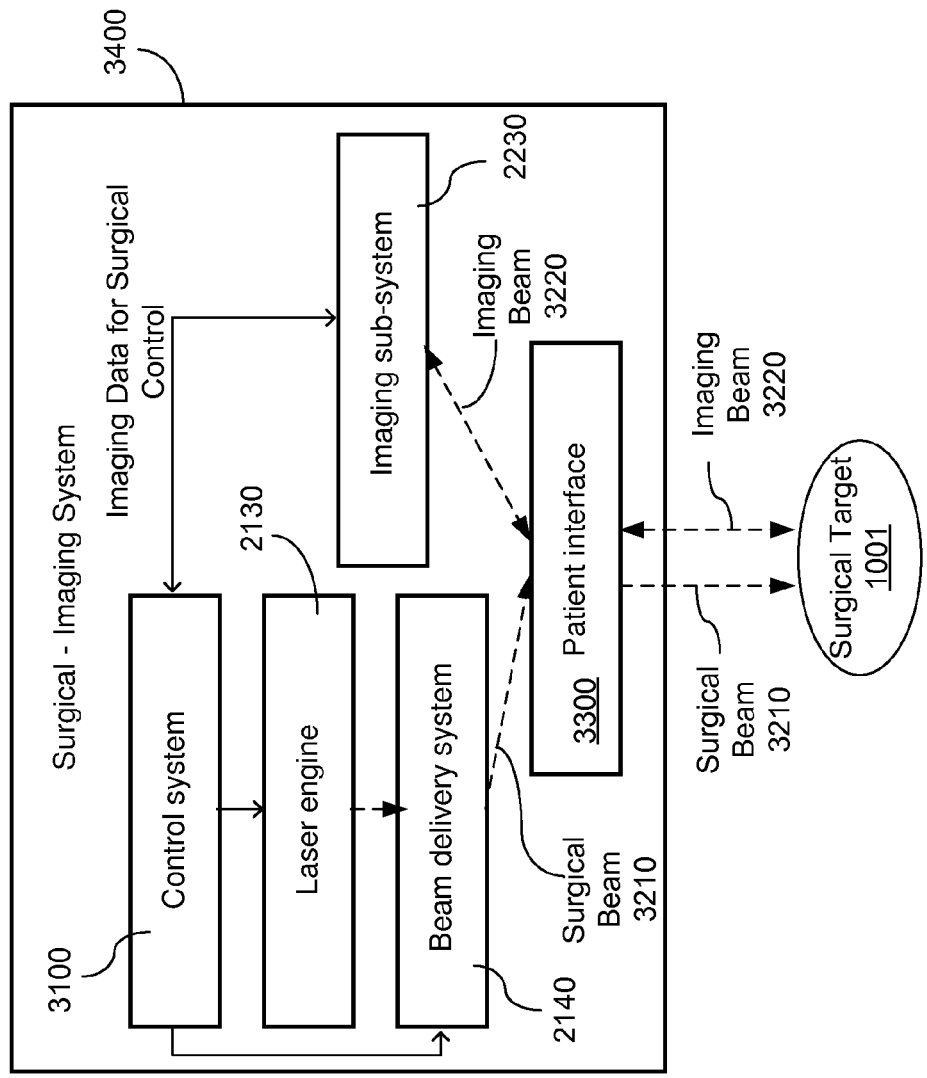

FIG. 9 shows an example of an imaging-guided laser surgical system with additional integration features. The imaging and surgical systems share a common patient interface 3300 which immobilizes target tissue 1001 (e.g., the eye) without having two separate patient interfaces as in FIG. 8. The surgical beam 3210 and the imaging beam 3220 are combined at the patient interface 3330 and are directed to the target 1001 by the common patient interface 3300. In addition, a common control module 3100 is provided to control both the imaging sub-system 2230 and the surgical part (the laser engine 2130 and the beam delivery system 2140). This increased integration between imaging and surgical parts allows accurate calibration of the two subsystems and the stability of the position of the patient and surgical volume. A common housing 3400 is provided to enclose both the surgical and imaging subsystems. When the two systems are not integrated into a common housing, the common patient interface 3300 can be part of either the imaging or the surgical subsystem.

Figure 10:
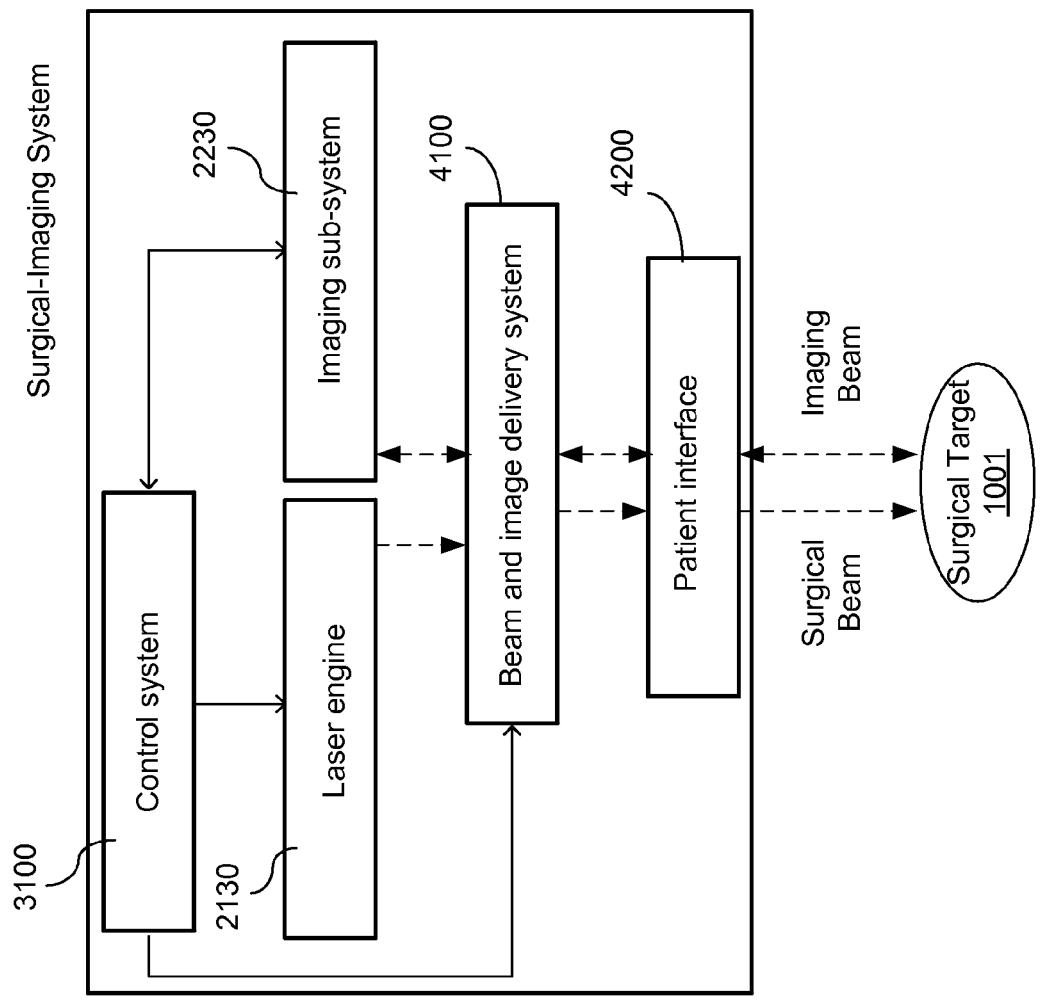

FIG. 10 shows an example of an imaging-guided laser surgical system where the laser surgical system and the imaging system share both a common beam delivery module 4100 and a common patient interface 4200. This integration further simplifies the system structure and system control operation.

In one implementation, the imaging system in the above and other examples can be an optical computed tomography (OCT) system and the laser surgical system is a femtosecond or picosecond laser based ophthalmic surgical system. In OCT, light from a low coherence, broadband light source such as a super luminescent diode is split into separate reference and signal beams. The signal beam is the imaging beam sent to the surgical target and the returned light of the imaging beam is collected and recombined coherently with the reference beam to form an interferometer. Scanning the signal beam perpendicularly to the optical axis of the optical train or the propagation direction of the light provides spatial resolution in the x-y direction while depth resolution comes from extracting differences between the path lengths of the reference arm and the returned signal beam in the signal arm of the interferometer. While the x-y scanner of different OCT implementations are essentially the same, comparing the path lengths and getting z-scan information can happen in different ways. In one implementation known as the time domain OCT, for example, the reference arm is continuously varied to change its path length while a photodetector detects interference modulation in the intensity of the re-combined beam. In a different implementation, the reference arm is essentially static and the spectrum of the combined light is analyzed for interference. The Fourier transform of the spectrum of the combined beam provides spatial information on the scattering from the interior of the sample. This method is known as the spectral domain or Fourier OCT method. In a different implementation known as a frequency swept OCT (S. R. Chinn, et. al., Opt. Lett. 22, 1997), a narrowband light source is used with its frequency swept rapidly across a spectral range. Interference between the reference and signal arms is detected by a fast detector and dynamic signal analyzer. An external cavity tuned diode laser or frequency tuned of frequency domain mode-locked (FDML) laser developed for this purpose (R. Huber et. Al. Opt. Express, 13, 2005) (S. H. Yun, IEEE J. of Sel. Q. El. 3(4) p. 1087-1096, 1997) can be used in these examples as a light source. A femtosecond laser used as a light source in an OCT system can have sufficient bandwidth and can provide additional benefits of increased signal to noise ratios.

The OCT imaging device in the systems in this document can be used to perform various imaging functions. For example, the OCT can be used to suppress complex conjugates resulting from the optical configuration of the system or the presence of the applanation plate, capture OCT images of selected locations inside the target tissue to provide three-dimensional positioning information for controlling focusing and scanning of the surgical laser beam inside the target tissue, or capture OCT images of selected locations on the surface of the target tissue or on the applanation plate to provide positioning registration for controlling changes in orientation that occur with positional changes of the target, such as from upright to supine. The OCT can be calibrated by a positioning registration process based on placement of marks or markers in one positional orientation of the target that can then be detected by the OCT module when the target is in another positional orientation. In other implementations, the OCT imaging system can be used to produce a probe light beam that is polarized to optically gather the information on the internal structure of the eye. The laser beam and the probe light beam may be polarized in different polarizations. The OCT can include a polarization control mechanism that controls the probe light used for said optical tomography to polarize in one polarization when traveling toward the eye and in a different polarization when traveling away from the eye. The polarization control mechanism can include, e.g., a wave-plate or a Faraday rotator.

The system in FIG. 10 is shown as a spectral OCT configuration and can be configured to share the focusing optics part of the beam delivery module between the surgical and the imaging systems. The main requirements for the optics are related to the operating wavelength, image quality, resolution, distortion etc. The laser surgical system can be a femtosecond laser system with a high numerical aperture system designed to achieve diffraction limited focal spot sizes, e.g., about 2 to 3 micrometers. Various femtosecond ophthalmic surgical lasers can operate at various wavelengths such as wavelengths of around 1.05 micrometer. The operating wavelength of the imaging device can be selected to be close to the laser wavelength so that the optics is chromatically compensated for both wavelengths. Such a system may include a third optical channel, a visual observation channel such as a surgical microscope, to provide an additional imaging device to capture images of the target tissue. If the optical path for this third optical channel shares optics with the surgical laser beam and the light of the OCT imaging device, the shared optics can be configured with chromatic compensation in the visible spectral band for the third optical channel and the spectral bands for the surgical laser beam and the OCT imaging beam.

Figure 11:
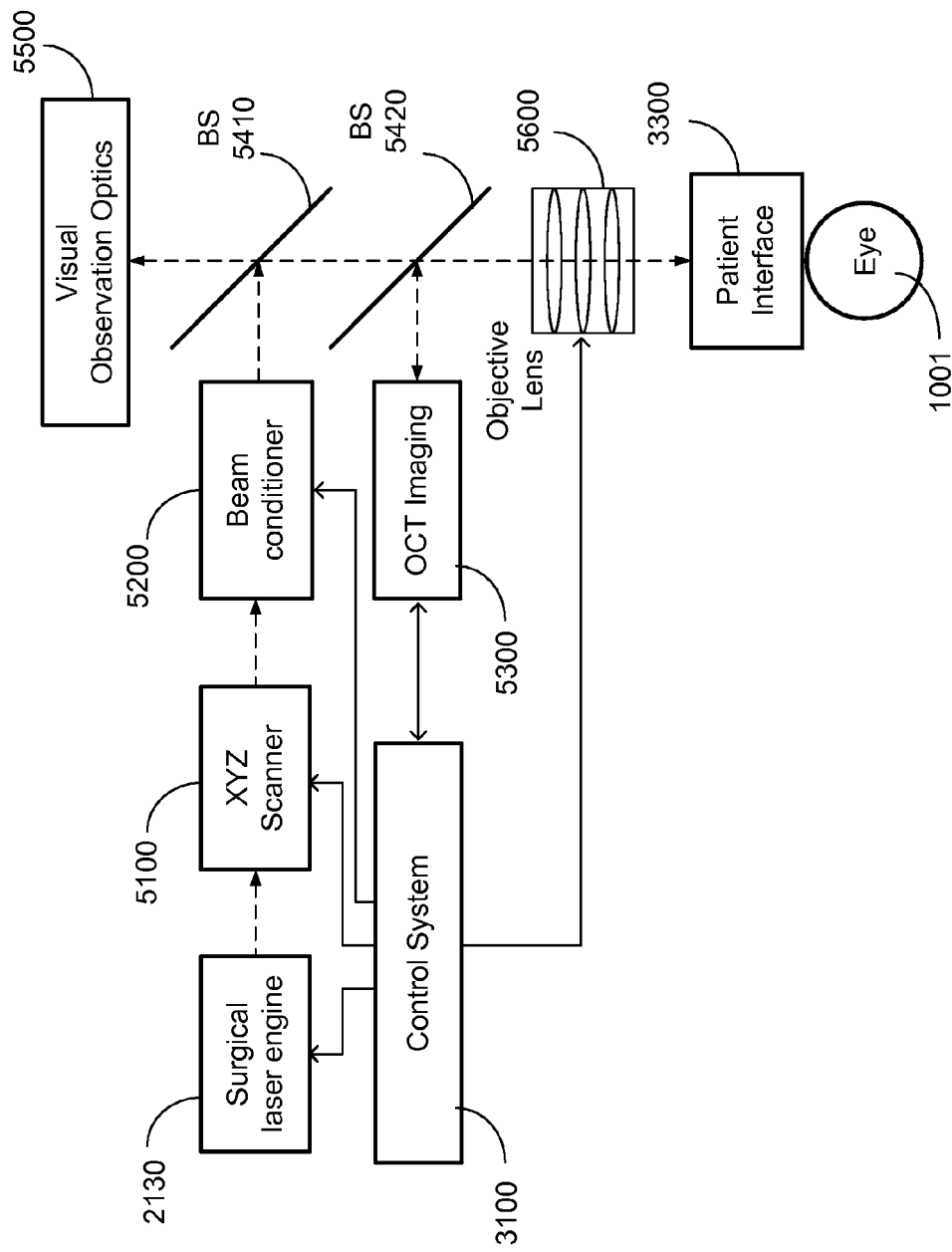

FIG. 11 shows a particular example of the design in FIG. 9 where the scanner 5100 for scanning the surgical laser beam and the beam conditioner 5200 for conditioning (collimating and focusing) the surgical laser beam are separate from the optics in the OCT imaging module 5300 for controlling the imaging beam for the OCT. The surgical and imaging systems share an objective lens 5600 module and the patient interface 3300. The objective lens 5600 directs and focuses both the surgical laser beam and the imaging beam to the patient interface 3300 and its focusing is controlled by the control module 3100. Two beam splitters 5410 and 5420 are provided to direct the surgical and imaging beams. The beam splitter 5420 is also used to direct the returned imaging beam back into the OCT imaging module 5300. Two beam splitters 5410 and 5420 also direct light from the target 1001 to a visual observation optics unit 5500 to provide direct view or image of the target 1001. The unit 5500 can be a lens imaging system for the surgeon to view the target 1001 or a camera to capture the image or video of the target 1001. Various beam splitters can be used, such as dichroic and polarization beam splitters, optical grating, holographic beam splitter or a combinations of these.

In some implementations, the optical components may be appropriately coated with antireflection coating for both the surgical and for the OCT wavelength to reduce glare from multiple surfaces of the optical beam path. Reflections would otherwise reduce the throughput of the system and reduce the signal to noise ratio by increasing background light in the OCT imaging unit. One way to reduce glare in the OCT is to rotate the polarization of the return light from the sample by wave-plate of Faraday isolator placed close to the target tissue and orient a polarizer in front of the OCT detector to preferentially detect light returned from the sample and suppress light scattered from the optical components.

In a laser surgical system, each of the surgical laser and the OCT system can have a beam scanner to cover the same surgical region in the target tissue. Hence, the beam scanning for the surgical laser beam and the beam scanning for the imaging beam can be integrated to share common scanning devices.

Figure 12:
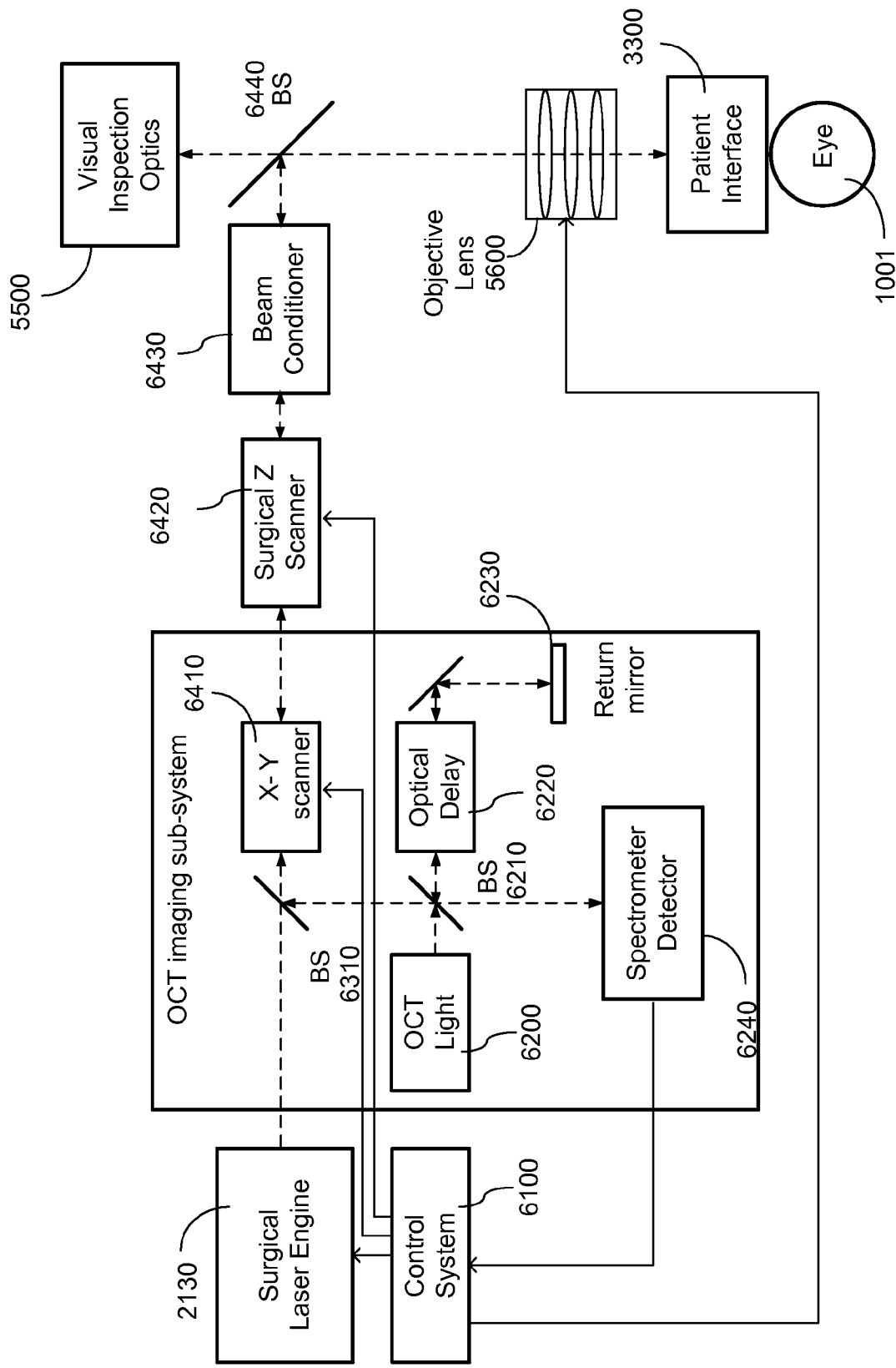

FIG. 12 shows an example of such a system in detail. In this implementation the x-y scanner 6410 and the z scanner 6420 are shared by both subsystems. A common control 6100 is provided to control the system operations for both surgical and imaging operations. The OCT sub-system includes an OCT light source 6200 that produce the imaging light that is split into an imaging beam and a reference beam by a beam splitter 6210. The imaging beam is combined with the surgical beam at the beam splitter 6310 to propagate along a common optical path leading to the target 1001. The scanners 6410 and 6420 and the beam conditioner unit 6430 are located downstream from the beam splitter 6310. A beam splitter 6440 is used to direct the imaging and surgical beams to the objective lens 5600 and the patient interface 3300.

In the OCT sub-system, the reference beam transmits through the beam splitter 6210 to an optical delay device 6220 and is reflected by a return mirror 6230. The returned imaging beam from the target 1001 is directed back to the beam splitter 6310 which reflects at least a portion of the returned imaging beam to the beam splitter 6210 where the reflected reference beam and the returned imaging beam overlap and interfere with each other. A spectrometer detector 6240 is used to detect the interference and to produce OCT images of the target 1001. The OCT image information is sent to the control system 6100 for controlling the surgical laser engine 2130, the scanners 6410 and 6420 and the objective lens 5600 to control the surgical laser beam. In one implementation, the optical delay device 6220 can be varied to change the optical delay to detect various depths in the target tissue 1001.

If the OCT system is a time domain system, the two subsystems use two different z-scanners because the two scanners operate in different ways. In this example, the z scanner of the surgical system operates by changing the divergence of the surgical beam in the beam conditioner unit without changing the path lengths of the beam in the surgical beam path. On the other hand, the time domain OCT scans the z-direction by physically changing the beam path by a variable delay or by moving the position of the reference beam return mirror. After calibration, the two z-scanners can be synchronized by the laser control module. The relationship between the two movements can be simplified to a linear or polynomial dependence, which the control module can handle or alternatively calibration points can define a look-up table to provide proper scaling. Spectral/Fourier domain and frequency swept source OCT devices have no z-scanner, the length of the reference arm is static. Besides reducing costs, cross calibration of the two systems will be relatively straightforward. There is no need to compensate for differences arising from image distortions in the focusing optics or from the differences of the scanners of the two systems since they are shared.

In practical implementations of the surgical systems, the focusing objective lens 5600 is slidably or movably mounted on a base and the weight of the objective lens is balanced to limit the force on the patient's eye. The patient interface 3300 can include an applanation lens attached to a patient interface mount. The patient interface mount is attached to a mounting unit, which holds the focusing objective lens. This mounting unit is designed to ensure a stable connection between the patient interface and the system in case of unavoidable movement of the patient and allows gentler docking of the patient interface onto the eye. Various implementations for the focusing objective lens can be used and one example is described in U.S. Pat. No. 5,336,215 to Hsueh. This presence of an adjustable focusing objective lens can change the optical path length of the optical probe light as part of the optical interferometer for the OCT sub-system. Movement of the objective lens 5600 and patient interface 3300 can change the path length differences between the reference beam and the imaging signal beam of the OCT in an uncontrolled way and this may degrade the OCT depth information detected by the OCT. This would happen not only in time-domain but also in spectral/Fourier domain and frequency-swept OCT systems.

Figure 13:
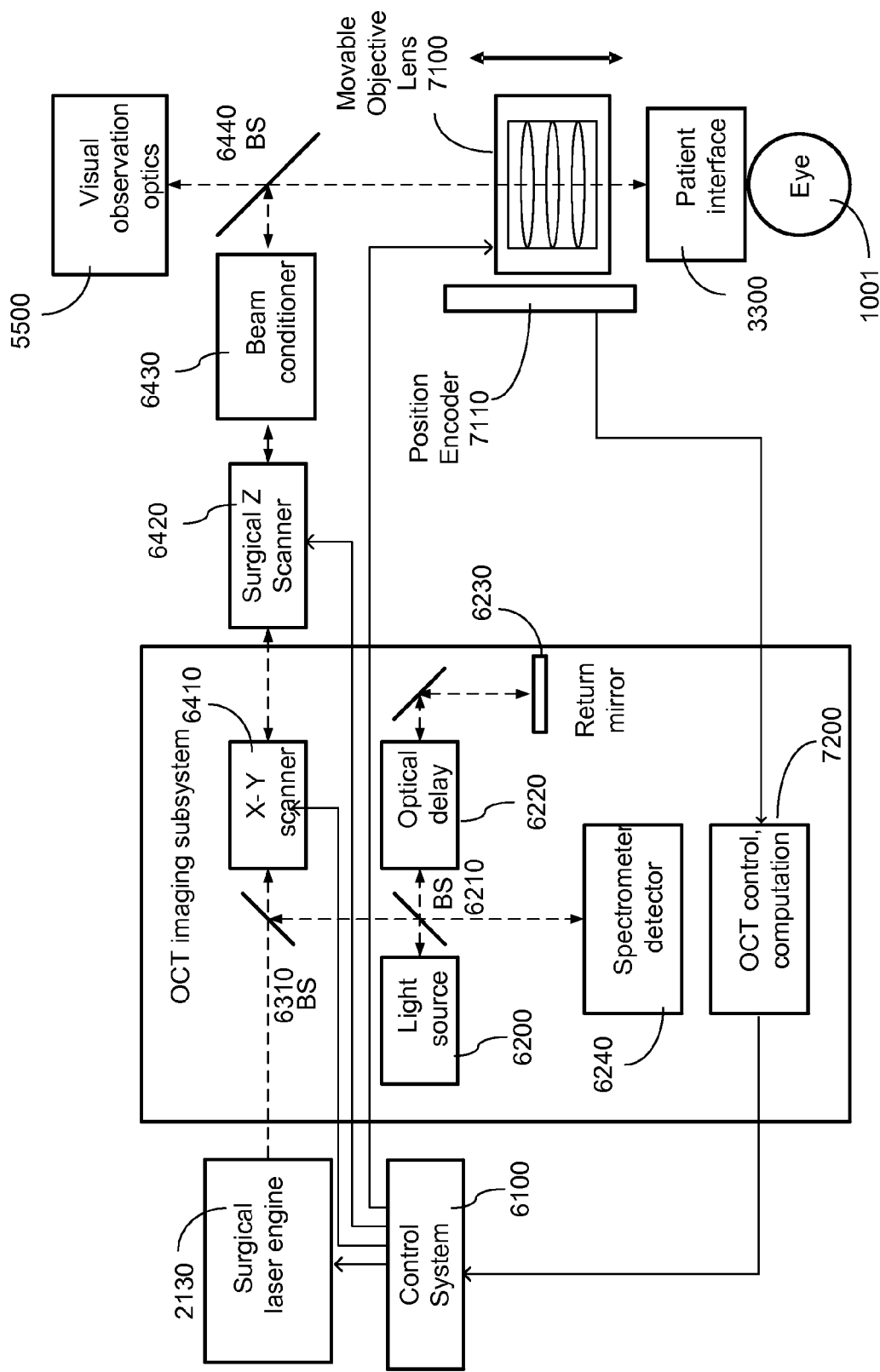
Figure 14:
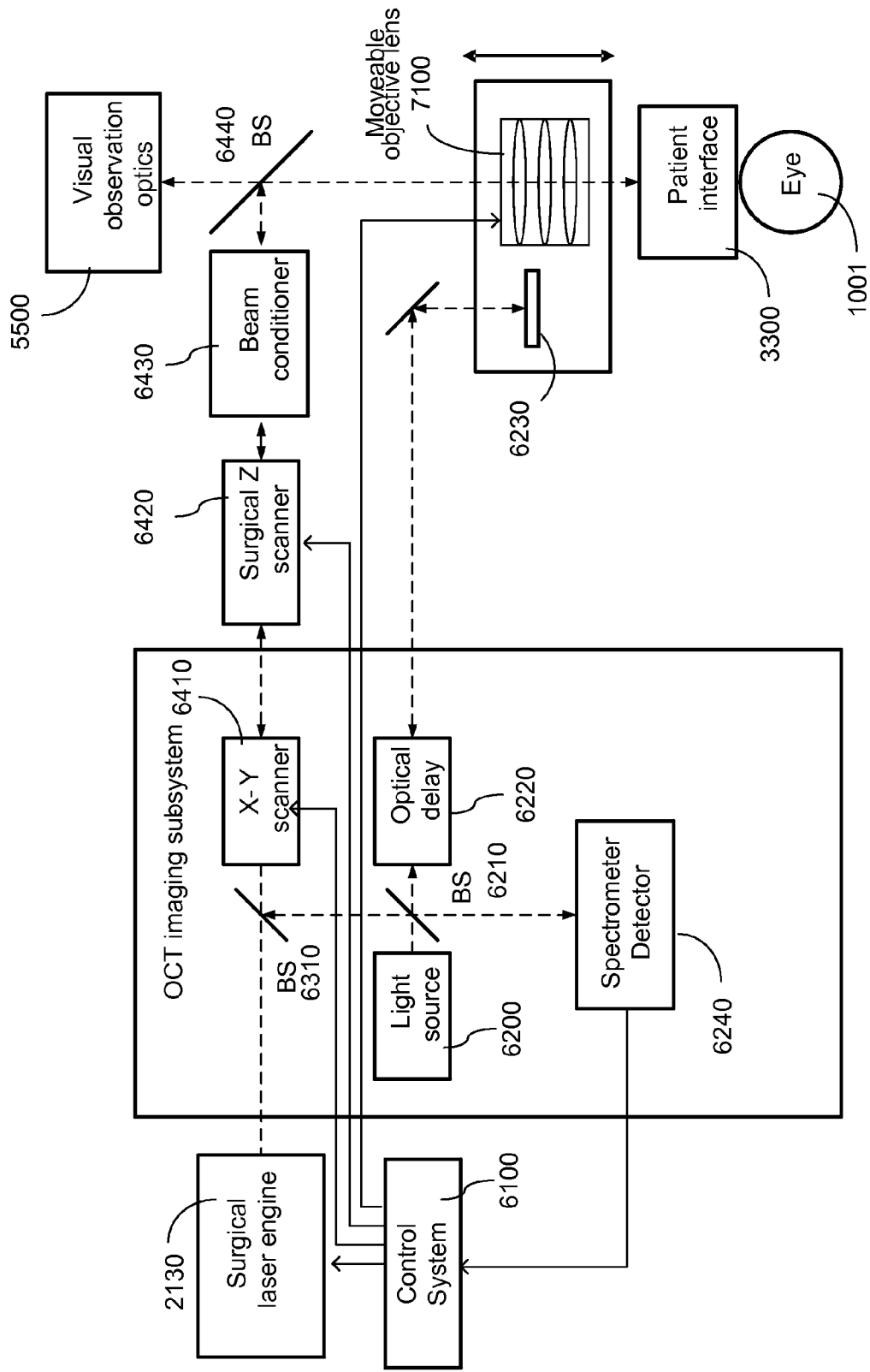

FIGS. 13 and 14 show exemplary imaging-guided laser surgical systems that address the technical issue associated with the adjustable focusing objective lens.

The system in FIG. 13 provides a position sensing device 7110 coupled to the movable focusing objective lens 7100 to measure the position of the objective lens 7100 on a slideable mount and communicates the measured position to a control module 7200 in the OCT system. The control system 6100 can control and move the position of the objective lens 7100 to adjust the optical path length traveled by the imaging signal beam for the OCT operation and the position of the lens 7100 is measured and monitored by the position encoder 7110 and direct fed to the OCT control 7200. The control module 7200 in the OCT system applies an algorithm, when assembling a 3D image in processing the OCT data, to compensate for differences between the reference arm and the signal arm of the interferometer inside the OCT caused by the movement of the focusing objective lens 7100 relative to the patient interface 3300. The proper amount of the change in the position of the lens 7100 computed by the OCT control module 7200 is sent to the control 6100 which controls the lens 7100 to change its position.

FIG. 14 shows another exemplary system where the return mirror 6230 in the reference arm of the interferometer of the OCT system or at least one part in an optical path length delay assembly of the OCT system is rigidly attached to the movable focusing objective lens 7100 so the signal arm and the reference arm undergo the same amount of change in the optical path length when the objective lens 7100 moves. As such, the movement of the objective lens 7100 on the slide is automatically compensated for path-length differences in the OCT system without additional need for a computational compensation.

The above examples for imaging-guided laser surgical systems, the laser surgical system and the OCT system use different light sources. In an even more complete integration between the laser surgical system and the OCT system, a femtosecond surgical laser as a light source for the surgical laser beam can also be used as the light source for the OCT system.

Figure 15:
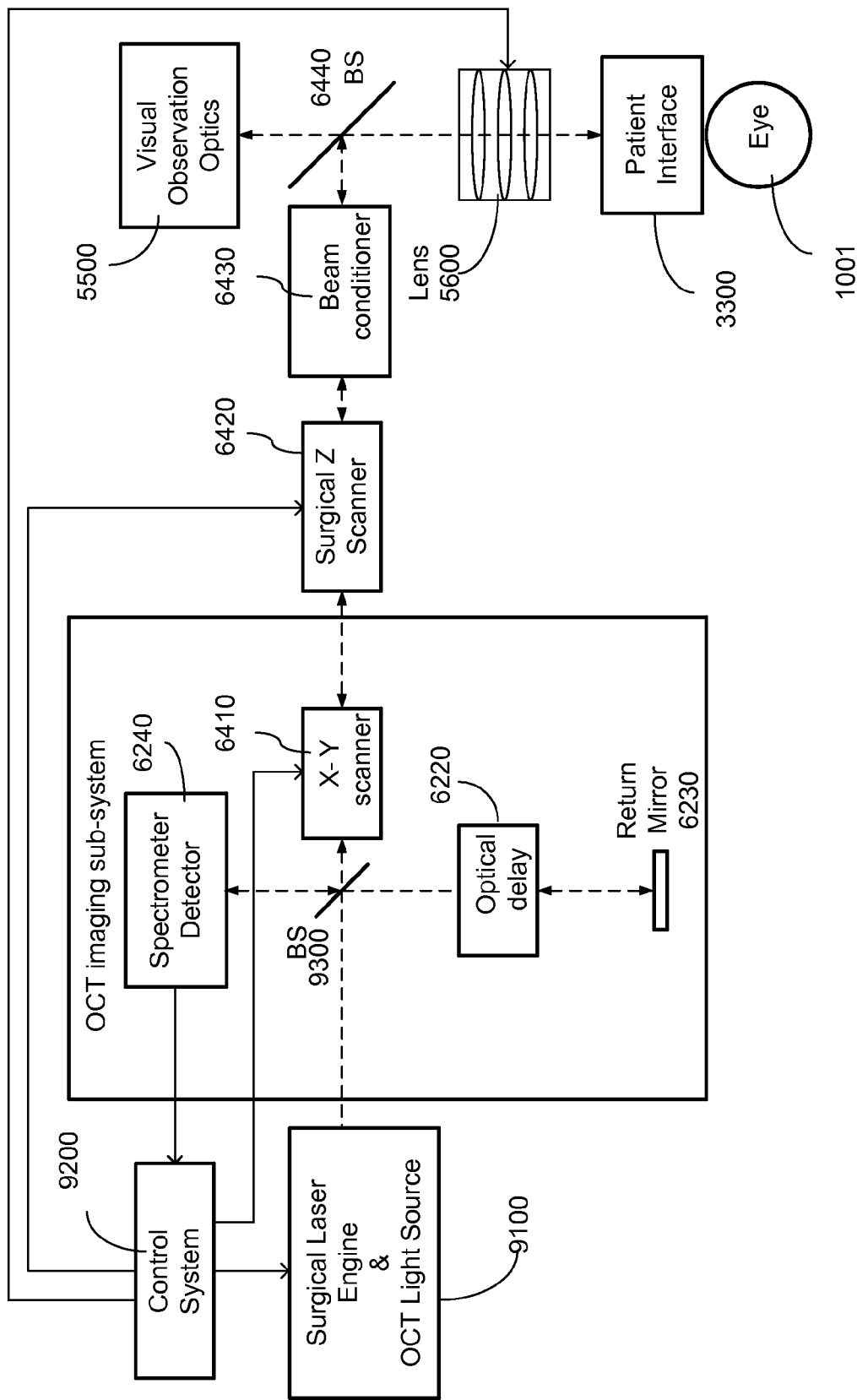

FIG. 15 shows an example where a femtosecond pulse laser in a light module 9100 is used to generate both the surgical laser beam for surgical operations and the probe light beam for OCT imaging. A beam splitter 9300 is provided to split the laser beam into a first beam as both the surgical laser beam and the signal beam for the OCT and a second beam as the reference beam for the OCT. The first beam is directed through an x-y scanner 6410 which scans the beam in the x and y directions perpendicular to the propagation direction of the first beam and a second scanner (z scanner) 6420 that changes the divergence of the beam to adjust the focusing of the first beam at the target tissue 1001. This first beam performs the surgical operations at the target tissue 1001 and a portion of this first beam is back scattered to the patient interface and is collected by the objective lens as the signal beam for the signal arm of the optical interferometer of the OCT system. This returned light is combined with the second beam that is reflected by a return mirror 6230 in the reference arm and is delayed by an adjustable optical delay element 6220 for a time-domain OCT to control the path difference between the signal and reference beams in imaging different depths of the target tissue 1001. The control system 9200 controls the system operations.

Surgical practice on the cornea has shown that a pulse duration of several hundred femtoseconds may be sufficient to achieve good surgical performance, while for OCT of a sufficient depth resolution broader spectral bandwidth generated by shorter pulses, e.g., below several tens of femtoseconds, are needed. In this context, the design of the OCT device dictates the duration of the pulses from the femtosecond surgical laser.

Figure 16:
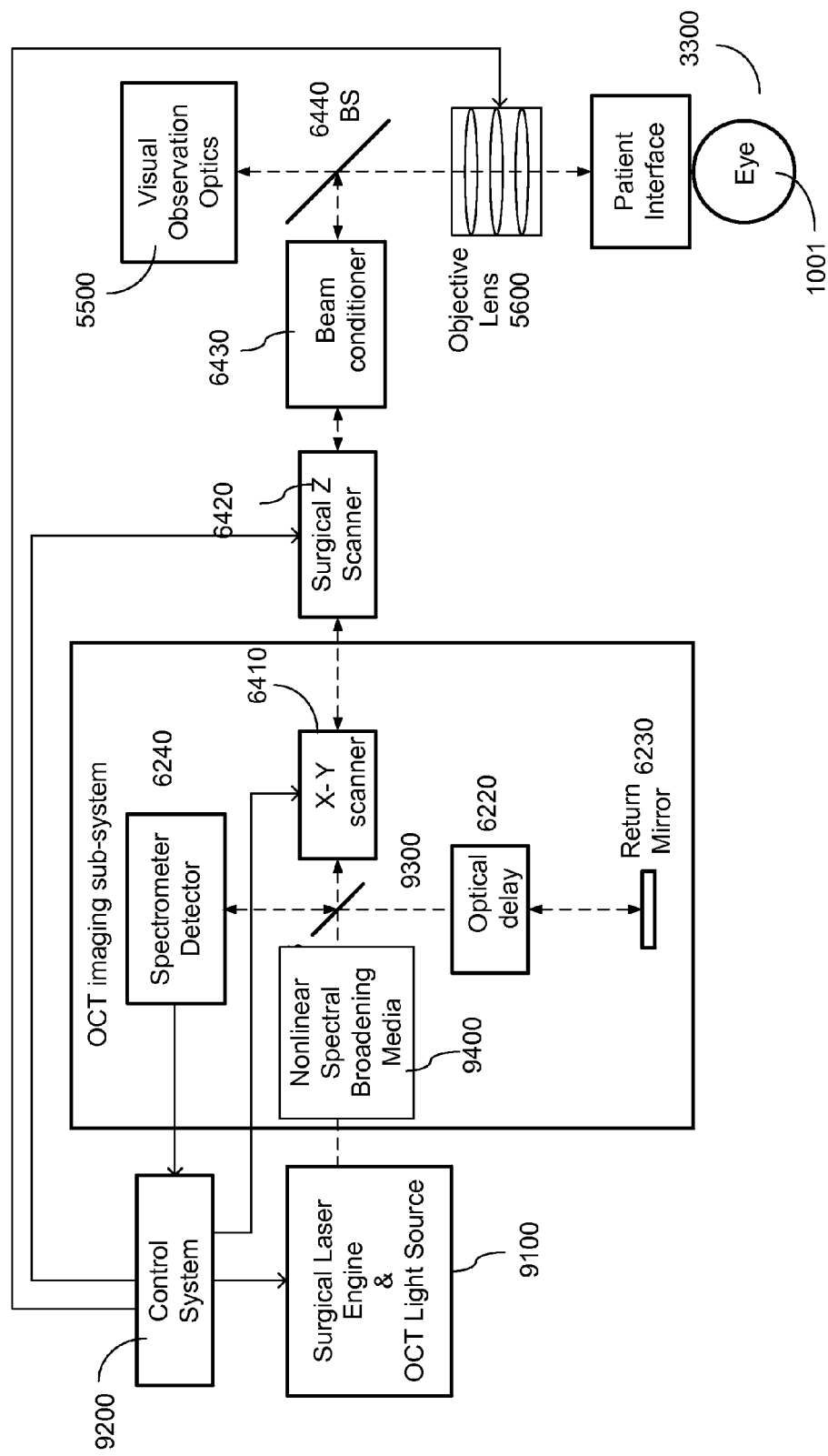

FIG. 16 shows another imaging-guided system that uses a single pulsed laser 9100 to produce the surgical light and the imaging light. A nonlinear spectral broadening media 9400 is placed in the output optical path of the femtosecond pulsed laser to use an optical non-linear process such as white light generation or spectral broadening to broaden the spectral bandwidth of the pulses from a laser source of relatively longer pulses, several hundred femtoseconds normally used in surgery. The media 9400 can be a fiber-optic material, for example. The light intensity requirements of the two systems are different and a mechanism to adjust beam intensities can be implemented to meet such requirements in the two systems. For example, beam steering mirrors, beam shutters or attenuators can be provided in the optical paths of the two systems to properly control the presence and intensity of the beam when taking an OCT image or performing surgery in order to protect the patient and sensitive instruments from excessive light intensity.

Figure 17:
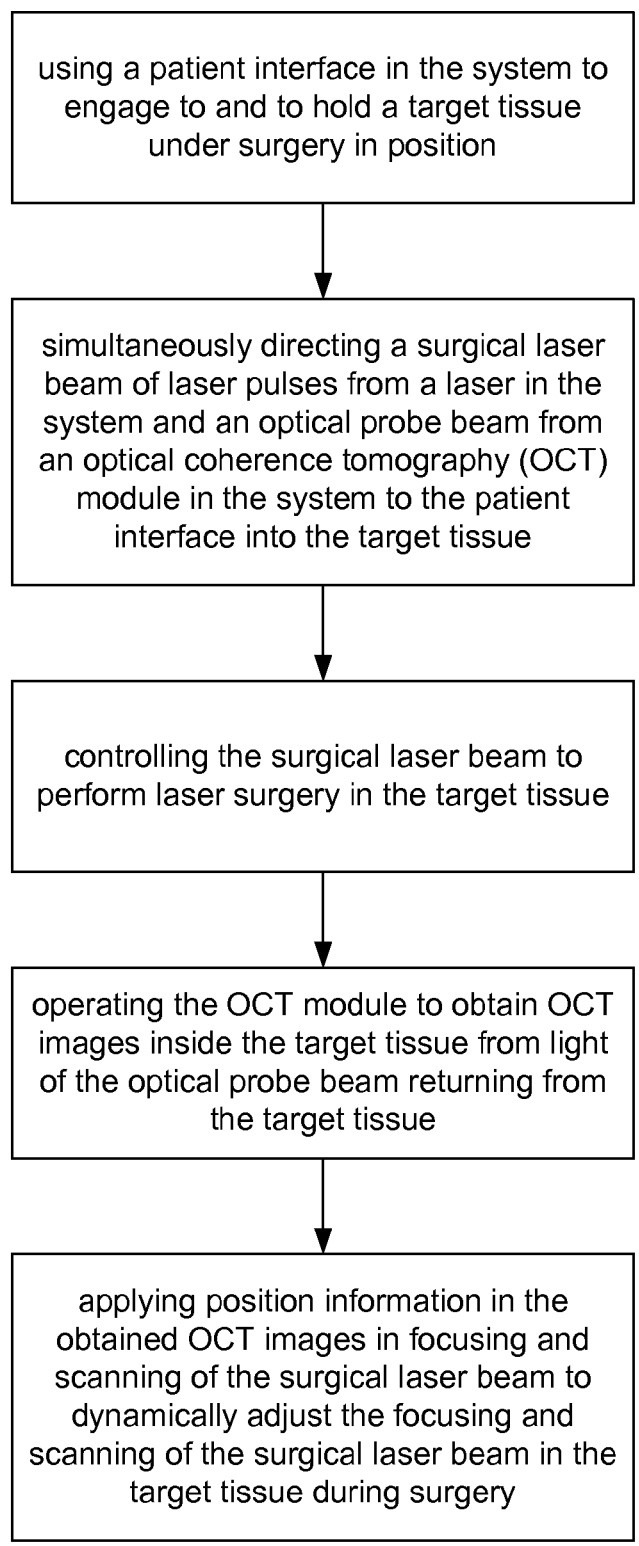
FIG. 17 shows an example of a method for performing laser surgery by suing an imaging-guided laser surgical system.

In operation, the above examples in FIGS. 8/16 can be used to perform imaging-guided laser surgery. FIG. 17 shows one example of a method for performing laser surgery by using an imaging-guided laser surgical system. This method uses a patient interface in the system to engage to and to hold a target tissue under surgery in position and simultaneously directs a surgical laser beam of laser pulses from a laser in the system and an optical probe beam from the OCT module in the system to the patient interface into the target tissue. The surgical laser beam is controlled to perform laser surgery in the target tissue and the OCT module is operated to obtain OCT images inside the target tissue from light of the optical probe beam returning from the target tissue. The position information in the obtained OCT images is applied in focusing and scanning of the surgical laser beam to adjust the focusing and scanning of the surgical laser beam in the target tissue before or during surgery.

Figure 18:
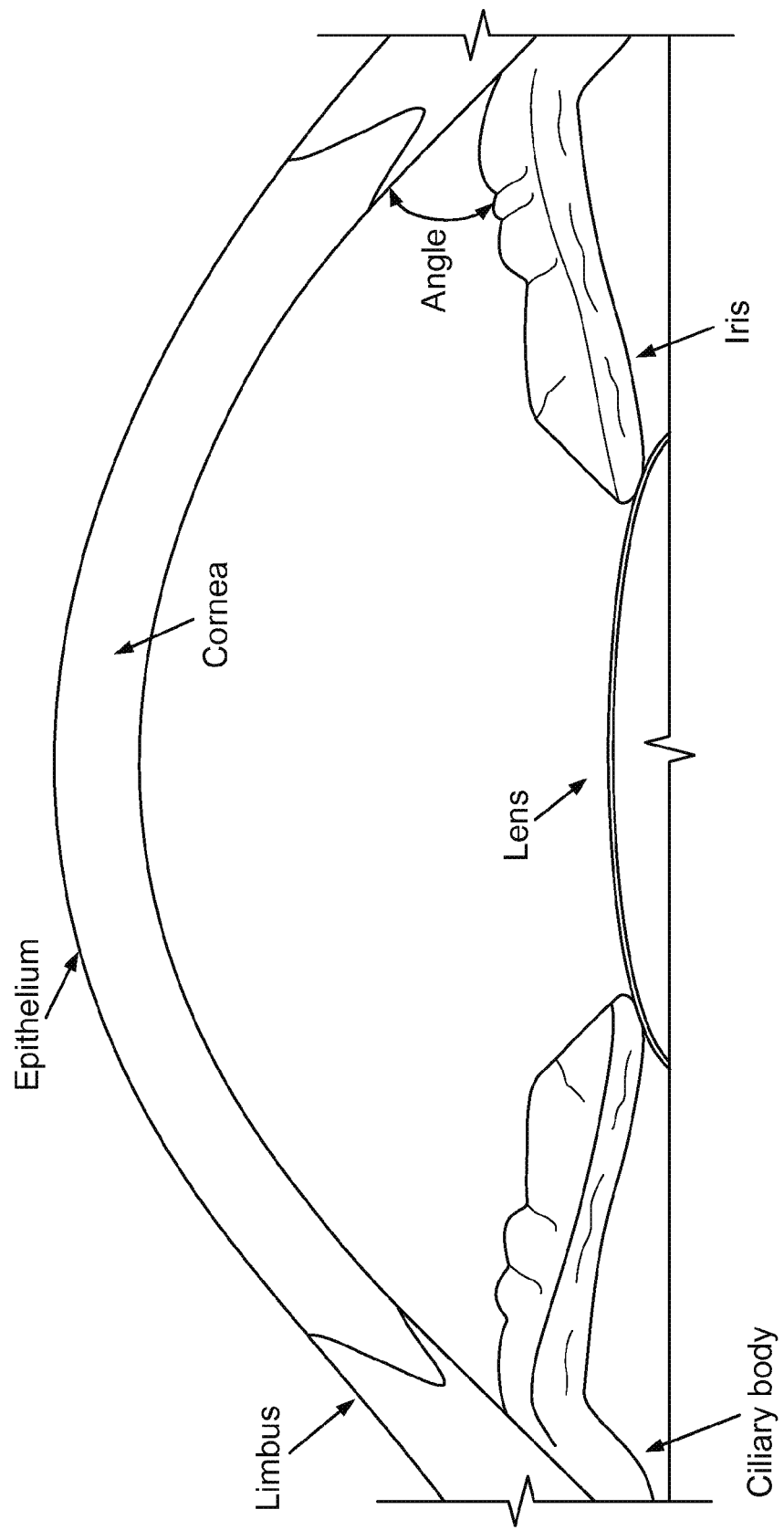
FIG. 18 shows an example of an image of an eye from an optical coherence tomography (OCT) imaging module.
Figure 19:
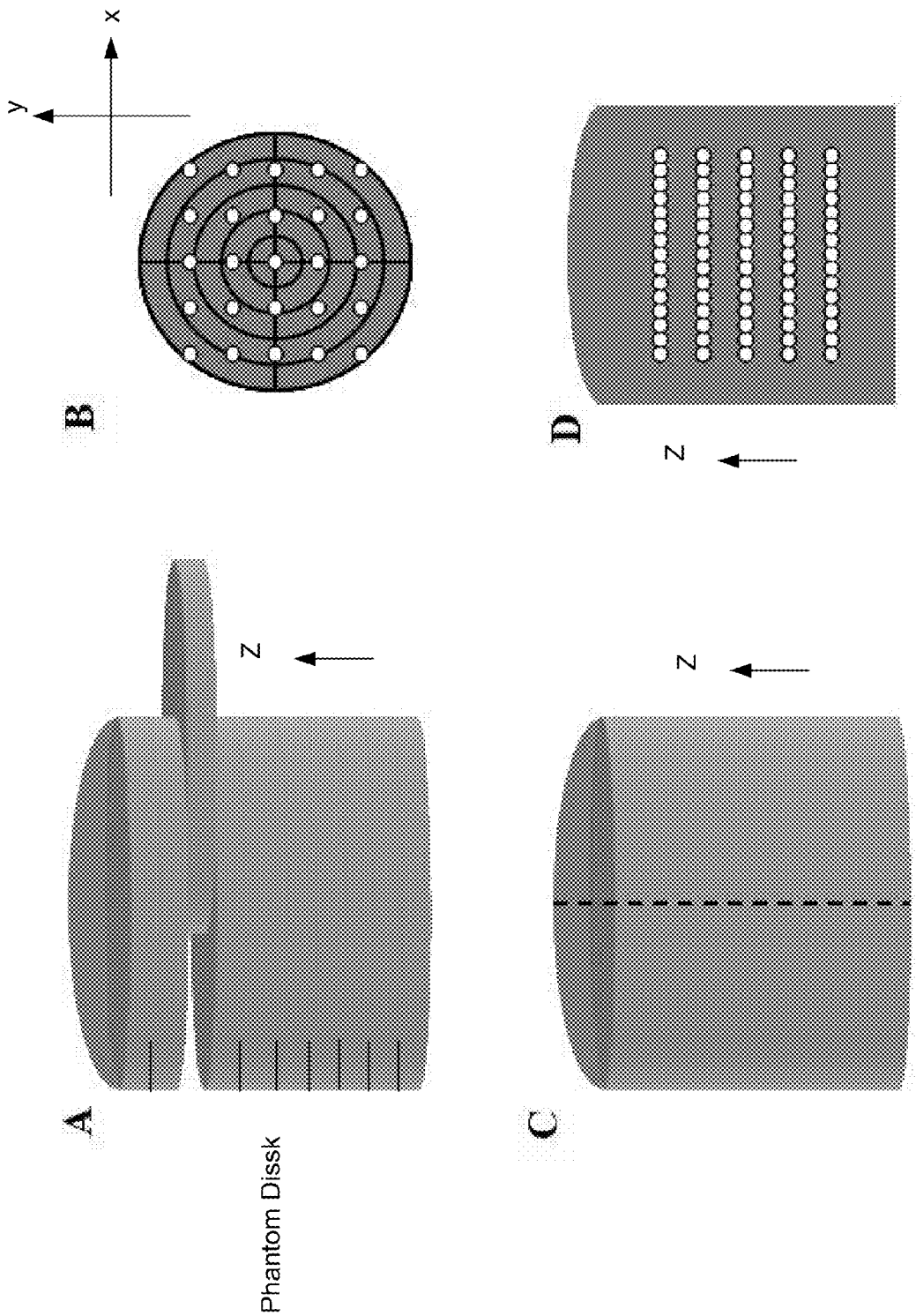
FIGS. 19A, 19B, 19C and 19D show two examples of calibration samples for calibrating an imaging-guided laser surgical system.

FIG. 18 shows an example of an OCT image of an eye. The contacting surface of the applanation lens in the patent interface can be configured to have a curvature that minimizes distortions or folds in the cornea due to the pressure exerted on the eye during applanation. After the eye is successfully applanated at the patient interface, an OCT image can be obtained. As illustrated in FIG. 18, the curvature of the lens and cornea as well as the distances between the lens and cornea are identifiable in the OCT image. Subtler features such as the epithelium-cornea interface are detectable. Each of these identifiable features may be used as an internal reference of the laser coordinates with the eye. The coordinates of the cornea and lens can be digitized using well-established computer vision algorithms such as Edge or Blob detection. Once the coordinates of the lens are established, they can be used to control the focusing and positioning of the surgical laser beam for the surgery.

Alternatively, a calibration sample material may be used to form a 3-D array of reference marks at locations with known position coordinates. The OCT image of the calibration sample material can be obtained to establish a mapping relationship between the known position coordinates of the reference marks and the OCT images of the reference marks in the obtained OCT image. This mapping relationship is stored as digital calibration data and is applied in controlling the focusing and scanning of the surgical laser beam during the surgery in the target tissue based on the OCT images of the target tissue obtained during the surgery. The OCT imaging system is used here as an example and this calibration can be applied to images obtained via other imaging techniques.

In an imaging-guided laser surgical system described here, the surgical laser can produce relatively high peak powers sufficient to drive strong field/multi-photon ionization inside of the eye (i.e. inside of the cornea and lens) under high numerical aperture focusing. Under these conditions, one pulse from the surgical laser generates a plasma within the focal volume. Cooling of the plasma results in a well defined damage zone or "bubble" that may be used as a reference point. The following sections describe a calibration procedure for calibrating the surgical laser against an OCT-based imaging system using the damage zones created by the surgical laser.

Before surgery can be performed, the OCT is calibrated against the surgical laser to establish a relative positioning relationship so that the surgical laser can be controlled in position at the target tissue with respect to the position associated with images in the OCT image of the target tissue obtained by the OCT. One way for performing this calibration uses a pre-calibrated target or "phantom" which can be damaged by the laser as well as imaged with the OCT. The phantom can be fabricated from various materials such as a glass or hard plastic (e.g. PMMA) such that the material can permanently record optical damage created by the surgical laser. The phantom can also be selected to have optical or other properties (such as water content) that are similar to the surgical target.

The phantom can be, e.g., a cylindrical material having a diameter of at least 10 mm (or that of the scanning range of the delivery system) and a cylindrical length of at least 10 mm long spanning the distance of the epithelium to the crystalline lens of the eye, or as long as the scanning depth of the surgical system. The upper surface of the phantom can be curved to mate seamlessly with the patient interface or the phantom material may be compressible to allow full applanation. The phantom may have a three dimensional grid such that both the laser position (in x and y) and focus (z), as well as the OCT image can be referenced against the phantom.

FIGS. 19A-19D illustrate two exemplary configurations for the phantom. FIG. 19A illustrates a phantom that is segmented into thin disks. FIG. 19B shows a single disk patterned to have a grid of reference marks as a reference for determining the laser position across the phantom (i.e. the x- and y-coordinates). The z-coordinate (depth) can be determined by removing an individual disk from the stack and imaging it under a confocal microscope.

FIG. 19C illustrates a phantom that can be separated into two halves. Similar to the segmented phantom in FIG. 19A, this phantom is structured to contain a grid of reference marks as a reference for determining the laser position in the x- and y-coordinates. Depth information can be extracted by separating the phantom into the two halves and measuring the distance between damage zones. The combined information can provide the parameters for image guided surgery.

Figure 20:
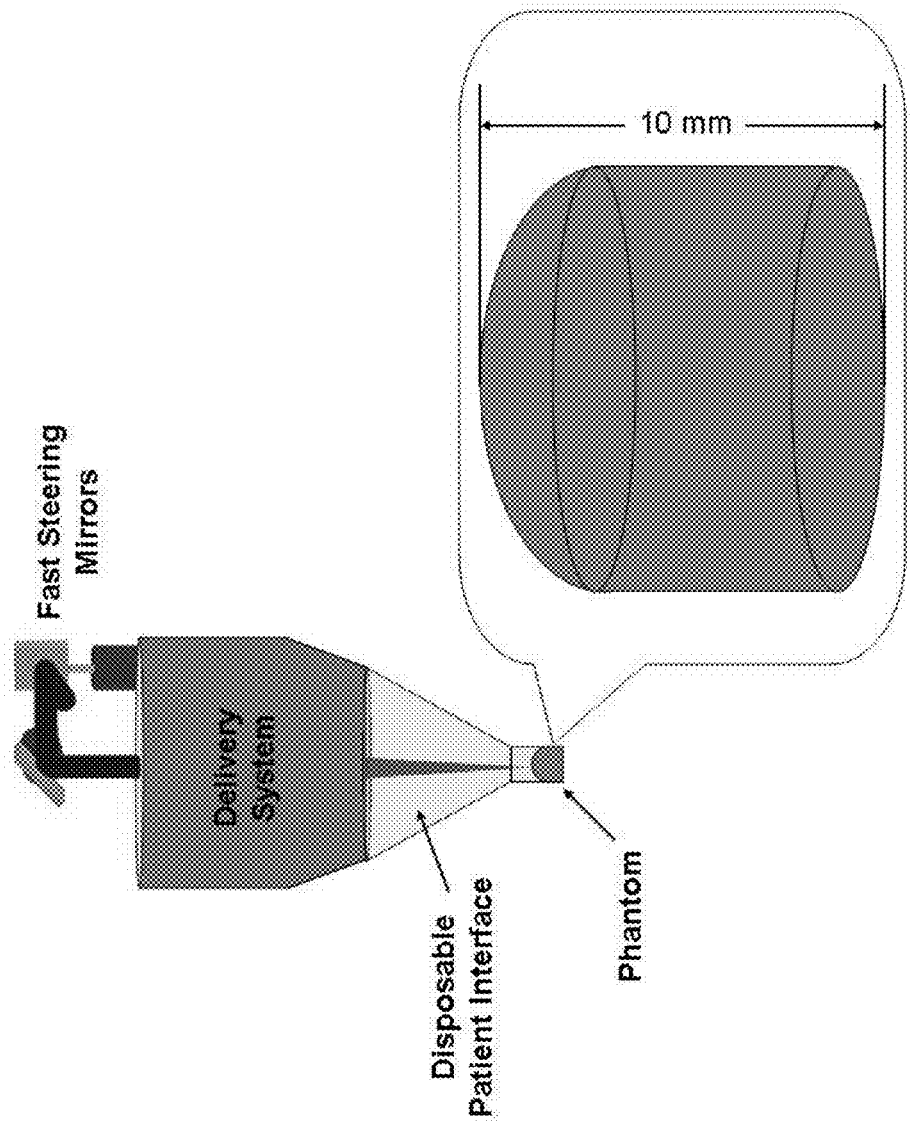
FIG. 20 shows an example of attaching a calibration sample material to a patent interface in an imaging-guided laser surgical system for calibrating the system.

FIG. 20 shows a surgical system part of the imaging-guided laser surgical system. This system includes steering mirrors which may be actuated by actuators such as galvanometers or voice coils, an objective lens e and a disposable patient interface. The surgical laser beam is reflected from the steering mirrors through the objective lens. The objective lens focuses the beam just after the patient interface. Scanning in the x- and y-coordinates is performed by changing the angle of the beam relative to the objective lens. Scanning in z-plane is accomplished by changing the divergence of the incoming beam using a system of lens upstream to the steering mirrors.

In this example, the conical section of the disposable patient interface may be either air spaced or solid and the section interfacing with the patient includes a curved contact lens. The curved contact lens can be fabricated from fused silica or other material resistant to forming color centers when irradiated with ionizing radiation. The radius of curvature is on the upper limit of what is compatible with the eye, e.g., about 10 mm.

The first step in the calibration procedure is docking the patient interface with the phantom. The curvature of the phantom matches the curvature of the patient interface. After docking, the next step in the procedure involves creating optical damage inside of the phantom to produce the reference marks.

Figure 21:
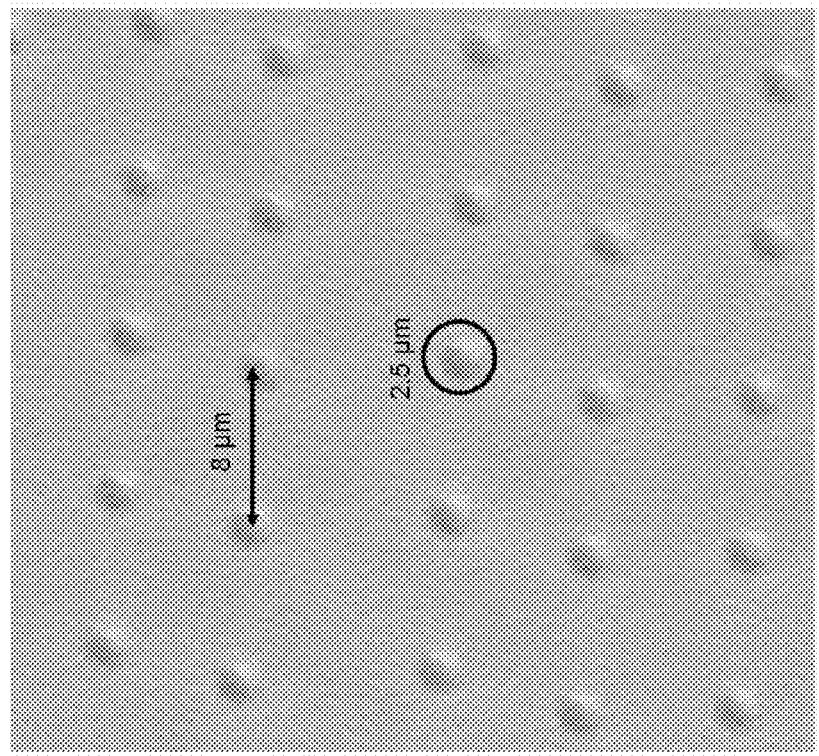
FIG. 21 shows an example of reference marks created by a surgical laser beam on a glass surface.

FIG. 21 shows examples of actual damage zones produced by a femtosecond laser in glass. The separation between the damage zones is on average 8 μm (the pulse energy is 2.2 μJ with duration of 580 fs at full width at half maximum). The optical damage depicted in FIG. 21 shows that the damage zones created by the femtosecond laser are well-defined and discrete. In the example shown, the damage zones have a diameter of about 2.5 μm. Optical damage zones similar to that shown in FIG. 20 are created in the phantom at various depths to form a 3-D array of the reference marks. These damage zones are referenced against the calibrated phantom either by extracting the appropriate disks and imaging it under a confocal microscope (FIG. 19A) or by splitting the phantom into two halves and measuring the depth using a micrometer (FIG. 19C). The x- and y-coordinates can be established from the pre-calibrated grid.

After damaging the phantom with the surgical laser, OCT on the phantom is performed. The OCT imaging system provides a 3D rendering of the phantom establishing a relationship between the OCT coordinate system and the phantom. The damage zones are detectable with the imaging system. The OCT and laser may be cross-calibrated using the phantom's internal standard. After the OCT and the laser are referenced against each other, the phantom can be discarded.

Prior to surgery, the calibration can be verified. This verification step involves creating optical damage at various positions inside of a second phantom. The optical damage should be intense enough such that the multiple damage zones which create a circular pattern can be imaged by the OCT. After the pattern is created, the second phantom is imaged with the OCT. Comparison of the OCT image with the laser coordinates provides the final check of the system calibration prior to surgery.

Once the coordinates are fed into the laser, laser surgery can be performed inside the eye. This involves photo-emulsification of the lens using the laser, as well as other laser treatments to the eye. The surgery can be stopped at any time and the anterior segment of the eye (FIG. 17) can be re-imaged to monitor the progress of the surgery; moreover, after the IOL is inserted, imaging the IOL (with light or no applanation) provides information regarding the position of the IOL in the eye. This information may be utilized by the physician to refine the position of the IOL.

Figure 22:
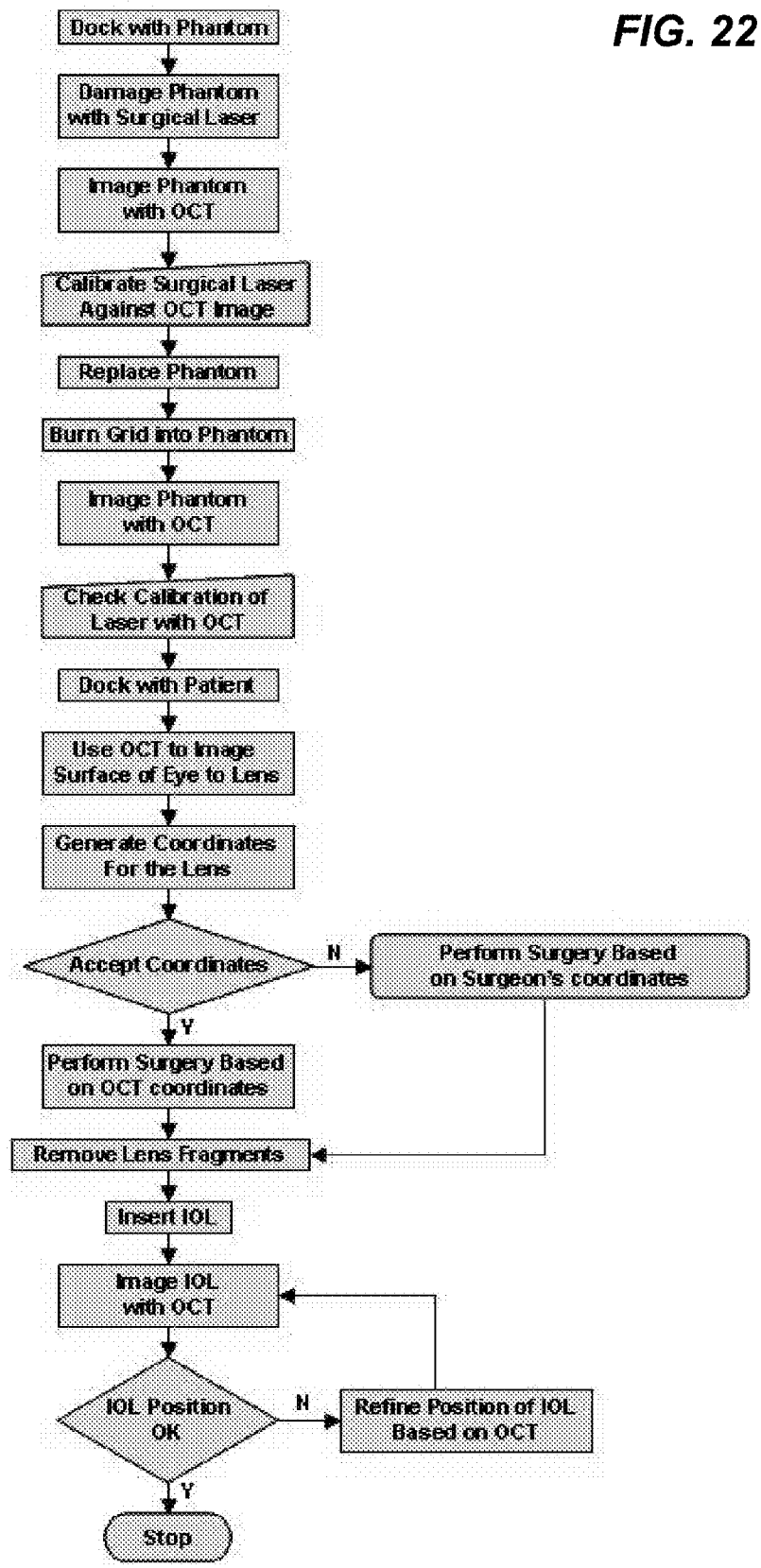
FIG. 22 shows an example of the calibration process and the post-calibration surgical operation for an imaging-guided laser surgical system.

FIG. 22 shows an example of the calibration process and the post-calibration surgical operation. This examples illustrates a method for performing laser surgery by using an imaging-guided laser surgical system can include using a patient interface in the system, that is engaged to hold a target tissue under surgery in position, to hold a calibration sample material during a calibration process before performing a surgery; directing a surgical laser beam of laser pulses from a laser in the system to the patient interface into the calibration sample material to burn reference marks at selected three-dimensional reference locations; directing an optical probe beam from an optical coherence tomography (OCT) module in the system to the patient interface into the calibration sample material to capture OCT images of the burnt reference marks; and establishing a relationship between positioning coordinates of the OCT module and the burnt reference marks. After the establishing the relationship, a patient interface in the system is used to engage to and to hold a target tissue under surgery in position. The surgical laser beam of laser pulses and the optical probe beam are directed to the patient interface into the target tissue. The surgical laser beam is controlled to perform laser surgery in the target tissue. The OCT module is operated to obtain OCT images inside the target tissue from light of the optical probe beam returning from the target tissue and the position information in the obtained OCT images and the established relationship are applied in focusing and scanning of the surgical laser beam to adjust the focusing and scanning of the surgical laser beam in the target tissue during surgery. While such calibrations can be performed immediately prior to laser surgery, they can also be performed at various intervals before a procedure, using calibration validations that demonstrated a lack of drift or change in calibration during such intervals.

The following examples describe imaging-guided laser surgical techniques and systems that use images of laser-induced photodisruption byproducts for alignment of the surgical laser beam.

Figure 23A:
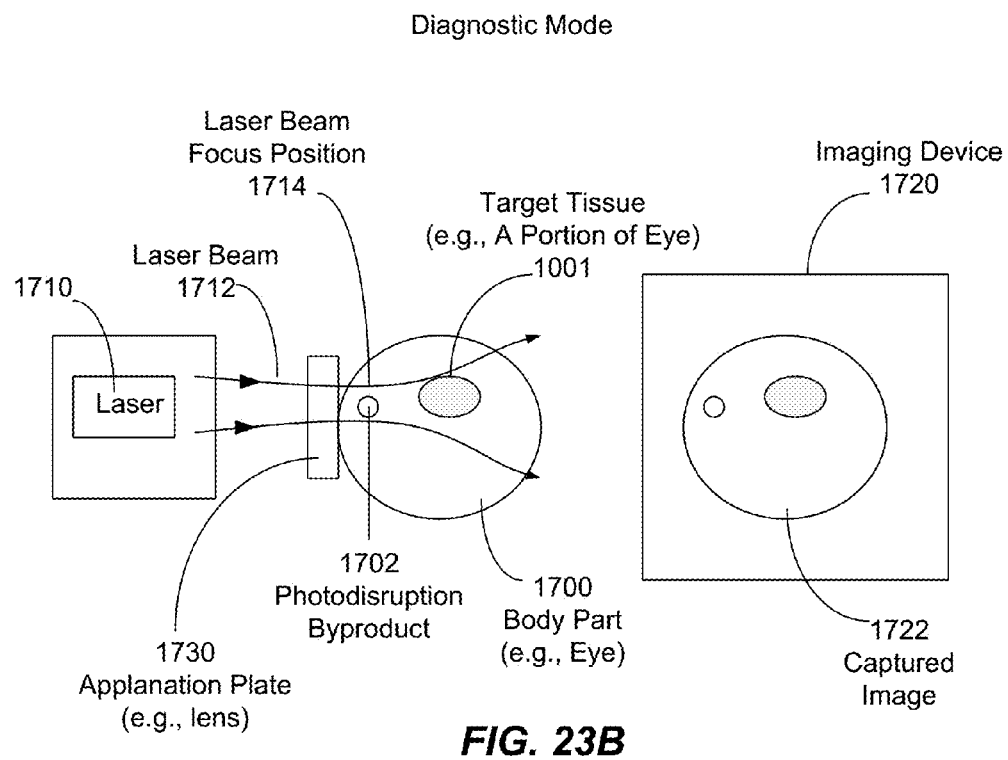
FIGS. 23A and 23B show two operation modes of an exemplary imaging-guided laser surgical system that captures images of laser-induced photodisruption byproduct and the target issue to guide laser alignment.
Figure 23B:
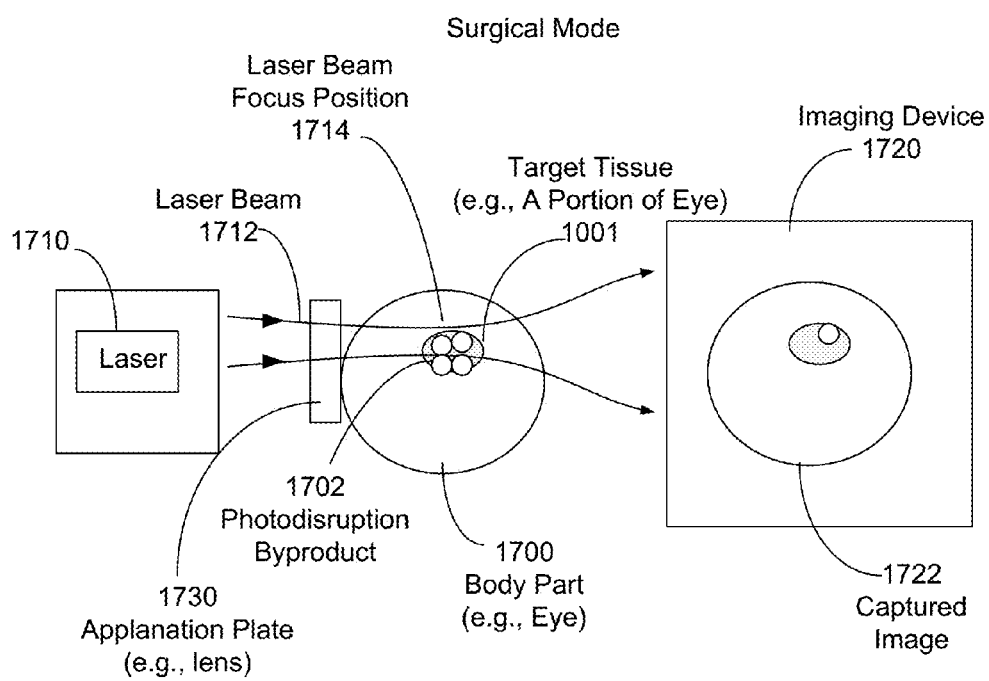

FIGS. 23A and 23B illustrate another implementation of the present technique in which actual photodisruption byproducts in the target tissue are used to guide further laser placement. A pulsed laser 1710, such as a femtosecond or picosecond laser, is used to produce a laser beam 1712 with laser pulses to cause photodisruption in a target tissue 1001. The target tissue 1001 may be a part of a body part 1700 of a subject, e.g., a portion of the lens of one eye. The laser beam 1712 is focused and directed by an optics module for the laser 1710 to a target tissue position in the target tissue 1001 to achieve a certain surgical effect. The target surface is optically coupled to the laser optics module by an applanation plate 1730 that transmits the laser wavelength, as well as image wavelengths from the target tissue. The applanation plate 1730 can be an applanation lens. An imaging device 1720 is provided to collect reflected or scattered light or sound from the target tissue 1001 to capture images of the target tissue 1001 either before or after (or both) the applanation plate is applied. The captured imaging data is then processed by the laser system control module to determine the desired target tissue position. The laser system control module moves or adjusts optical or laser elements based on standard optical models to ensure that the center of photodisruption byproduct 1702 overlaps with the target tissue position. This can be a dynamic alignment process where the images of the photodisruption byproduct 1702 and the target tissue 1001 are continuously monitored during the surgical process to ensure that the laser beam is properly positioned at each target tissue position.

In one implementation, the laser system can be operated in two modes: first in a diagnostic mode in which the laser beam 1712 is initially aligned by using alignment laser pulses to create photodisruption byproduct 1702 for alignment and then in a surgical mode where surgical laser pulses are generated to perform the actual surgical operation. In both modes, the images of the disruption byproduct 1702 and the target tissue 1001 are monitored to control the beam alignment. FIG. 17A shows the diagnostic mode where the alignment laser pulses in the laser beam 1712 may be set at a different energy level than the energy level of the surgical laser pulses. For example, the alignment laser pulses may be less energetic than the surgical laser pulses but sufficient to cause significant photodisruption in the tissue to capture the photodisruption byproduct 1702 at the imaging device 1720. The resolution of this coarse targeting may not be sufficient to provide desired surgical effect. Based on the captured images, the laser beam 1712 can be aligned properly. After this initial alignment, the laser 1710 can be controlled to produce the surgical laser pulses at a higher energy level to perform the surgery. Because the surgical laser pulses are at a different energy level than the alignment laser pulses, the nonlinear effects in the tissue material in the photodisruption can cause the laser beam 1712 to be focused at a different position from the beam position during the diagnostic mode. Therefore, the alignment achieved during the diagnostic mode is a coarse alignment and additional alignment can be further performed to precisely position each surgical laser pulse during the surgical mode when the surgical laser pulses perform the actual surgery. Referring to FIG. 23A, the imaging device 1720 captures the images from the target tissue 1001 during the surgical mode and the laser control module adjust the laser beam 1712 to place the focus position 1714 of the laser beam 1712 onto the desired target tissue position in the target tissue 1001. This process is performed for each target tissue position.

Figure 24:
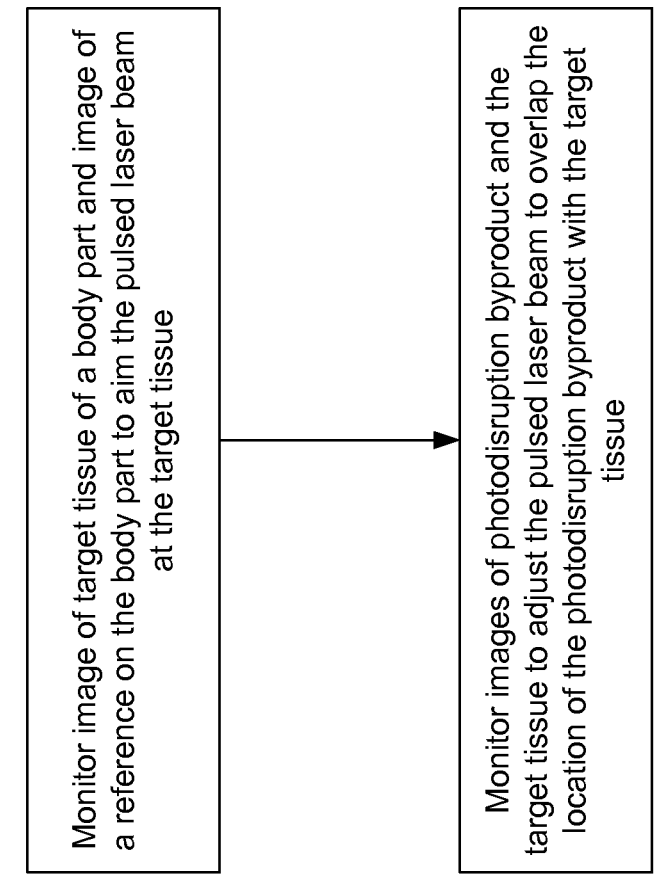
FIGS. 24 and 25 show examples of laser alignment operations in imaging-guided laser surgical systems.

FIG. 24 shows one implementation of the laser alignment where the laser beam is first approximately aimed at the target tissue and then the image of the photodisruption byproduct is captured and used to align the laser beam. The image of the target tissue of the body part as the target tissue and the image of a reference on the body part are monitored to aim the pulsed laser beam at the target tissue. The images of photodisruption byproduct and the target tissue are used to adjust the pulsed laser beam to overlap the location of the photodisruption byproduct with the target tissue.

Figure 25:
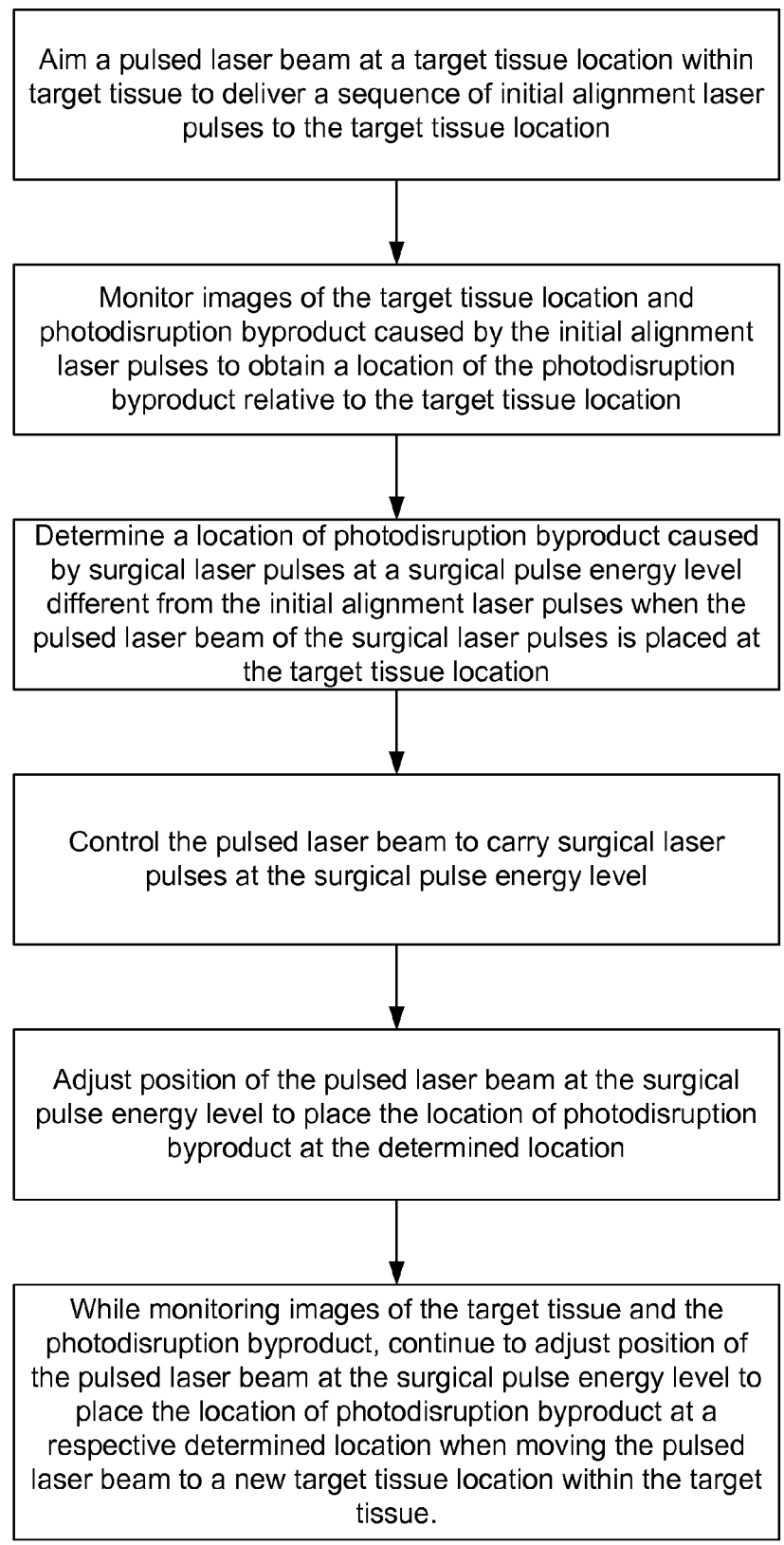

FIG. 25 shows one implementation of the laser alignment method based on imaging photodisruption byproduct in the target tissue in laser surgery. In this method, a pulsed laser beam is aimed at a target tissue location within target tissue to deliver a sequence of initial alignment laser pulses to the target tissue location. The images of the target tissue location and photodisruption byproduct caused by the initial alignment laser pulses are monitored to obtain a location of the photodisruption byproduct relative to the target tissue location. The location of photodisruption byproduct caused by surgical laser pulses at a surgical pulse energy level different from the initial alignment laser pulses is determined when the pulsed laser beam of the surgical laser pulses is placed at the target tissue location. The pulsed laser beam is controlled to carry surgical laser pulses at the surgical pulse energy level. The position of the pulsed laser beam is adjusted at the surgical pulse energy level to place the location of photodisruption byproduct at the determined location. While monitoring images of the target tissue and the photodisruption byproduct, the position of the pulsed laser beam at the surgical pulse energy level is adjusted to place the location of photodisruption byproduct at a respective determined location when moving the pulsed laser beam to a new target tissue location within the target tissue.

Figure 26:
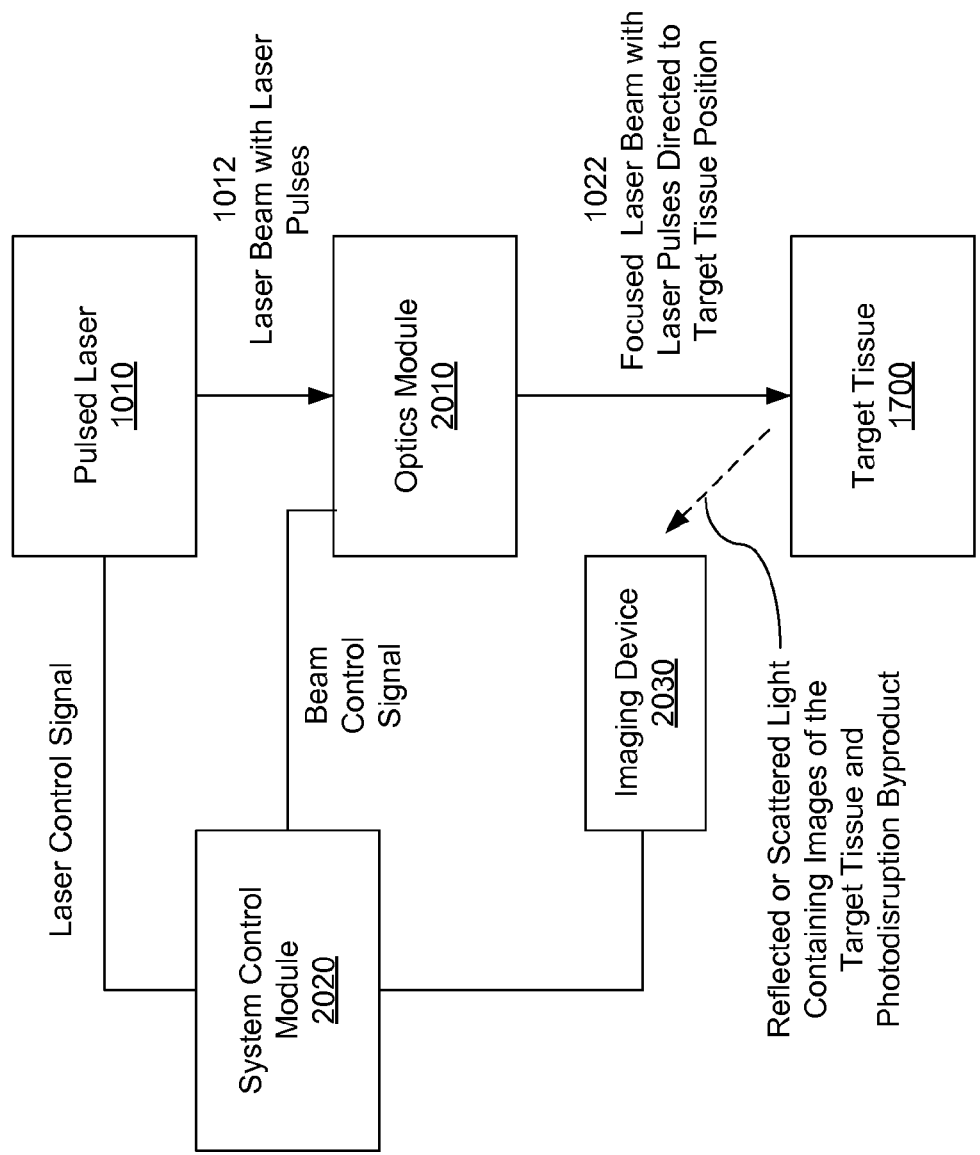
FIG. 26 shows an exemplary laser surgical system based on the laser alignment using the image of the photodisruption byproduct.

FIG. 26 shows an exemplary laser surgical system based on the laser alignment using the image of the photodisruption byproduct. An optics module 2010 is provided to focus and direct the laser beam to the target tissue 1700. The optics module 2010 can include one or more lenses and may further include one or more reflectors. A control actuator is included in the optics module 2010 to adjust the focusing and the beam direction in response to a beam control signal. A system control module 2020 is provided to control both the pulsed laser 1010 via a laser control signal and the optics module 2010 via the beam control signal. The system control module 2020 processes image data from the imaging device 2030 that includes the position offset information for the photodisruption byproduct 1702 from the target tissue position in the target tissue 1700. Based on the information obtained from the image, the beam control signal is generated to control the optics module 2010 which adjusts the laser beam. A digital processing unit is included in the system control module 2020 to perform various data processing for the laser alignment.

The imaging device 2030 can be implemented in various forms, including an optical coherent tomography (OCT) device. In addition, an ultrasound imaging device can also be used. The position of the laser focus is moved so as to place it grossly located at the target at the resolution of the imaging device. The error in the referencing of the laser focus to the target and possible non-linear optical effects such as self focusing that make it difficult to accurately predict the location of the laser focus and subsequent photodisruption event. Various calibration methods, including the use of a model system or software program to predict focusing of the laser inside a material can be used to get a coarse targeting of the laser within the imaged tissue. The imaging of the target can be performed both before and after the photodisruption. The position of the photodisruption by products relative to the target is used to shift the focal point of the laser to better localize the laser focus and photodisruption process at or relative to the target. Thus the actual photodisruption event is used to provide a precise targeting for the placement of subsequent surgical pulses.

Photodisruption for targeting during the diagnostic mode can be performed at a lower, higher or the same energy level that is required for the later surgical processing in the surgical mode of the system. A calibration may be used to correlate the localization of the photodisruptive event performed at a different energy in diagnostic mode with the predicted localization at the surgical energy because the optical pulse energy level can affect the exact location of the photodisruptive event. Once this initial localization and alignment is performed, a volume or pattern of laser pulses (or a single pulse) can be delivered relative to this positioning. Additional sampling images can be made during the course of delivering the additional laser pulses to ensure proper localization of the laser (the sampling images may be obtained with use of lower, higher or the same energy pulses). In one implementation, an ultrasound device is used to detect the cavitation bubble or shock wave or other photodisruption byproduct. The localization of this can then be correlated with imaging of the target, obtained via ultrasound or other modality. In another embodiment, the imaging device is simply a biomicroscope or other optical visualization of the photodisruption event by the operator, such as optical coherence tomography. With the initial observation, the laser focus is moved to the desired target position, after which a pattern or volume of pulses is delivered relative to this initial position.

As a specific example, a laser system for precise subsurface photodisruption can include means for generating laser pulses capable of generating photodisruption at repetition rates of 100-1000 Million pulses per second, means for coarsely focusing laser pulses to a target below a surface using an image of the target and a calibration of the laser focus to that image without creating a surgical effect, means for detecting or visualizing below a surface to provide an image or visualization of a target the adjacent space or material around the target and the byproducts of at least one photodisruptive event coarsely localized near the target, means for correlating the position of the byproducts of photodisruption with that of the sub surface target at least once and moving the focus of the laser pulse to position the byproducts of photodisruption at the sub surface target or at a relative position relative to the target, means for delivering a subsequent train of at least one additional laser pulse in pattern relative to the position indicated by the above fine correlation of the byproducts of photodisruption with that of the sub surface target, and means for continuing to monitor the photodisruptive events during placement of the subsequent train of pulses to further fine tune the position of the subsequent laser pulses relative to the same or revised target being imaged.

The above techniques and systems can be used deliver high repetition rate laser pulses to subsurface targets with a precision required for contiguous pulse placement, as needed for cutting or volume disruption applications. This can be accomplished with or without the use of a reference source on the surface of the target and can take into account movement of the target following applanation or during placement of laser pulses.

While this specification described various embodiments and implementations, these should not be construed as limitations on the scope of an invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Also, enhancements, combinations, extensions and variations can be made based on what is disclosed and illustrated.

What is claimed is:

1. A method of treating a crystalline lens of an eye with a laser, the method comprising:
   selecting a surgical region of the lens; and
   forming an incision in the surgical region on a layer-by-layer basis by scanning a laser beam with an XY scanner of a laser delivery optics along a curved focal plane of the laser delivery optics to form a line of bubbles in each layer without adjusting a Z scanner of the laser delivery optics at a scanning rate of the XY scanner, wherein:
      an orientation of a portion of the incisions is one of an orientation intersecting fibers of the lens and an orientation non-transverse to an axis of the eye; and
      the incision has a spatial extent in a Z direction in the range of 0.5-10 mm, and in an X-Y plane in the range of 2-10 mm.

2. The method of claim 1, wherein the non-transverse orientation of the incision is one of:
   an orientation substantially parallel to the axis of the eye; and
   an orientation making a less than 90 degree angle with the axis of the eye.

3. The method of claim 1, wherein:
a spatial extent of the incision along the axis of the eye is longer than the spatial extent transverse to the axis of the eye.

4. The method of claim 1, wherein:
the axis of the eye is one of a visual axis, an optic axis, a line of sight and a pupillary axis.

5. The method of claim 1, wherein:
the incision cuts the fibers into parts approximately at the intersection of the incision and the fibers; and
the modified property of the lens is a weakening of a biomechanical property of the lens.

6. The method of claim 1, wherein:
the incision cuts the fibers at or near sutures of the fibers.

7. The method of claim 1, wherein:
the incision avoids cutting sutures in the lens.

8. The method of claim 1, wherein the applying laser pulses comprises:
applying the laser pulses to generate gas bubbles which form the incision,
wherein an orientation of the incision is aligned with a preferential direction of expansion of the generated gas bubbles.

9. The method of claim 1, wherein the applying the laser pulses comprises:
moving the focal point of the applied laser beam along a posterior to anterior direction within the lens.

10. The method of claim 1, wherein:
the method comprises forming no more than one incision; and
the laser pulses are applied in a continuous manner to form the incision without repositioning the laser or interrupting the application of the laser.

11. The method of claim 1, wherein the incision has a form aligned with the axis of the eye, the form being of at least one of:
a cylinder, a set of concentric cylinders, a set of cylinders connected by one or more connecting line, a curved surface, a cone, a spiral, a layered spiral with smooth lines connecting layers of the spiral and a tilted cylinder.

12. The method of claim 1, wherein the incision has a form aligned with the axis of the eye, the form being at least one of:
a plane, two or more crossing planes, a combination of planes and connecting arcs, and a combination of planes and cylinders.

13. The method of claim 1, wherein the applying the laser pulses comprises:
applying the laser pulses to form a first ring with a first radius in a posterior layer of the lens;
applying the laser pulses to form a connector line between the first and a second ring in the posterior layer;
applying the laser pulses to form the second ring with a second radius in the posterior layer; and
repeating multiple times the formation of the first ring, the second ring and the connector line in layers sequentially anterior to the posterior layer,
wherein the first rings in the sequential layers form a first cylinder, the second rings form a second cylinder, the cylinders being connected by the connector lines.

14. The method of claim 13, wherein:
the connector lines in sequential layers are one of:
aligned to form connector planes; and
not-aligned from layer to layer.

15. The method of claim 1, comprising:
forming a posterior spiral in a posterior layer;
forming a smooth connector line starting near an end of the posterior spiral in the posterior layer, the connector line smoothly bending and rising to a central region of a layer anterior to the posterior layer; and
forming an anterior spiral starting at the end of the smooth connector line in the central region of the anterior layer.

16. The method of claim 15, wherein the posterior spiral and the anterior spiral are essentially aligned to form a spiral with an extent in the Z direction.

17. The method of claim 1, wherein the applying the laser pulses comprises:
selecting laser-parameters sufficient to create bubbles in the lens, but insufficient to cause harm to a retina of the eye.

18. The method of claim 1, wherein the applying the laser pulses comprises:
applying the laser pulses with laser-parameters insufficient to fragment the lens to a degree suitable for removal, if the incision were transverse to the axis of the eye.

19. The method of claim 18, wherein the laser-parameters comprise:
a laser pulse energy in the range of 0.5 microJ to 50 microJ;
a duration of a laser pulse in the range of 0.005 picoseconds to 25 picoseconds;
a repetition rate of applying laser pulses in the range of 1 kHz to 10 MHz; and
a separation distance of target regions of laser pulses in the range of 1 micron to 100 microns.

20. The method of claim 1, wherein the applying the laser pulses comprises:
applying the laser pulses with varying energy as the incision is formed.

21. The method of claim 20, wherein the energy is varied during at least one of:
a Z directional scanning; and
an X-Y directional scanning.

22. The method of claim 20, wherein the energy is varied in relation to a measurement of an optical property of an eye tissue.

23. The method of claim 1, comprising:
forming the incision on a layer-by-layer basis, wherein one or more layers are at least partially formed along a curved focal plane of a laser delivery system.

24. The method of claim 1, comprising:
a Z directional scanner is adjusted at a slower rate than an X-Y directional scanner when forming a layer of one or more incisions.

25. The method of claim 1, further comprising:
forming a protection layer in a posterior portion of the lens, positioned to block a large portion of the laser pulses applied to form the incision.

26. The method of claim 1, wherein the incision fragments at least a portion of the lens, the method further comprising:
removing the fragmented portion of the lens.

27. The method of claim 26, wherein the applying the laser pulses comprises:
applying laser pulses with laser parameters which do not cause lasting damage to a retina of the eye, wherein the laser pulses fragment the lens to a degree suitable for removal; and
the time of the fragmentation is less than a minute.

* * * * *